(12) United States Patent
Wang et al.

(10) Patent No.: US 8,278,420 B2
(45) Date of Patent: Oct. 2, 2012

(54) COMPOSITION AND METHOD FOR PREVENTION AND TREATMENT OF TYPE I DIABETES

(75) Inventors: Qinghua Wang, Toronto (CA); Gerald J. Prud'homme, Toronto (CA); Mohan Kumar, Toronto (CA)

(73) Assignee: Qinghua Wang, North York (CA)

( * ) Notice: Subject to any disclaimer, the term of this patent is extended or adjusted under 35 U.S.C. 154(b) by 252 days.

(21) Appl. No.: 11/997,996

(22) PCT Filed: Aug. 4, 2006

(86) PCT No.: PCT/CA2006/001263
§ 371 (c)(1),
(2), (4) Date: Sep. 29, 2008

(87) PCT Pub. No.: WO2007/016764
PCT Pub. Date: Feb. 15, 2007

(65) Prior Publication Data
US 2009/0016968 A1   Jan. 15, 2009

Related U.S. Application Data

(60) Provisional application No. 60/595,803, filed on Aug. 6, 2005.

(51) Int. Cl.
*C07K 16/00* (2006.01)
(52) U.S. Cl. .................................................. 530/387.1
(58) Field of Classification Search ........................ None
See application file for complete search history.

(56) References Cited

U.S. PATENT DOCUMENTS

| 5,998,366 | A | 12/1999 | Tobin et al. |
| 2004/0053370 | A1 | 3/2004 | Glaesner et al. |
| 2009/0181912 | A1 | 7/2009 | Wang |

OTHER PUBLICATIONS

Bosma, P.T., et al. Mol. Biol. Evol. 1999;16(3):397-404.*
Ogawa, N. et al. Cure of overt diabetes in NOD mice by transient treatment with anti-lymphocyte serum and exendin-4. Diabetes, Jul. 2004, vol. 53, No. 7, pp. 1700-1705.
Prud'homme, G.J. et al. DNA vaccines that induce regulatory T cells and protect against autoimmune diabetes. Gene Ther. Mol. Biol. Sep. 2005, vol. 9, pp. 183-192.
Holst, J.J. et al. The incretin approach for diabetes treatment. Modulation of islet hormone release by GLP-1 agonism. Diabetes. Dec. 2004, vol. 53 Suppl. 3, pp. S197-S204.
Prud'homme, G.J. et al. Prevention of autoimmune diabetes by intramuscular gene therapy with a nonviral vector encoding an interferon-gamma receptor/IgG1 fusion protein. Gene Ther. May 1999, vol. 6, No. 5, pp. 771-777.
Yu L.P. et al., "Diabetes Prevention Trial 1: Prevalence of GAD and ICA512 (IA-2) Autoantibodies . . . ", Annals of the New York Academy of Sciences, 2002, pp. 254-258.
Carel, J., "Therapy to Prevent Type 1 Diabetes Mellitus", New England Journal of Medicine, Oct. 3, 2002, pp. 1115-1116, vol. 347.
Sia, C. et al., "Tolerance Induction and Endogenous Regeneration of Pancreatic β-Cells in Established . . . Diabetes", Review of Diabetic Studies, 2004, pp. 198-206, vol. 1(4).
Ogawa, N. et al, "Cure of Overt Diabetes in NOD Mice by Transient Treatment With Anti-Lymphocyte Serum and Exendin-4", Diabetes, 2004, pp. 1700-1705, vol. 53.
Sherry, N. A. et al, "Exendin-4 Improves Reversal of Diabetes in NOD Mice Treated with Anti-CD3 Monoclonal Antbody . . . ", Endocrinology, 2007, pp. 5136-5144, vol. 148, No. 11.
Keymeulen, B. et al., "Insulin Needs after CD3-Antibody Therapy in New-Onset Type 1 Diabetes", New England Journal of Medicine, Jun. 23, 2005, pp. 2598-2608, vol. 352.
Prud'homme G.J. et al., 2002, Immunoinhibitory DNA vaccine protects against autoimmune diabetes through cDNA encoding a selectice CTLA-4 (CD152) ligand. Hum Gene Ther 13:395.
Glinka Y., 2003, Regulatory cytokine production stimulated by DNA vaccination against an altered form of glutamic acid decarboxylase 65 in nanobese diabetic mice. J Mol Med 81.
Malendowics L.K., "Effects of prolonged exendin-4 administration on entero-insular axis of normal and streptozocin-induced diabetic rats", Int. J. Mol. Med. Jun. 2003, vol. 11, No. 6, pp. 763-766.
Kieffer T.J., et al., "The Glucagon-Like Peptides", Endocrine Review, 1999, vol. 20, pp. 867-913.
Glinka, Y. et al., "Protective regulatory T cell generation in autoimmune diabetes by DNA covaccination with islet antigens and a selective CTLA-4 ligand", Molecular Therapy, Oct. 2006, vol. 14, No. 4, pp. 578-587.

* cited by examiner

*Primary Examiner* — Gerald R Ewoldt
(74) *Attorney, Agent, or Firm* — Bereskin & Parr LLP; Micheline Gravelle; Carmela DeLuca

(57) ABSTRACT

A composition for the prevention or treatment of type I diabetes in a subject, said composition comprising a fusion protein selected from the group consisting of GLP-1/IgG or variant or fragment thereof and an Ex4/IgG or variant or fragment thereof and an autoimmune suppressor for silencing an autoimmune response against islet beta cells.

4 Claims, 18 Drawing Sheets

SEQUENCE LISTING

<160> NUMBER OF SEQ ID NOS: 26

<210> SEQ ID NO 1
<211> LENGTH: 30
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 39
<212> TYPE: PRT
<213> ORGANISM: Heloderma suspectum

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 249
<212> TYPE: PRT
<213> ORGANISM: Artificial Sequence
<220> FEATURE:
<223> OTHER INFORMATION: Synthetic construct

<400> SEQUENCE: 3

Pro Ser Glu Thr Val Thr Cys Asn Val Ala His Pro Ala Ser Ser Thr
1               5                   10                  15

Lys Val Asp Lys Lys Ile Val Pro Arg Asp Cys Gly Cys Lys Pro Cys
            20                  25                  30

Ile Cys Thr Val Pro Glu Val Ser Ser Val Phe Ile Phe Pro Pro Lys
        35                  40                  45

Pro Lys Asp Val Leu Thr Ile Thr Leu Thr Pro Lys Val Thr Cys Val
    50                  55                  60

Val Val Asp Ile Ser Lys Asp Asp Pro Glu Val Gln Phe Ser Trp Phe
65                  70                  75                  80

Val Asp Asp Val Glu Val His Thr Ala Gln Thr Gln Pro Arg Glu Glu
                85                  90                  95

Gln Phe Asn Ser Thr Phe Arg Ser Val Ser Glu Leu Pro Ile Met His
            100                 105                 110

Gln Asp Trp Leu Asn Gly Lys Glu Phe Lys Cys Arg Val Asn Ser Ala
        115                 120                 125

Ala Phe Pro Ala Pro Ile Glu Lys Thr Ile Ser Lys Thr Lys Gly Arg
    130                 135                 140

Pro Lys Ala Pro Gln Val Tyr Thr Ile Pro Pro Pro Lys Glu Gln Met
145                 150                 155                 160

Ala Lys Asp Lys Val Ser Leu Thr Cys Met Ile Thr Asp Phe Phe Pro
                165                 170                 175

Glu Asp Ile Thr Val Glu Trp Gln Trp Asn Gly Gln Pro Ala Glu Asn
            180                 185                 190

Tyr Lys Asn Thr Gln Pro Ile Met Asn Thr Asn Gly Ser Tyr Phe Val
        195                 200                 205

Tyr Ser Lys Leu Asn Val Gln Lys Ser Asn Trp Glu Ala Gly Asn Thr
    210                 215                 220

Phe Thr Cys Ser Val Leu His Glu Gly Leu His Asn His His Thr Glu
225                 230                 235                 240

Lys Ser Leu Ser His Ser Pro Gly Lys
                245

<210> SEQ ID NO 4
<211> LENGTH: 902
<212> TYPE: DNA
<213> ORGANISM: Artificial Sequence
<220> FEATURE:
<223> OTHER INFORMATION: Synthetic construct

<400> SEQUENCE: 4

```
gagcgcaaat gttgtgtcga gtgcccaccg tgcccaggta agccagccca ggcctcgccc      60
tccagctcaa ggcgggacag gtgccctaga gtagcctgca tccagggaca gcccccagct     120
gggtgctgac acgtccacct ccatctcttc ctcagcacca cctgtggcag gaccgtcagt     180
cttcctcttc cccccaaaac ccaaggacac cctcatgatc tcccggaccc ctgaggtcac     240
gtgcgtggtg gtggacgtga gccacgaaga ccccgaggtc cagttcaact ggtacgtgga     300
cggcgtggag gtgcataatg ccaagacaaa gccacgggag gagcagttca acagcacgtt     360
ccgtgtggtc agcgtcctca ccgttgtgca ccaggactgg ctgaacggca aggagtacaa     420
gtgcaaggtc tccaacaaag gcctcccagc ccccatcgag aaaaccatct ccaaaaccaa     480
aggtgggacc cgcggggtat gagggccaca tggacagagg ccggctcggc ccaccctctg     540
ccctgggagt gaccgctgtg ccaacctctg tccctacagg gcagccccga gaaccacagg     600
tgtacaccct gcccccatcc cgggaggaga tgaccaagaa ccaggtcagc ctgacctgcc     660
tggtcaaagg cttctacccc agcgacatcg ccgtggagtg ggagagcaat gggcagccgg     720
agaacaacta caagaccaca cctcccatgc tggactccga cggctccttc ttcctctaca     780
gcaagctcac cgtggacaag agcaggtggc agcagggaa cgtcttctca tgctccgtga     840
tgcatgaggc tctgcacaac cactacacgc agaagagcct ctccctgtct ccgggtaaat     900
ga                                                                     902
```

<210> SEQ ID NO 5
<211> LENGTH: 228
<212> TYPE: PRT
<213> ORGANISM: Artificial Sequence
<220> FEATURE:
<223> OTHER INFORMATION: Synthetic construct

<400> SEQUENCE: 5

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140
```

```
Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
            165                 170                 175

Pro Met Leu Asp Ser Asp Gly Ser Phe Phe Leu Tyr Ser Lys Leu Thr
        180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 6
<211> LENGTH: 21
<212> TYPE: PRT
<213> ORGANISM: Homo sapiens

<400> SEQUENCE: 6

Met Glu Thr Asp Thr Leu Leu Leu Trp Val Leu Leu Leu Trp Val Pro
1               5                   10                  15

Gly Ser Thr Gly Asp
            20

<210> SEQ ID NO 7
<211> LENGTH: 57
<212> TYPE: DNA
<213> ORGANISM: Homo sapiens

<400> SEQUENCE: 7
gtgctctggg tgttcttctt tgtgatcctc accctcagca acagctccca ctgctcc      57

<210> SEQ ID NO 8
<211> LENGTH: 108
<212> TYPE: PRT
<213> ORGANISM: Homo sapiens

<400> SEQUENCE: 8

Met Ala Leu Leu Val His Phe Leu Pro Leu Leu Ala Leu Leu Ala Leu
1               5                   10                  15

Trp Glu Pro Lys Pro Thr Gln Ala Phe Val Lys Gln His Leu Cys Gly
            20                  25                  30

Pro His Leu Val Glu Ala Leu Tyr Leu Val Cys Gly Glu Arg Gly Phe
        35                  40                  45

Phe Tyr Thr Pro Lys Ser Arg Arg Glu Val Glu Asp Pro Gln Val Glu
    50                  55                  60

Gln Leu Glu Leu Gly Gly Ser Pro Gly Asp Leu Gln Thr Leu Ala Leu
65                  70                  75                  80

Glu Val Ala Arg Gln Lys Arg Gly Ile Val Asp Gln Cys Cys Thr Ser
                85                  90                  95

Ile Cys Ser Leu Tyr Gln Leu Glu Asn Tyr Cys Asn
            100                 105

<210> SEQ ID NO 9
<211> LENGTH: 31
<212> TYPE: PRT
<213> ORGANISM: Homo sapiens

<400> SEQUENCE: 9

Thr Tyr Glu Ile Ala Pro Val Phe Val Leu Leu Glu Tyr Val Thr Leu
```

```
1               5                  10                 15

Lys Lys Met Arg Glu Ile Ile Gly Trp Pro Gly Gly Ser Gly Asp
            20                 25                 30

<210> SEQ ID NO 10
<211> LENGTH: 20
<212> TYPE: PRT
<213> ORGANISM: Homo sapiens

<400> SEQUENCE: 10

Ala Ala Leu Gly Ile Gly Thr Asp Ser Val Ile Leu Ile Lys Cys Asp
1               5                  10                 15

Glu Arg Gly Lys
            20

<210> SEQ ID NO 11
<211> LENGTH: 35
<212> TYPE: PRT
<213> ORGANISM: Homo sapiens

<400> SEQUENCE: 11

Val Pro Pro Ser Leu Arg Thr Leu Glu Asp Asn Glu Glu Arg Met Ser
1               5                  10                 15

Arg Leu Ser Lys Val Ala Pro Val Ile Lys Ala Arg Met Met Glu Tyr
            20                 25                 30

Gly Thr Thr
        35

<210> SEQ ID NO 12
<211> LENGTH: 306
<212> TYPE: PRT
<213> ORGANISM: Mus musculus

<400> SEQUENCE: 12

Met Ala Cys Asn Cys Gln Leu Met Gln Asp Thr Pro Leu Leu Lys Phe
1               5                  10                 15

Pro Cys Pro Arg Leu Ile Leu Leu Phe Val Leu Leu Ile Arg Leu Ser
            20                 25                 30

Gln Val Ser Ser Asp Val Asp Glu Gln Leu Ser Lys Ser Val Lys Asp
        35                 40                 45

Lys Val Leu Leu Pro Cys Arg Tyr Asn Ser Pro His Glu Asp Glu Ser
    50                 55                 60

Glu Asp Arg Ile Tyr Trp Gln Lys His Asp Lys Val Val Leu Ser Val
65                  70                 75                  80

Ile Ala Gly Lys Leu Lys Val Trp Pro Glu Tyr Lys Asn Arg Thr Leu
                85                 90                 95

Tyr Asp Asn Thr Thr Tyr Ser Leu Ile Ile Leu Gly Leu Val Leu Ser
            100                105                110

Asp Arg Gly Thr Tyr Ser Cys Val Val Gln Lys Lys Glu Arg Gly Thr
        115                120                125

Tyr Glu Val Lys His Leu Ala Leu Val Lys Leu Ser Ile Lys Ala Asp
    130                135                140

Phe Ser Thr Pro Asn Ile Thr Glu Ser Gly Asn Pro Ser Ala Asp Thr
145                 150                155                 160

Lys Arg Ile Thr Cys Phe Ala Ser Gly Gly Phe Pro Lys Pro Arg Phe
                165                170                175

Ser Trp Leu Glu Asn Gly Arg Glu Leu Pro Gly Ile Asn Thr Thr Ile
            180                185                190
```

-continued

```
Ser Gln Asp Pro Glu Ser Glu Leu Tyr Thr Ile Ser Ser Gln Leu Asp
        195                 200                 205
Phe Asn Thr Thr Arg Asn His Thr Ile Lys Cys Leu Ile Lys Tyr Gly
210                 215                 220
Asp Ala His Val Ser Glu Asp Phe Thr Trp Glu Lys Pro Pro Glu Asp
225                 230                 235                 240
Pro Pro Asp Ser Lys Asn Thr Leu Val Leu Phe Gly Ala Gly Phe Gly
                245                 250                 255
Ala Val Ile Thr Val Val Ile Val Val Ile Ile Lys Cys Phe Cys
                260                 265                 270
Lys His Arg Ser Cys Phe Arg Arg Asn Glu Ala Ser Arg Glu Thr Asn
                275                 280                 285
Asn Ser Leu Thr Phe Gly Pro Glu Glu Ala Leu Ala Glu Gln Thr Val
                290                 295                 300
Phe Leu
305

<210> SEQ ID NO 13
<211> LENGTH: 223
<212> TYPE: PRT
<213> ORGANISM: Mus musculus

<400> SEQUENCE: 13

Met Ala Cys Leu Gly Leu Arg Arg Tyr Lys Ala Gln Leu Gln Leu Pro
1               5                   10                  15
Ser Arg Thr Trp Pro Phe Val Ala Leu Leu Thr Leu Leu Phe Ile Pro
                20                  25                  30
Val Phe Ser Glu Ala Ile Gln Val Thr Gln Pro Ser Val Val Leu Ala
                35                  40                  45
Ser Ser His Gly Val Ala Ser Phe Pro Cys Glu Tyr Ser Pro Ser His
                50                  55                  60
Asn Thr Asp Glu Val Arg Val Thr Val Leu Arg Gln Thr Asn Asp Gln
65                  70                  75                  80
Met Thr Glu Val Cys Ala Thr Thr Phe Thr Glu Lys Asn Thr Val Gly
                85                  90                  95
Phe Leu Asp Tyr Pro Phe Cys Ser Gly Thr Phe Asn Glu Ser Arg Val
                100                 105                 110
Asn Leu Thr Ile Gln Gly Leu Arg Ala Val Asp Thr Gly Leu Tyr Leu
                115                 120                 125
Cys Lys Val Glu Leu Met Tyr Pro Pro Pro Tyr Phe Val Gly Met Gly
                130                 135                 140
Asn Gly Thr Gln Ile Tyr Val Ile Asp Pro Glu Pro Cys Pro Asp Ser
145                 150                 155                 160
Asp Phe Leu Leu Trp Ile Leu Val Ala Val Ser Leu Gly Leu Phe Phe
                165                 170                 175
Tyr Ser Phe Leu Val Thr Ala Val Ser Leu Ser Lys Met Leu Lys Lys
                180                 185                 190
Arg Ser Pro Leu Thr Thr Gly Val Tyr Val Lys Met Pro Pro Thr Glu
                195                 200                 205
Pro Glu Cys Glu Lys Gln Phe Gln Pro Tyr Phe Ile Pro Ile Asn
                210                 215                 220

<210> SEQ ID NO 14
<211> LENGTH: 417
<212> TYPE: PRT
<213> ORGANISM: Homo sapiens
```

```
<400> SEQUENCE: 14

Met Lys Thr Glu Arg Pro Arg Pro Asn Thr Phe Ile Ile Arg Cys Leu
1               5                   10                  15

Gln Trp Thr Thr Val Ile Glu Arg Thr Phe His Val Glu Thr Pro Glu
            20                  25                  30

Glu Arg Glu Glu Trp Thr Thr Ala Ile Gln Thr Val Ala Asp Gly Leu
        35                  40                  45

Lys Lys Gln Glu Glu Glu Met Asp Phe Arg Ser Gly Ser Pro Ser
50                  55                  60

Asp Asn Ser Gly Ala Glu Glu Met Glu Val Ser Leu Ala Lys Pro Lys
65                  70                  75                  80

His Arg Val Thr Met Asn Glu Phe Glu Tyr Leu Lys Leu Leu Gly Lys
                85                  90                  95

Gly Thr Phe Gly Lys Val Ile Leu Val Lys Glu Lys Ala Thr Ala Tyr
            100                 105                 110

Tyr Ala Met Lys Ile Leu Lys Lys Glu Val Ile Val Ala Lys Asp Glu
        115                 120                 125

Val Ala His Thr Leu Thr Glu Asn Arg Val Gln Gln Asn Ser Arg His
    130                 135                 140

Pro Phe Leu Thr Arg Leu Lys Tyr Ser Phe Gln Thr His Asp Arg Leu
145                 150                 155                 160

Cys Phe Val Met Glu Tyr Ala Asn Gly Gly Glu Leu Phe Phe His Leu
                165                 170                 175

Ser Arg Glu Arg Val Phe Ala Glu Asp Arg Ala Arg Phe Tyr Gly Ala
            180                 185                 190

Glu Ile Val Ser Ala Leu Asp Tyr Leu His Ser Glu Lys Asn Val Val
        195                 200                 205

Tyr Arg Asp Leu Lys Leu Glu Asn Leu Met Leu Asp Lys Asp Gly His
    210                 215                 220

Ile Lys Ile Thr Asp Phe Gly Leu Cys Lys Glu Gly Ile Lys Asp Gly
225                 230                 235                 240

Ala Thr Met Lys Thr Phe Cys Gly Thr Pro Glu Tyr Leu Ala Pro Glu
                245                 250                 255

Val Leu Glu Asp Asn Asp Tyr Gly Arg Ala Val Asp Trp Trp Gly Leu
            260                 265                 270

Gly Val Val Met Tyr Glu Met Met Cys Gly Arg Leu Pro Phe Tyr Asn
        275                 280                 285

Gln Asp His Glu Lys Leu Phe Glu Leu Ile Leu Met Glu Glu Ile Arg
    290                 295                 300

Phe Pro Arg Thr Leu Gly Pro Glu Ala Lys Ser Leu Leu Ser Gly Leu
305                 310                 315                 320

Leu Lys Lys Asp Pro Lys Gln Arg Leu Gly Gly Gly Ser Glu Asp Ala
                325                 330                 335

Lys Glu Ile Met Gln His Arg Phe Phe Thr Gly Ile Val Trp Gln His
            340                 345                 350

Val Tyr Glu Lys Lys Leu Ser Pro Pro Phe Lys Pro Gln Val Thr Ser
        355                 360                 365

Glu Thr Asp Thr Arg Tyr Phe Asp Glu Glu Phe Thr Ala Gln Met Ile
    370                 375                 380

Thr Ile Thr Pro Pro Asp Gln Asp Ser Met Glu Cys Val Asp Ser
385                 390                 395                 400

Glu Arg Arg Pro His Phe Pro Gln Phe Ser Tyr Ser Pro Ser Ala Thr
                405                 410                 415
```

Ala

<210> SEQ ID NO 15
<211> LENGTH: 424
<212> TYPE: PRT
<213> ORGANISM: Homo sapiens

<400> SEQUENCE: 15

Met Ser Asp Ser Lys Cys Asp Ser Gln Phe Tyr Ser Val Gln Val Ala
1               5                   10                  15

Asp Ser Thr Phe Thr Val Leu Lys Arg Tyr Gln Gln Leu Lys Pro Ile
            20                  25                  30

Gly Ser Gly Ala Gln Gly Ile Val Cys Ala Ala Phe Asp Thr Val Leu
        35                  40                  45

Gly Ile Asn Val Ala Val Lys Lys Leu Ser Arg Pro Phe Gln Asn Gln
    50                  55                  60

Thr His Ala Lys Arg Ala Tyr Arg Glu Leu Val Leu Leu Lys Cys Val
65                  70                  75                  80

Asn His Lys Asn Ile Ile Ser Leu Leu Asn Val Phe Thr Pro Gln Lys
                85                  90                  95

Thr Leu Glu Glu Phe Gln Asp Val Tyr Leu Val Met Glu Leu Met Asp
            100                 105                 110

Ala Asn Leu Cys Gln Val Ile His Met Glu Leu Asp His Glu Arg Met
        115                 120                 125

Ser Tyr Leu Leu Tyr Gln Met Leu Cys Gly Ile Lys His Leu His Ser
    130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Cys Thr Asn Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Ile
        195                 200                 205

Trp Ser Val Gly Cys Ile Met Gly Glu Leu Val Lys Gly Cys Val Ile
    210                 215                 220

Phe Gln Gly Thr Asp His Ile Asp Gln Trp Asn Lys Val Ile Glu Gln
225                 230                 235                 240

Leu Gly Thr Pro Ser Ala Glu Phe Met Lys Lys Leu Gln Pro Thr Val
                245                 250                 255

Arg Asn Tyr Val Glu Asn Arg Pro Lys Tyr Pro Gly Ile Lys Phe Glu
            260                 265                 270

Glu Leu Phe Pro Asp Trp Ile Phe Pro Ser Glu Ser Glu Arg Asp Lys
        275                 280                 285

Ile Lys Thr Ser Gln Ala Arg Asp Leu Leu Ser Lys Met Leu Val Ile
    290                 295                 300

Asp Pro Asp Lys Arg Ile Ser Val Asp Glu Ala Leu Arg His Pro Tyr
305                 310                 315                 320

Ile Thr Val Trp Tyr Asp Pro Ala Glu Ala Glu Ala Pro Pro Pro Gln
                325                 330                 335

Ile Tyr Asp Ala Gln Leu Glu Glu Arg Glu His Ala Ile Glu Glu Trp
            340                 345                 350

Lys Glu Leu Ile Tyr Lys Glu Val Met Asp Trp Glu Glu Arg Ser Lys
        355                 360                 365

Asn Gly Val Val Lys Asp Gln Pro Ser Asp Ala Ala Val Ser Ser Asn

```
                    370                 375                 380
Ala Thr Pro Ser Gln Ser Ser Ile Asn Asp Ile Ser Ser Met Ser
385                 390                 395                 400

Thr Glu Gln Thr Leu Ala Ser Asp Thr Asp Ser Ser Leu Asp Ala Ser
                    405                 410                 415

Thr Gly Pro Leu Glu Gly Cys Arg
                420

<210> SEQ ID NO 16
<211> LENGTH: 278
<212> TYPE: PRT
<213> ORGANISM: Homo sapiens

<400> SEQUENCE: 16

Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Met Ser
                20                  25                  30

Trp Asp Thr Gly Tyr Lys Met Asp Tyr Pro Glu Met Gly Leu Cys Ile
            35                  40                  45

Ile Ile Asn Asn Lys Asn Phe His Lys Ser Thr Gly Met Thr Ser Arg
        50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95

Val Glu Leu Met Arg Asp Val Ser Lys Glu Asp His Ser Lys Arg Ser
                100                 105                 110

Ser Phe Val Cys Val Leu Leu Ser His Gly Glu Glu Gly Ile Ile Phe
            115                 120                 125

Gly Thr Asn Gly Pro Val Asp Leu Lys Lys Ile Thr Asn Phe Phe Arg
        130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Asp Asp Met Ala Cys His Lys Ile Pro Val Asp Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
            260                 265                 270

Leu Tyr Phe Tyr His Leu
        275

<210> SEQ ID NO 17
<211> LENGTH: 80
<212> TYPE: DNA
<213> ORGANISM: Artificial Sequence
<220> FEATURE:
<223> OTHER INFORMATION: Synthetic construct
```

```
<400> SEQUENCE: 17
ccggatatcg ccaccatgga gacagacaca ctcctgctat gggtactgct gctctgggtt    60
ccaggttcca ctggtgacca                                                80

<210> SEQ ID NO 18
<211> LENGTH: 23
<212> TYPE: DNA
<213> ORGANISM: Artificial Sequence
<220> FEATURE:
<223> OTHER INFORMATION: Synthetic construct

<400> SEQUENCE: 18
tgctgaaggg acctttacca gtg                                            23

<210> SEQ ID NO 19
<211> LENGTH: 96
<212> TYPE: DNA
<213> ORGANISM: Artificial Sequence
<220> FEATURE:
<223> OTHER INFORMATION: Synthetic construct

<400> SEQUENCE: 19
ccggatatcg ccaccatgga gacagacaca ctcctgctat gggtactgct gctctgggtt    60
ccaggttcca ctggtgaccc cagcgagacc gtcacc                              96

<210> SEQ ID NO 20
<211> LENGTH: 37
<212> TYPE: DNA
<213> ORGANISM: Artificial Sequence
<220> FEATURE:
<223> OTHER INFORMATION: Synthetic construct

<400> SEQUENCE: 20
cgcggatccc tatcatttac caggagagtg ggagagg                             37

<210> SEQ ID NO 21
<211> LENGTH: 103
<212> TYPE: DNA
<213> ORGANISM: Artificial Sequence
<220> FEATURE:
<223> OTHER INFORMATION: Synthetic construct

<400> SEQUENCE: 21
ccggatatcg ccaccatgga gacagacaca ctcctgctat gggtactgct gctctgggtt    60
ccaggttcca ctggtgacca tgctgaaggg acctttacca gtg                     103

<210> SEQ ID NO 22
<211> LENGTH: 37
<212> TYPE: DNA
<213> ORGANISM: Artificial Sequence
<220> FEATURE:
<223> OTHER INFORMATION: Synthetic construct

<400> SEQUENCE: 22
cgcggatccc tatcatttac caggagagtg ggagagg                             37

<210> SEQ ID NO 23
<211> LENGTH: 96
<212> TYPE: DNA
<213> ORGANISM: Artificial Sequence
<220> FEATURE:
<223> OTHER INFORMATION: Synthetic construct

<400> SEQUENCE: 23
```

```
ccggatatcg ccaccatgga gacagacaca ctcctgctat gggtactgct gctctgggtt      60
ccaggttcca ctggtgaccc cagcgagacc gtcacc                                96

<210> SEQ ID NO 24
<211> LENGTH: 37
<212> TYPE: DNA
<213> ORGANISM: Artificial Sequence
<220> FEATURE:
<223> OTHER INFORMATION: Synthetic construct

<400> SEQUENCE: 24
cgcggatccc tatcatttac caggagagtg ggagagg                               37

<210> SEQ ID NO 25
<211> LENGTH: 36
<212> TYPE: DNA
<213> ORGANISM: Artificial Sequence
<220> FEATURE:
<223> OTHER INFORMATION: Synthetic construct

<400> SEQUENCE: 25
aaggatatcg atcgcaaatg ttgtgtcgag tgccca                                36

<210> SEQ ID NO 26
<211> LENGTH: 32
<212> TYPE: DNA
<213> ORGANISM: Artificial Sequence
<220> FEATURE:
<223> OTHER INFORMATION: Synthetic construct

<400> SEQUENCE: 26
cgtaagcttc atttacccgg agacagggag ag                                    32
```

COMPOSITION AND METHOD FOR PREVENTION AND TREATMENT OF TYPE I DIABETES

This application is a National Phase entry of PCT/CA2006/001263, filed Aug. 4, 2006, which claims the benefit of U.S. Provisional Patent Application No. 60/595,803, filed Aug. 6, 2005, which are herein incorporated by reference.

INCORPORATION OF SEQUENCE LISTING

A computer readable form of the Sequence Listing "12960-5_SequenceListing.txt" (24,735 bytes), submitted via EFS-WEB and created on Dec. 21, 2010, is herein incorporated by reference.

FIELD OF THE INVENTION

The invention provides a composition and method for prevention and treatment of type I diabetes. In particular, the invention provides a composition and method for the treatment of type I diabetes in mammals where the composition comprises GLP-1 or Ex4 fusion proteins and a plasmid encoding one or more proteins that promote islet beta-cell regeneration and decrease islet beta-cell autoimmunity.

BACKGROUND OF THE INVENTION

Diabetes is one of the leading causes of death by disease worldwide. Type I diabetes, is a major form of the disease that typically develops at a young age and results from autoimmune destruction of islet beta-cells with consequent insulin deficiency and dependence on exogenous insulin treatment. Insulin therapy is the major intervention for the treatment of type I diabetes, however, insulin not a cure as it is not always possible to maintain blood glucose levels within a narrow physiological range using insulin and it does not prevent the progression of the disease and severe diabetic complications that eventually arise. Pancreatic islet transplantation is also an effective therapy (29) but is limited largely by the limited resources of human islets. In addition, immune-suppressors need to be used for life in the islets-transplanted patients.

Apoptosis is the main cause of the death of beta-cells in type I diabetes. Under normal conditions, maintenance of beta-cell mass is a dynamic process, undergoing both increases and decreases to maintain glucose levels within a narrow physiological range (1; 2). In subjects with obesity and insulin resistance associated diabetes, diabetes occurs only when the beta-cells lose their compensatory capacity. Diabetes does not occur even in the presence of insulin resistance if the beta-cell mass is maintained or enhanced. In type I diabetes, beta-cell apoptosis occurs as a result of autoimmune destruction involving T cell infiltration of the islets of Langerhans (5-7). The progressive destruction of the pancreatic beta-cells is largely due to lymphocytic infiltration of the islet, resulting in insulin deficiency. IL-1beta, TNF-alpha and IFN-gamma are released by macrophages and T cells during this autoimmune response and are important mediators of beta-cell destruction (5; 23; 24) via a mechanism that involves apoptosis and necrosis (24).

GLP-1 is a major physiological insulinotropic hormone which is secreted from the enteroendocrine L cells of the intestinal tract in response to nutrient ingestion (12-14). GLP-1 enhances pancreatic islet beta-cell neogenesis/proliferation and inhibits beta-cell apoptosis; in a glucose-dependent fashion (15; 16). GLP-1 also augments insulin secretion and lowers blood glucose in rodents as well as in humans in both type I diabetes (17; 18) and type II diabetes (19; 20). Recent studies have demonstrated that in insulin-secreting beta-cells, the apoptosis and necrosis induced by cytokines could be significantly blocked by glucagon-like peptide-1 (GLP-1) or exendin-4 (Ex4), a long-acting potent agonist of the GLP-1 receptor (24; 25). In vivo studies have shown that treatment with GLP-1/Ex4, stimulated beta-cell neogenesis in streptozotocin (STZ)-treated newborn rats resulting in persistently improved glucose homeostasis at an adult age (26). In type I diabetes patients, treatment with Ex4 normalized postcibal glycemic excursions (18). It is believed that the mechanism by which GLP-1 modulates beta-cell mass involves primarily 1) enhancement of β-cell proliferation, 2) inhibition of apoptosis of B-cells and 3) beta-cell neogenesis (13; 27; 28).

The GLP-1 receptor (GLP-1R) is a G-protein coupled receptor (GPCR) that is expressed mainly by pancreatic beta-cells and to some extent by cells of other tissues (lungs, heart, kidney, GI tract and brain), and is coupled to the cyclic AMP (CAMP) second messenger pathway (13; 21). Activation of other protein kinases including Akt (protein kinase B) (3; 13; 22) is found to be important in mediating GLP-1 action in promoting beta-cell growth and inhibiting apoptosis. In animals models of type II diabetes, it has been recently demonstrated that treatment of GLP-1 or exendin-4 (Ex4) prevented onset of diabetes (3; 4) by enhancing beta-cell growth and inhibiting apoptosis (3; 22). GLP-1 has many attractive biological actions, and demonstrated clinical efficacy in type II diabetes (9). Beta-cell replication and neogenesis are predominant mechanisms underlying beta-cell mass expansion. In addition, prevention of beta-cell apoptosis is important. GLP-1 has been found useful in the treatment of type II diabetes, which is consistent with its beneficial effects on beta-cell survival, function and growth. It has been demonstrated that expansion of beta-cell mass by treatment with glucagon-like peptide-1 (GLP-1) prevented the onset of diabetes in animal models predisposed to type II diabetes (3; 4). U.S. Pat. No. 6,899,883 and U.S. Pat. No. 6,989,148 disclose methods of treating type I diabetes using insulin and glucagon-like peptide 1(7-37) or glucagon-like peptide 1(7-36) amide.

The major obstacle in treating patients with native GLP-1 is its short circulating half-life ($t_{1/2}$<2 min) that results mainly from rapid enzymatic inactivation by dipeptidyl-peptidase IV (DPP-IV) (30; 31), and/or renal clearance (32). Therefore, continuous subcutaneous infusion by pump is necessary to maintain GLP-1 action in vivo (33). Though DPPIV inhibitor can also increase the half-life of GLP-1 and are being tested in clinical trials. However, this approach lacks specificity, as DPPIV also inactivates several other peptide hormones and some chemokines (9), and its inhibition may lead to adverse reactions. In this respect, significant efforts have been made to develop pharmaceutical long-acting degradation-resistant GLP-1 mimetic peptides. Human GLP-1 analogues with amino acid substitutions (34-36) and/or N-terminal modifications including fatty acylated (37; 38) and N-acetylated (38) modifications exhibit significantly prolonged circulating $t_{1/2}$, and potently reduce glycemic excursion in diabetic subjects (37). Ex4, a reptilian peptide with high sequence homology to mammalian GLP-1 is a potent GLP-1R agonist (39). Furthermore, albumin protein-conjugated GLP-1 also has the anti-diabetic and other beneficial activities of GLP-1 along with a prolonged half-life (40).

It is likely, however, that in some patients derivatives of GLP-1 will eventually be recognized and neutralized by humoral immunity, as observed with various peptides such as human growth hormone or insulin (41; 42) and, indeed, also Ex4 (39). This can occur either because the protein is foreign (i.e. Ex4), or because it is administered with a vehicle or by a route that promotes immunity. This is initiated when B lymphocytes that have a reactive immunoglobulin receptor (B-cell receptor [BCR]) bind to the hormone. However, there is evidence that B-cell stimulation can be prevented by co-ligating inhibitory receptors. B-cell stimulation is blocked when the BCR is cross-linked with FcγRIIB receptors that bear cytoplasmic immunoreceptor tyrosine-based inhibitory motifs (ITIM) (43-47). It is thought that B cell reactivity to GLP-1 will be prevented or diminished when this peptide is fused to an Fc segment, through binding of this Fc segment to the FcγRIIB receptor. This is consistent with the tolerogenic effects of IgG carrier proteins, as demonstrated extensively in many studies (48). A second important consideration is that peptide drugs can give rise to dangerous anaphylactic reactions. For instance, fatal anaphylaxis in nonobese diabetic (NOD) mice has been described after repeated subcutaneous insulin peptide B:9-23 immunizations (49). These anaphylactic reactions result from the production of IgE antibodies against the therapeutic peptide, resulting in classic type I hypersensitivity reactions. A recent study (50) suggests that this anaphylactic response can be blocked by fusing the allergen with IgG-Fc that bind to FCγRIIB of mast cells or basophils and prevents degranulation. Furthermore, administration of GLP-1/Ex4, combined with immunosuppression by polyclonal anti-T cell antibody, induced complete remission in 88% of overtly diabetic NOD mice (8). However, limitations of this strategy are 1) immunity to Ex4 which has >45% variation of amino acid sequence compared to native GLP-1 (9) and 2) systemic suppression of immunological responses by an anti-T-cell antibody that may lead to adverse immunologic effects (10). Because autoimmunity is persistent in type I diabetes subjects, control of autoimmunity with immunosuppression (preferably specifically directed against the autoaggressive T cells) is necessary for the replacement of islet cells and definitive treatment of this disease.

Gene therapy has been attempted in animal models of diabetes. For example, gene therapy has been directed at the systemic delivery of regulatory cytokines (e.g., IL-4, IL-10, TGF-beta-1) (54; 55), or at modification of islet cells ex vivo with some of these genes prior to transplantation (56). Alternatively, investigators have transfected islet cells ex vivo with genes such as bcl-2 that prevent apoptosis (56-58). The introduction of genes into transplanted islets has been limited by incomplete protection against anti-islet immunity, and the relatively short period of expression of some vectors (59). In addition, gene therapy to deliver insulin (or insulin analogues) in liver, muscle or other tissues has been accomplished, although physiological regulation of blood glucose levels has not been achieved and is a major limitation (62; 63). An alternative involves delivery of a gene(s) (e.g., PDX-1) in vivo to induce islet-cell differentiation of liver cells (64), but initial reports of success have been difficult to duplicate. Another important factor is that current proposed therapies fail to control autoimmunity effectively and as long as the autoimmune response of type I diabetic subjects is not controlled, new islets whether transplanted or produced by regeneration will be rejected. Indeed, many potential gene-based approaches have been proposed over the years, but none appears readily applicable to humans. These therapies have almost all been based on viral-vectored gene transfer which has limitations, particularly in terms of pathogenicity and immunogenicity and thus do not provide an effective and safe therapeutic method. For example, U.S. Pat. No. 6,991,792 discloses a method for delaying onset of type 1 diabetes mellitus using a vaccine comprising a recombinant vaccinia virus incorporated with a gene for coding glutamic acid decarboxylase.

Many forms of immunotherapy ameliorate diabetes in NOD mice (53), although most are effective only if initiated prior to the onset of the disease. Unfortunately, most patients initially present with diabetes. More recently, CD3 monoclonal antibody (mAb) therapy was found effective after the onset of disease in NOD mice, and acts by inducing regulatory T cells (Tr) (67). However, recent clinical trials suggest that CD3 mAb therapy by itself delays beta-cell loss, but cannot return patients to normoglycemia (10; 68). This is presumably because newly diabetic patients have a limited number of residual islet beta-cells, which are not sufficiently protected or replenished by this treatment. Another limitation is that most forms of immunotherapy (as in the case of CD3) are not specific to the autoaggressive T cells, and affect many other immune responses, possibly causing undesirable effects. Notably, administration of ChAglyCD3 (a humanized CD3 mAb) was frequently associated with a cytokine release syndrome and transient Epstein-Barr viral mononucleosis (10). The long-term effects and safety of this method needs to be further assessed.

Thus, there is a need to develop effective treatment strategies that target the molecular mechanisms underlying type I diabetes rather than its consequences.

SUMMARY OF THE INVENTION

The present invention is a composition and method for the prevention or treatment of type I diabetes. The composition and method of the invention promote beta-cell growth and inhibit apoptosis, induce immunological tolerance and block autoimmunity. The composition of the invention comprises a fusion protein and an autoimmune suppressor. These are provided together in a single composition for the effective prevention or treatment of type I diabetes in mammals.

In aspects, the fusion protein comprises a GLP-1 molecule or its variant or fragments thereof fused with IgG heavy chain constant (Fc) regions. The autoimmune suppressor comprises at least one target antigenic epitope that effectively decrease autoimmunity, such that the pancreatic islet cells are not destroyed. In aspects, the at least one target antigenic epitope comprises at least one of pre-proinsulin and GAD65. The autoimmune suppressor may further comprise a mutant B7-1 peptide (CD80).

According to an aspect of the present invention is composition to promote IgG-Fc receptor-dependent immune inhibition, the composition comprising a GLP-1 fusion protein and an autoimmune suppressor.

According to another aspect of the invention is a composition comprising a fusion protein selected from GLP-1/IgG and Ex4/IgG; and a vector encoding preproinsulin and GAD65.

In aspects of the invention the composition additionally comprises a sequence encoding a mutant B7-1 peptide.

According to an aspect of the present invention is a method of preventing or treating type I diabetes in a subject in need thereof, comprising administering to the subject an effective amount of a composition that increases beta-cell proliferation and/or reduces beta-cell apoptosis in the subject.

According to an aspect of the present invention is the use of the composition of the invention for the preparation of a medicament for the prevention or treatment of type I diabetes in a subject.

According to an aspect of the present invention is a method of isolating a Tr cell, said method comprising:

administering to a subject the composition of the invention;
collecting the spleen cells of said subject;
preparing a suspension of said spleen cells;
separating the CD4+ cells from said suspension; and
further separating the CD4+ cells using markers selected from the group consisting of B7.1+, Nrp1+, Foxp3 and LAP-TGF beta cells.

According to an aspect of the present invention is a composition wherein the increased proliferation and/or reduced apoptosis and suppressed beta-cell autoimmunity which provide increased beta-cell mass and function.

According to an aspect of the present invention is composition for the prevention or treatment of type I diabetes in a subject, said composition comprising a fusion protein selected from the group consisting of GLP-1/IgG or variant or fragment thereof and an Ex4/IgG or variant or fragment thereof; and an autoimmune suppressor for silencing an autoimmune response against islet beta cells.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which.

DETAILED DESCRIPTION OF THE INVENTION

Figure 1:
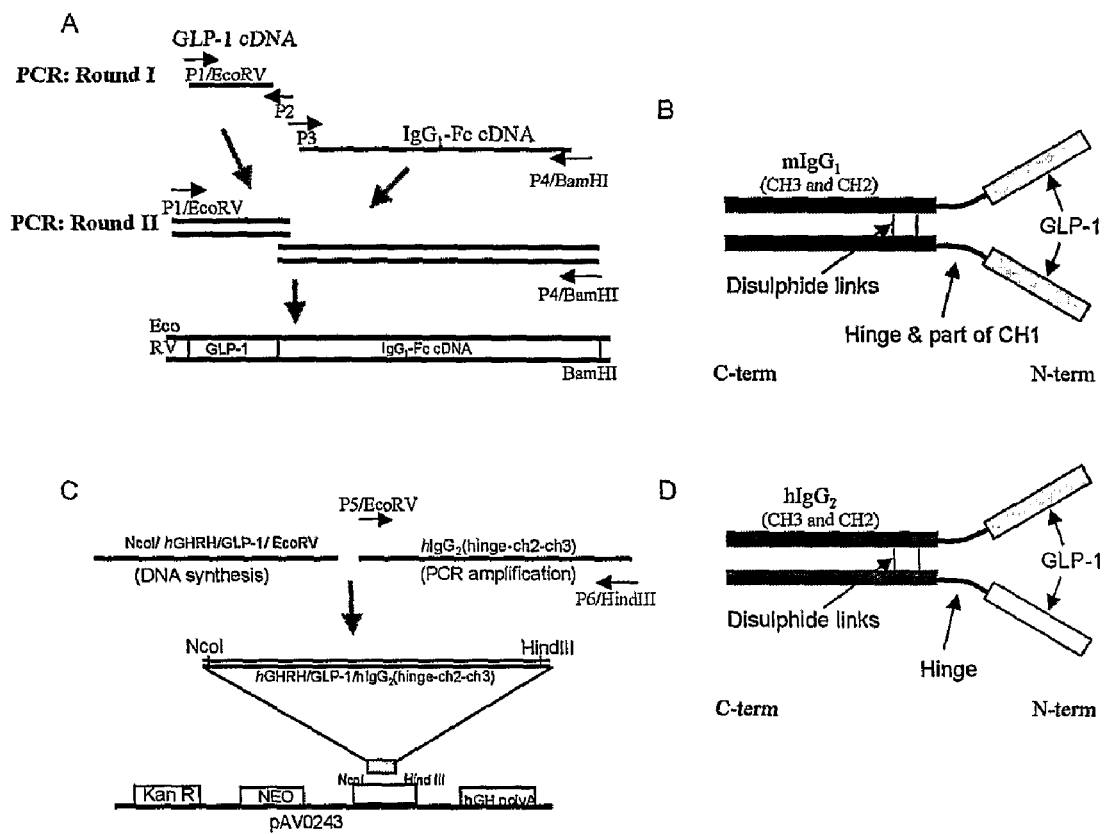
FIG. 1 shows the construction of GLP-1/IgG-Fc-encoding plasmid. 1A, a cDNA encoding a GLP-1/mIgG1-Fc fusion protein was inserted between the Bam HI and Eco RV sites of the vector. P1 to P4 represent the vectors used for amplifying the cDNA. A schematic representation of the secreted GLP-1/IgG-Fc fusion protein consisting of the active GLP-1 molecule (7-37) and the IgG-Fc encompassing the mouse IgG1 constant heavy-chain (part of CH1, hinge, CH2 and CH3) is shown in 1B. 1C, the cDNA encoding the fusion protein hGHRH/hGLP-1 was chemically synthesized, ligated to a PCR-amplified cDNA fragment encoding human IgG2 FC (hinge-ch2-ch3) and inserted into the NcoI and Hind III sites of the pAV0243 vector to generate GLP-1/hIgG-Fc/pAV0243. A schematic representation of the secretable GLP-1/hIgG-Fc fusion protein consisting of the active GLP-1 molecule (7-37) and the IgG-Fc encompassing the human IgG2 constant heavy-chain (hinge, CH2 and CH3) is shown in 1D. These proteins are secreted as homodimers upon expression. The cDNAs encoding a GLP-1A8G-IgG-Fc or Ex4/IgG-Fc fusion proteins were generated using site-directed mutagenesis. Similar strategy was used to generate a Ex4/IgG-Fc cDNA and cloned into pAV0243.

The invention provides for a composition and method of preventing and/or treating type I diabetes in a subject. The composition is administered to a subject in need thereof and increases beta-cell proliferation, reduces beta-cell apoptosis and controls immunity specifically with the endpoint of enhancement of beta-cell mass/function and insulin secretion. The composition comprises a GLP-1/IgG-Fc fusion protein or exendin-4-IgG-Fc fusion protein and a specific autoimmune suppressor. The autoimmune suppressor comprises at least one target antigenic epitope that effectively decrease autoimmunity, such that the pancreatic islet cells are not destroyed. In aspects, the at least one target antigenic epitope comprises at least one of pre-proinsulin and GAD65. The autoimmune suppressor may further comprise a negative regulatory protein such as for example a mutant B7-1 peptide (CD80).

The composition can be made to contain the various components thereof as the peptides/proteins or combination of peptides/proteins with a vector encoding for the remainder of the components. In other aspects, the components of the composition all are provided within suitable vectors as nucleic acid sequences.

In an embodiment, the autoimmune suppressor that targets an antigenic epitope may be encoded by a nucleotide sequence and may be provided in the composition as a DNA vaccine. The DNA vaccine comprises at least one plasmid having a nucleotide sequence which is expressed by the cellular machinery of the subject to be vaccinated. The nucleotide sequence of the plasmid encodes one or more antigenic peptides capable of inducing tolerance and decreasing autoimmune recognition. According to the invention, the plasmid encodes islet cell antigens and optionally a ligand for a negative regulatory protein. In aspects of the invention, the islet cell antigens are pre-proinsulin and GAD65. The negative regulatory protein is a ligand for a negative T cell regulatory protein is a B7-1wa peptide that binds to CTLA-4. The composition effectively increases beta cell proliferation or neogenesis, reduces beta cell apoptosis and decreases islet autoimmunity thereby providing prevention, remission and general treatment of type I diabetes in a subject.

In one embodiment, the fusion protein of the composition comprises active GLP-1 and IgG heavy chain constant regions (GLP-1/IgG-Fc). The construction of fusion proteins combining GLP-1 with an IgG-Fc molecule forms a new molecule that possess enhanced GLP-1 actions and advantages of the IgG-Fc molecule i.e. increased ligand avidity and immunological tolerance. The GLP-1 peptide in aspects is native or is DPP-IV (Dipeptidyl Peptidase IV) resistant. The IgG may be mouse or human. In aspects, a mouse IgG may be $IgG_1$. A human IgG may be selected from $IgG_1$, $IgG_2$, $IgG_3$ and $IgG_4$. The GLP-1 polypeptide may be human or mouse sequence as they are identical. The GLP-1 polypeptide may be a variant or fragment of the native sequence. The GLP-1 polypeptide may be GLP-1(7-37)OH or GLP-1(7-36)amide.

This invention also provides plasmid construction of a vector encoding a fusion protein consisting of the human GLP-1 (7-37) and mouse IgG-Fc using overlap PCR (Polymerase Chain Reaction) as illustrated (FIG. 1). The IgG-Fc region contains the $IgG_1$ constant heavy-chain (part of CH1, hinge, CH2 and CH3). Also demonstrated is a method to incorporate a leading sequence into a vector that allows the fusion protein to be expressed and secreted to an extracellular medium environment. As shown, an IgK secretion leader peptide sequence is fused with the GLP-1 sequence that directs the secretion of the synthesized peptide into the medium. This strategy ensures the generation of a GLP-1 fusion with an active histidine residue at the N-terminus of the fusion protein after cleavage of the secretion leader sequence peptide during the process of secretion. A schematic representation of the secreted GLP-1/IgG-Fc fusion protein is shown in FIG. 1. This approach is expected to 1) circumvent the short circulating half-life of GLP-1 since IgG-Fc fusion proteins are secreted as homodimers that possess longer circulating half-life and higher efficacy due to higher ligand avidity (78-80); 2) enhance the peptide potency since most GPCRs are pre-formed as dimers on the cell surface (81; 82); and 3) facilitate the purification, which can be achieved by one-step purification using Protein G sepharose (83).

Figure 2:
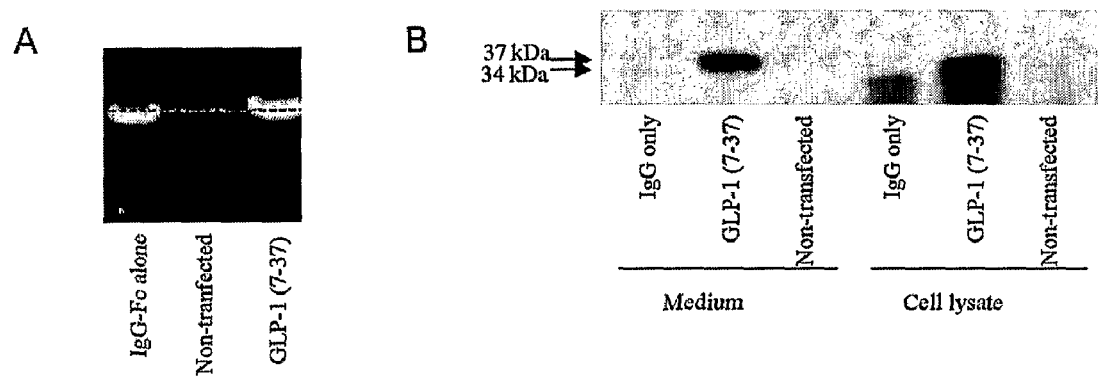
FIG. 2 shows the expression and detection of IgG-Fc fusion protein in COS-7 cells. COS-7 cells were transfected with the IgG-Fc fusion constructs and total RNA was isolated 48-h post transfection. 2A shows the RT-PCR products on a 1% agarose gel and visualized using ethidium bromide. 2B shows the fusion proteins purified using Protein G sepharose and resolved by SDS-PAGE and transferred to a nitrocellulose membrane. The membrane was probed with anti-mouse antibody (1:5000) and visualized by ECL.

Expression of the novel vectors of the fusion protein was demonstrated using a mammalian expression system. To assess the capacity of the vectors in terms of expression and secretion of the GLP-1/IgG-Fc fusion proteins, constructs were transiently transfected into COS-7 cells. Forty-eight hours after transfection, to evaluate the expression of the fusion constructs, total RNA from the transfected cells was prepared and expression was analyzed using RT-PCR. Transcripts for the GLP-1/IgG-Fc fusion constructs and IgG-Fc control constructs were detected using the gene specific primers (FIG. 2a). No transcripts were detected in non-transfected samples.

The lysates and medium from the transfected COS-7 cells were also analyzed for expression of the fusion proteins by Western blotting using anti-mouse antibodies. As shown in FIG. 2b, IgG-Fc fusion proteins were detected in both the medium and cell lysates. The fusion proteins could can be detected by RT-PCR (Reverse Transcription Polymerase Chain Reaction), western blotting, or and GLP-1 radio-immunoassay (RIA). Detection of the fusion proteins both in the conditioned media and the cell lysates indicates that the fusion proteins were synthesized and secreted from the mammalian cells.

Figure 3:
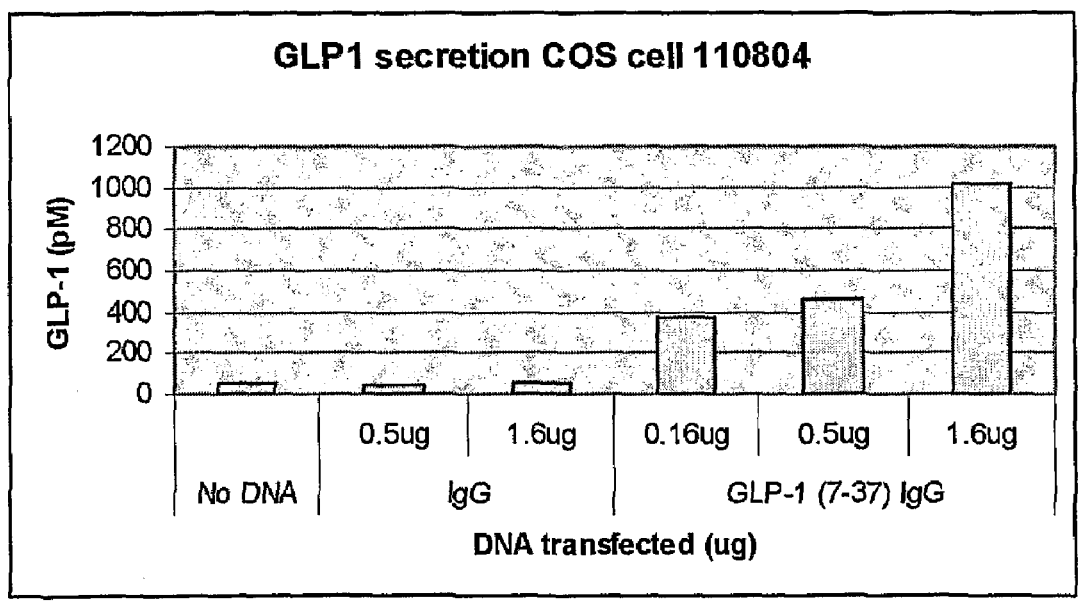
FIG. 3 is a graph showing the secretion of GLP-1 from transfected COS-7 cells. COS-7 cells were plated in 12-well plates and transfected with varying amounts of GLP-1/IgG-Fc or IgG-Fc only plasmids. The medium was collected 48-h post transfection and 150 μL of the medium was used to detect GLP-1 by RIA.
Figure 4A:
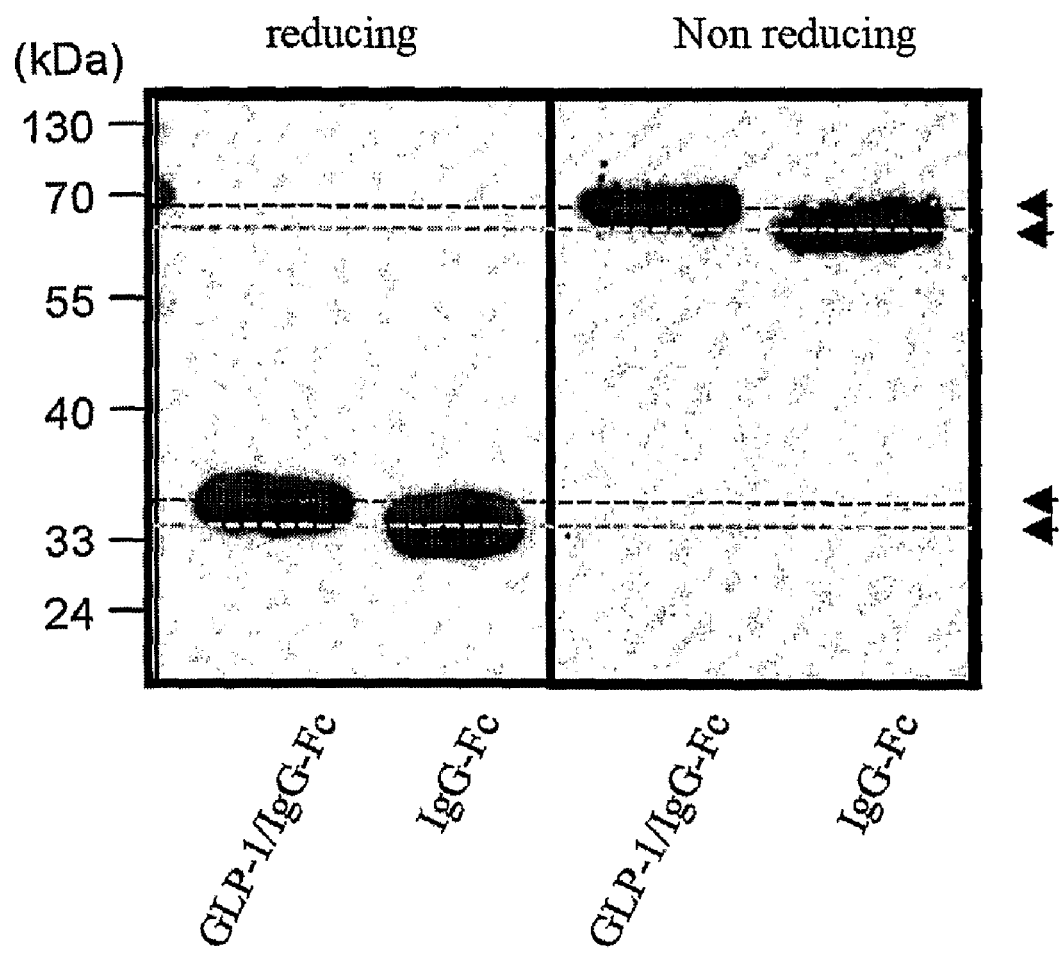
FIG. 4A shows large scale expression of IgG-Fc fusion proteins in COS-7 cells. COS-7 cells were plated in 150 mm dishes and transfected with 80 μg of DNA the following day. Forty-eight hours after transfection, the medium was collected and fusion proteins purified by incubating with 1 mL of Protein G Sepharose overnight. The beads were washed and the purified proteins were eluted by adding 1 mL of 0.1M glycine (pH 2.7). The elution was repeated and the fractions were pooled. 30 μL fractions were analyzed by SDS-PAGE under reducing or non-reducing conditions as indicated and staining with Coomassie Blue.

The identity of the GLP-1 fusion protein was further confirmed by a GLP-1 radioimmunoassay (RIA), which allows for detection of all forms of GLP-1. COS-7 cells were transiently transfected with increasing amounts of GLP-1/IgG-Fc or IgG-Fc-only plasmids and media were collected 48 hours following transfection. The medium was used in GLP-1 RIAs to detect total GLP-1. While no GLP-1 was detected in medium from non-transfected or IgG-Fc-only transfected COS-7 cells, GLP-1 was detected in a DNA-dose dependent manner in the medium collected from GLP-1/IgG-Fc-transfected cells (FIG. 3). One-step purification (83) from 50 ml culture medium (2-day static culture when seeding at ~1.25× $10^5$ cells/ml) using Protein G sepharose could yield ~300 microgram fusion as estimated by Coomassie Blue-stained SDS-PAGE of which detected a ~35 kDa or ~70 kDa (FIG. 4) band under reducing or non-reducing conditions respectively, indicating that bivalent GLP-1/IgG-Fc fusion protein exists in native conditions. The fusion proteins displayed capacity to stimulate insulin secretion in a glucose-dependent manner (FIG. 1D) and cAMP generation (FIG. 1E) in INS-1 cells.

Expression of the novel vectors of the fusion protein was demonstrated in a mammalian expression system or using a bacterial strain. The procedures for generation of mammalian cell clones and bacterial cell clones to generate the GLP-1/IgG-Fc fusion protein and its derivates are described in the examples below. The purification procedures are also disclosed and provide for an easy and fast one-step purification technique for purification GLP-1/IgG-Fc fusion protein and its derivates described in a practical scale of laboratory scale. This technique may also applies to purification of GLP-1/IgG-Fc fusion protein and its derivates described in a large scale such that for pharmaceutical purpose.

Using assay methods disclosed, the efficacy of fusion proteins GLP-1/IgG-Fc (its DPPIV resistant mutant form and Ex4-IgG-Fc) were tested and demonstrated. Examples are given including receptor binding assay, cAMP (Adenosine 3',5'-cyclic monophosphate) assay and insulin stimulation assay using beta-cells that have capacity to secret insulin under proper stimulatory conditions. Other assays may be also applied to study the beta-cell proliferation by the fusion proteins or to determine signaling cascade after activation of GLP-1 receptor by GLP-1/IgG-Fc fusion proteins its derivates described. These assays are proliferation assay (3H-thymidine incorporation), Akt kinase activity assay, MAPK assay and apoptotic assay using caspase-3 or other caspase-family members.

The techniques for in vivo expression of GLP-1/IgG-Fc molecules are also described. An example is given that the fusion proteins can be persistently expressed in vivo via intramuscular injection. The local electroporation technique is used because it greatly increases gene transfer that might be required in large animals and humans. However, one skilled in the art would understand the types of methods available to express the GLP/IgG-Fc molecules. In this study, the animals were monitored for bodyweight and fasting blood glucose weekly, and saphenous vein bleedings were collected prior to injection at 2 weeks and 12 weeks after the first injection, for measurement of fasting insulin and glucagon levels. Expression of the GLP-1/IgG-Fc protein was evaluated by measuring plasma levels of active GLP-1 using a GLP-1 Elisa kit (Linco). As shown, 2 weeks after the first injection, the plasma GLP-1 levels were significantly elevated in mice injected with GLP-1/IgG-Fc compared to those mice injected with IgG-Fc vectors. These elevated levels declined by 16 weeks post-injection, but were still higher than that of control mice (FIG. 8A).

Figure 9:
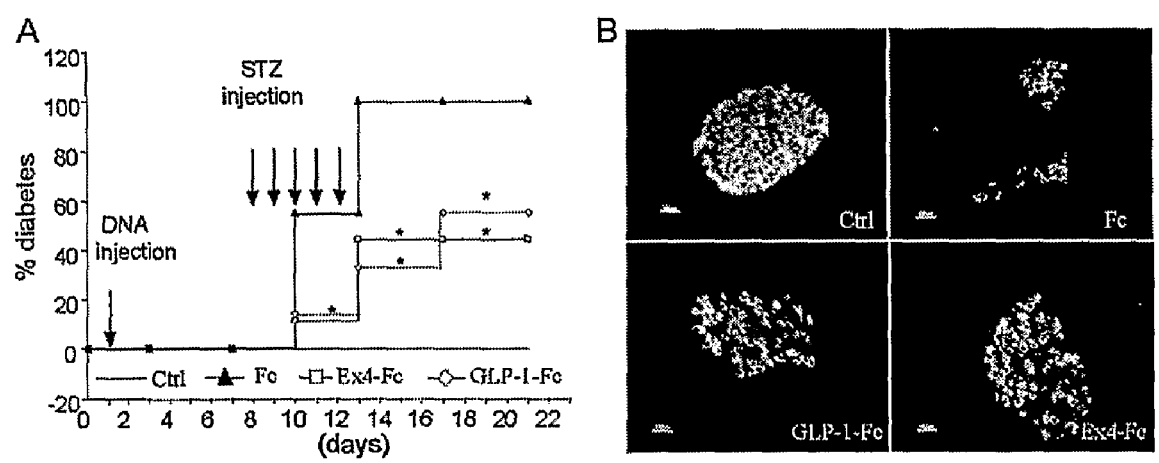
FIGS. 9A and 9B shows the effects of in vivo expression of GLP-1/IgG-Fc in insulin deficient type I diabetes model induced by streptozotocin. (9A) Vectors encoding GLP-1/IgG-Fc, Ex4/IgG-Fc or IgG-Fc (50 μg/mice) were intramuscularly injected into CD1 mice and gene transfer was enhanced by a local electroporation. Seven days after DNA injection, the mice were received a booster injection and on the same day received a daily injection of STZ (55 mg/kg, i.p.) for consecutive 5 days. The blood glucose of the IgG-Fc-control mice rose markedly, reaching diabetic levels (≧17 mM) a few days after STZ injection, but the GLP-1/IgG-Fc (or Ex4/IgG-Fc) mice were protected and displayed a low incidence of overt diabetes. (9B) Pancreatic histology studies were performed in pancreatic sections prepared as previously reported (Wang et al., Mol Biol Cell. 1998; 9(11):3057-3069). The beta-cells were immunostained for overnight incubation at 4° C. using guinea pig anti-insulin IgG (1:1,000, Dako). After incubated with biotinylated mouse anti-guinea pig IgG (1:1, 100) for 60 min at room temperature, Cy3-conjugated avidin (1:1, 1000, Jackson Labs) was added for additional 45 min incubation. The images were taken using a Ziess Laser Scanning Microscope (Model 510). Total beta-cell mass per pancreas was determined as the product of the total cross-sectional insulin positive-beta-cell area/total tissue area and the weight of the pancreas before fixation. As shown the destruction of islet beta-cells occurred in all groups of mice treated with STZ, but the extent of damage was found to be lower in GLP-1/IgG-Fc (or Ex4-IgG-Fc) mice. Infiltration of the islets by mononuclear cells (lymphocytes and/or macrophages) was observed in these mice (not shown). Interestingly, Ex4/IgG-Fc treatment yielded a result similar to GLP-1/IgG-Fc, even though Ex4/IgG-Fc is expected to resist DPPIV degradation. These findings indicate that expression of GLP-1/IgG-Fc (or Ex4/IgG-Fc) protected against the STZ-induced beta-cell damage in spite of the presence of islet inflammation (insulitis).

As an example of using GLP-1/IgG-Fc for prevention and treatment of type I diabetes, GLP-1/IgG-Fc and/or Ex4/IgG-Fc were delivered into the CD1 mice through gene transfer and enhanced by local electroporation. Seven days after DNA injection, the mice were received a booster injection and meanwhile received STZ (55 mg/kg, i.p.) daily for consecutive 5 days. The blood glucose of the IgG-Fc-control mice rose markedly, reaching diabetic levels ($\geqq 17$ mM) within a few days, but the GLP-1/IgG-Fc (or Ex4-Fc) mice were protected and displayed a low incidence of overt diabetes (FIG. 9). Pancreatic histological studies demonstrated that destruction of islet beta-cells occurred in both group mice, but the extent of damage was found to be lower in GLP-1/IgG-Fc (or Ex4-Fc) mice (FIG. 9), indicating the beta-cell protective effect of GLP-1/IgG-Fc (or Ex4/IgG-Fc). Infiltration of the islets by mononuclear cells (lymphocytes and/or macrophages) was observed in both groups of mice (not shown). Interestingly, Ex4-Fc treatment yielded a result similar to GLP-1/IgG-Fc, even though EX4-Fc is expected to resist DPPIV degradation. These findings indicate that expression of GLP-1/IgG-Fc (or Ex4-Fc) protected against the STZ-induced beta-cell damage in spite of the presence of islet inflammation (insulitis). The treatment of GLP-1/IgG-Fc or Ex-4/IgG-Fc most likely protected against streptozotocin-induced beta-cells damage via increased beta-cell proliferation, neogenesis and decreased beta-cell apoptosis (3).

Figure 8:
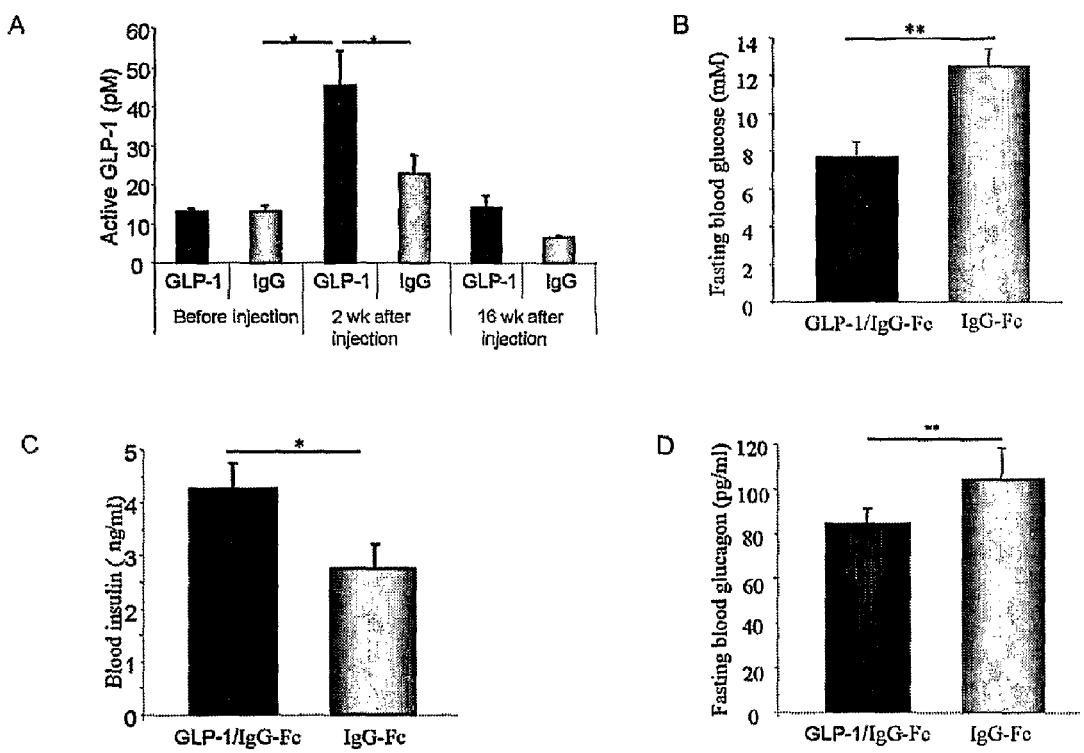
FIGS. 8A-D shows the effects of in vivo expression of GLP-1/IgG-Fc in type II diabetes model db/db mice. Db/db mice were intramuscularly injected with GLP-1/IgG-Fc and/or Ex4/IgG-Fc or IgG-Fc vectors at 4 and/or 6 weeks of age local electroporation was applied. Serum was collected before injection and 2, 12 and 16 weeks after injection. Active GLP-1 levels were determined using a GLP-1 Elisa kit (8A). Fasting blood glucose levels in the two groups of mice were measured 12-week after first injection (n=5-6, p<0.001) (8B). Their blood insulin (8C) and glucagon (8D) levels were measured using RIA at 12 weeks after overnight starvation.

GLP-1/IgG-Fc (or its derivatives or Ex4-IgG-Fc) improves insulin secretion by enhancing beta-cell mass and beta-cell function. Direct evidence of enhancement of beta-cell function and insulin secretion by treatment with GLP-1/IgG-Fc is demonstrated through administering the non-viral vectors encoding GLP-1/IgG-Fc molecule via gene transfer and a local electroporation to CD1 mice (a second injection is administered 2 weeks after the first injection). Diabetes occurred in those mice transfected with empty vector after induction of STZ, but the induction of diabetes by STZ was largely reduced in the mice treated with GLP-1/IgG-Fc or Ex4/IgG-Fc. Beta cell mass was found to be increased in the GLP-1/IgG-Fc/Ex4/IgG-Fc treated mice compared to the mice with mock treatment. GLP-1/IgG-Fc enhancement of beta-cell mass was also evident in db/db mice, when GLP-1/IgG-Fc was administered via gene therapy as described above to db/db mice (4 weeks of age, and a second injection is administered 2 weeks after the first injection). The db/db mouse genetically lacking leptin receptors, is a severe rodent model for type II diabetes (84). As shown, age-matched db/db mice treated with a GLP-1/IgG-Fc via the gene therapy approach exhibited normoglycemia at age of 16 weeks (12 weeks after injection). The control mice, however were hyperglycemic as determined by their fasting blood glucose (FBG) levels (FIG. 8). The GLP-1/IgG-Fc treated mice showed enhanced fasting insulin and reduced fasting glucagon (FIG. 8) levels. That enhancement of beta-cell mass and beta-cell function by treatment of GLP-1/IgG-Fc prevented the onset of diabetes in db/db mice expressing GLP-1/IgG-Fc is in a good agreement with our previous findings that daily Ex4 injection (i.p.) for two weeks prevented development of diabetes in db/db mice (3). The significance of the current therapeutic strategy is that two intramuscular injections of GLP-1/IgG-Fc vectors achieved similar effects to that of two weeks of daily intraperitoneal injections of Ex4. Enhancement of functional beta-cell mass by treatment of GLP-1/IgG-Fc is directly evident (FIG. 9).

Functional beta-cell mass is dynamic and is controlled by the balance between beta-cell survival and beta-cell death (1; 27; 85). The increased beta-cell mass demonstrated in GLP-1/Ex4 treated mice occurred through both increased beta-cell proliferation/neogenesis and decreased beta-cell apoptosis, and these changes were associated with elevated expression of the protein kinases Akt1 and MAPK (3). Ex4 treatment of db/db mice significantly elevated Akt1 protein expression level in association with increased beta-cell proliferation and decreased beta-cell apoptosis, showing a role of Akt1 in mediating GLP-1-induced proliferation and anti-apoptotic effects (3). In INS-1 cells that GLP-1 induces Akt phosphorylation in parallel with the PI3-K-dependent incorporation of $^3$H-thymidine. The role for Akt1 in the GLP-1 induced stimulation of beta-cell mass is described previously (3; 22). Of significance, when compared with some other antidiabetic agents including sulphonylureas and insulin, is the absence of associated weight gain (86; 87). Through its ability to enhance satiety, GLP-1 reduces food intake, thereby limiting weight gain, and may cause weight loss (21; 88). These features render GLP-1 highly desirable as an antidiabetic agent. However, while GLP-1 is most effective when administered continuously, single subcutaneous injections have short-lasting effects. The short half-life of native GLP-1 from N-terminal cleavage by dipeptidyl peptidase IV (DPP-IV) and the consequent requirement for constant GLP-1 infusion in clinical trials has been a serious drawback. DPP-IV inhibitors have been generated and assessed using mouse models and in clinical trials with some success (34).

Strategies for enhancing the therapeutic potential of GLP-1 have been the focus of intense research in both academia and the pharmaceutical industry (89). This includes the use of modified GLP-1 DPP-IV-resistance peptides with mutations in His$^7$ (36) and Ala$^8$ residues (35). However, while some of the GLP-1 derived agonists are evidently DPP-IV resistant, they are rapidly cleared from the plasma by other mechanisms, i.e. by renal clearance. A Gila monster-derived GLP-1R agonist, Ex4, is DPP-IV resistant and possesses a longer half-life which is partly attributed to the Glu$^8$ residue. Although extremely promising in animal models, daily administration of Ex4 and/or combination therapy with oral anti-diabetic agents was required in clinical studies to normalize blood glucose levels. The need for daily injection of these peptides has motivated efforts toward development of longer-acting molecules that retain the native GLP-1 actions.

Several strategies have been developed which focus on reducing enzymatic degradation by DPP-IV and simultaneously decreasing its circulating clearance. In particular, in the case of NN2211 (90), acylation of GLP-1 with a fatty acid chain promotes binding of the peptide to serum albumin in vivo. This provides the peptide with the dual benefits of being DPP-IV resistant and having reduced renal filtration (91). CJC-1131 (40) is a DPP-IV-resistant GLP-1 analog where the native L-Ala8 is substituted with a D-Ala. In addition, the GLP-1 molecule is coupled to a reactive chemical linker that can form a covalent bond with serum albumin (40). Albugon (92) is a recombinant DPP-IV-resistant GLP-1 molecule that is generated in frame with the human serum albumin sequence. Consequently, this GLP-1R agonist has decreased clearance and prolonged half-life (40; 92). Resisting enzymatic degradation and reducing renal clearance are desirable characteristics and the rationales behind these pharmaceutical agents. All three compounds are at a different stage of clinical study (Ex4 has been approved by FDA on Apr. 29, 2005).

The GLP-1 derived fusion protein is provided by the fusion of the GLP-1 and IgG1-Fc cDNA sequences (FIG. 1). An IgG-Fc based drug provides a numbers of advantages (93; 94). Since the IgG fusion molecules are produced as homodimers of 70 kilodaltons (FIG. 4), they are not rapidly cleared by the kidneys, and they have a substantially longer half-life (93; 94). Thus, the larger GLP-1/IgG-Fc homodimeric fusion molecule will have increased circulating half-life compared to native GLP-1. The GLP-1/IgG-Fc fusion protein would have reduced susceptibility to degradation since some degrading enzymes have a preference for smaller peptides (95). Furthermore, the dimeric GLP-1 is expected to increase the ligand avidity since homodimerized GLP-1 can potentially recruit additional GLP-1Rs and amplify intracellular signaling via preformed GPCR dimers/oligomers (81).

cAMP and insulin secretion assays suggest that the fusion protein of the present invention is able to activate GLP-1Rs in clonal INS-1 cells. The ability of the fusion protein to stimulate insulin secretion in INS-1 cells in a glucose-dependent manner further suggests that the GLP-1 fusion protein retains the biological function of the native GLP-1.

The in vivo expression of GLP-1/IgG-Fc fusion proteins by an intramuscular gene transfer approach has the advantage of continuously releasing fusion protein into the circulation over a period of many weeks. The circulating GLP-1 fusion proteins were detectable in the db/db mice (FIG. 8) and CD1 mice (not shown) two weeks after intramuscular injection of GLP-1/IgG-Fc vectors but not in the mice injected with control IgG-only plasmids. The elevated blood levels of GLP-1 fusion proteins (as determined by GLP-1 RIA) lasted for 12 weeks after the first injection. The reduced fasting blood glucose levels in the GLP-1/IgG-Fc expressing db/db mice were associated with increased fasting insulin levels and decreased fasting glucagon levels suggesting that the normalization of the fasting blood glucose was contributed by enhanced insulin secretion and suppressed glucagon release.

The db/db mice are a severe type II diabetes model because of a deficiency in leptin signaling (96; 97). Initially, the glucose levels in both the groups continued to rise perhaps as a result of progressive, unabated diabetes in the db/db mice. We have previously provided evidence that enhancement of beta-cell mass/function via increased beta-cell proliferation and decreased beta-cell apoptosis is important in preventing onset of diabetes in a subject with insulin resistance (3). Action of GLP-1 on enhancement of beta-cell mass/function is mediated by activation of intracellular protein kinases including Akt and MAPK and deactivation of caspases including caspase-3 (3; 22). It is conceivable that this mechanism is predominant in preventing and treating type I diabetes subjects.

An effect of GLP-1/IgG-Fc on body weight was not currently observed which is seen in some cases of native GLP-1 treatment in rodent models (98). However, anorectic effects have not been observed in several GLP-1 analogues in spite of clear insulinotrophic glucose lowering effects (40). Treatment with the long-acting and potent GLP-1R agonist Ex4 improved fasting blood glucose in the db/db mice associated with enhanced beta-cells mass and function (3). However, the body weight as well as the peripheral insulin sensitivities remained unchanged (3). These findings further support the notion that the onset of diabetes only occurs when the beta-cell dysfunction appears (99; 100). The anorexic effects of GLP-1 have been linked to its action on multiple brain regions in the central nervous system (101). Other mouse diabetic models currently available are nonobese diabetic (NOD) mice which is an excellent model of autoimmune diabetes (type I diabetes), islet-antigen reactive T cells infiltrate islets of Langerhans and kill islet cells, and/or initiate an inflammatory process that results in islet cell death (53).

Figure 10:
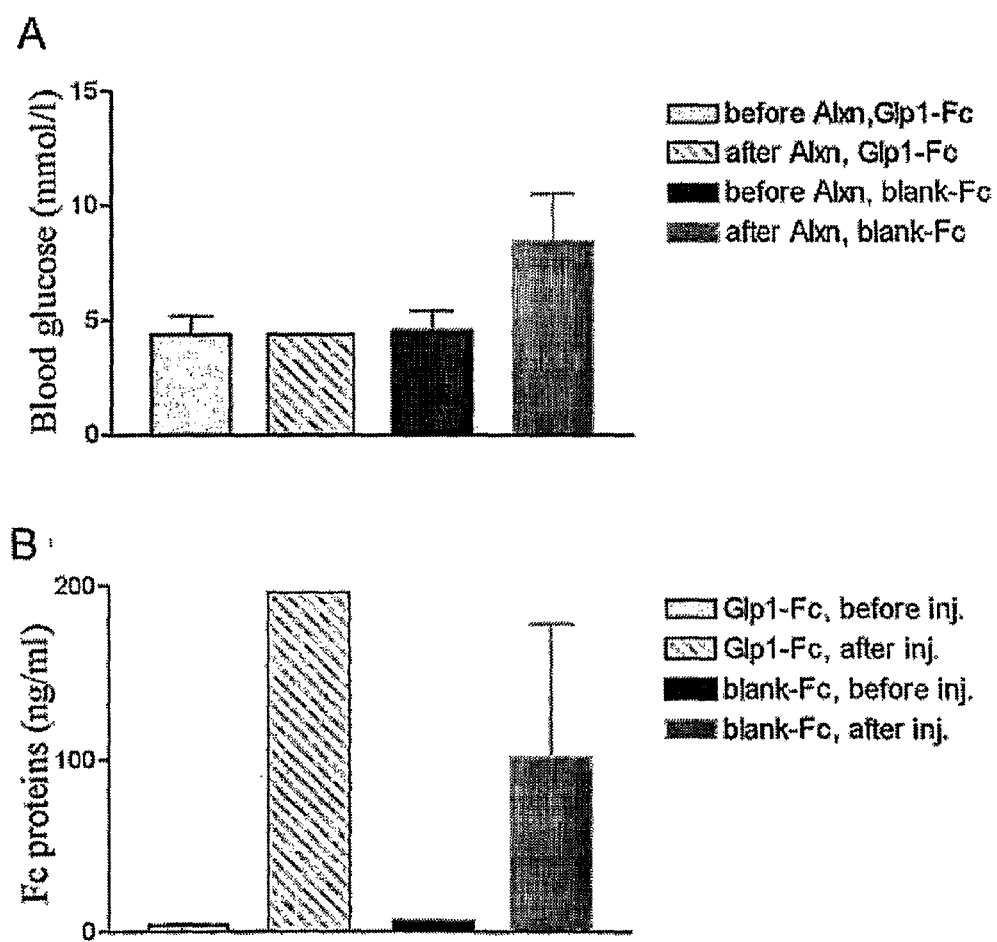
FIG. 10 shows the in vivo expression of GLP-1/IgG-Fc and its effect on blood glucose in pigs. GLP-1/IgG-Fc or control IgG-Fc vectors (4 mg/pig) were injected intramuscularly into male Yorkshire pigs (23 kg) followed by electroporation using the ADViSYS electroporator. To induce hyperglycemia, three days after the GLP-1/IgG-Fc vector injection, Alloxan monohydrate (Sigma/80 mg/kg) was administered in 25 ml saline intravenously under general Fluorothane-induced anesthesia. Initially, the acidic Alloxan solution was neutralized before injections. However, neutralized solution did not effectively cause hyperglycemia and thus subsequent injections were performed without neutralization, which resulted in moderate hyperglycemia in the blank IgG-Fc injected pigs, but not in the pigs injected with GLP-1/IgG-Fc vectors. The fasting blood glucose was tested twice a week in ketamine-sedated pigs when blood samples were withdrawn using a glucometer (A) and the expression of the Fc proteins was determined using ELISA (B).

GLP-1/IgG$_1$-Fc or control IgG$_1$-Fc vectors (4 mg/pig) were muscularly injected into male Yorkshire pigs (23 kg) followed by electroporation using ADViSYS electroporator (FIG. 10). Three days after injection, Alloxan monohydrate (80 mg/kg, Sigma) was administered in 25 ml saline intravenously under general anesthesia by Fluorothane. As shown in FIG. 10, injections of the Alloxan in pigs with treated with the blank IgG-Fc vectors induced moderate hyperglycemia, but not in the pigs treated with GLP-1/IgG-Fc vectors. The fasting blood glucose was tested twice a week in ketamine-sedated pigs when blood samples were withdrawn using a glucometer (FIG. 10A) and the expression of the Fc proteins were determined using ELISA (FIG. 10B).

The fusion proteins of the composition can be provided as peptides or alternatively as cDNA sequences within vectors encoding secretable fusion proteins of the invention including but not limited to: active GLP-1 and mouse IgG$_1$-Fc cDNAs or GLP-1 human IgG$_2$-Fc cDNAs for mammalian expression of bivalent GLP-1 peptide; and active Ex4-IgG cDNAs. One of skill in the art could readily prepare any desired GLP-1 or Ex4 sequence in a vector as is described herein in the examples or similar methods. The biological properties and effectiveness of the recombinant human chimeric GLP-1 fusion protein, GLP-1/IgG-Fc, was demonstrated using a combination of in vitro cell line studies and by a gene therapy approach by intramuscular gene transfer expression of the fusion proteins to type I and type II diabetic mouse models in vivo. This gene therapy approach proved effective in a murine model of severe type I and type II diabetes. Electroporation was used because it increased gene transfer and may prove useful in large animals and humans, where intramuscular gene transfer is less efficient than in rodents. Together, this invention provides a novel approaches for the treatment and prevention of type I and type II diabetes using protein and gene therapy techniques in mammalian subjects.

The fusion protein of the invention may be a GLP-1 or Ex4 fragment having a sequence that shares at least 60% sequence identity or more to a GLP-1 polypeptide or at least 60% or more sequence identity to an Ex4 polypeptide. In aspects, the sequence identity may be at least 70%, 80%, 90% or 95% or more sequence identity to known forms of GLP-1, and this includes analogues, derivatives thereof and fragments thereof. Such sequences are disclosed for example in U.S. Pat. No. 6,268,343 (the disclosure of which is incorporated herein by reference in its entirety). The invention includes the use of all the aforementioned compounds for prevention and treatment of diabetes, such as type I and type II diabetes patients. The invention also includes use of all the aforementioned compounds for preparation of a medicament for prevention and treatment of diabetes, such as type I and type II diabetes. The invention also includes a pharmaceutical composition, such as a prophylactic composition, for all the aforementioned uses.

Changes which result in production of a chemically equivalent or chemically similar amino acid sequence are included within the scope of the invention. IgG-Fc-fused polypeptides sharing sequence identity to GLP-1 or Ex4 are within the scope of the present invention and may be readily tested to ensure that they are suitable for use in the methods of the invention. U.S. Pat. No. 6,268,343 (incorporated by reference in its entirety), describes a number of GLP-1 derivatives and variants. Variants of the polypeptides of the invention may occur naturally, for example, by mutation, or may be made, for example, with polypeptide engineering techniques such as site directed mutagenesis, which are well known in the art for substitution of amino acids. For example, a hydrophobic residue, such as glycine can be substituted for another hydrophobic residue such as alanine. An alanine residue may be substituted with a more hydrophobic residue such as leucine, valine or isoleucine. A negatively charged amino acid such as aspartic acid may be substituted for glutamic acid. A positively charged amino acid such as lysine may be substituted for another positively charged amino acid such as arginine. The invention provides fusion proteins combining derivatives of GLP-1 molecule including a DPP-IV resistant form such as GLP-1A8G with an IgG-Fc molecule to form a new molecule that possess enhanced GLP-1 actions and advantages of IgG-Fc molecule as described.

Therefore, the invention encompasses IgG-Fc-fused polypeptides having conservative changes or substitutions in amino acid sequences. Conservative substitutions insert one or more amino acids, which have similar chemical properties as the replaced amino acids. The invention includes sequences where conservative substitutions are made that do not destroy compound activity. IgG-Fc-fused polypeptides comprising one or more D-amino acids are contemplated within the invention. Also contemplated are polypeptides where one or more amino acids are acetylated at the N-terminus. Those with skill in the art recognize that a variety of techniques are available for constructing polypeptide mimetics with the same or similar desired compound activity as the corresponding polypeptide compound of the invention but with more favorable activity than the polypeptide with respect to solubility, stability, and/or susceptibility to hydrolysis and proteolysis. See, for example, Morgan and Gainor, Ann. Rep. Med. Chem., 24:243-252 (1989). Examples of polypeptide mimetics are described in U.S. Pat. No. 5,643,873. Other patents describing how to make and use mimetics include, for example in, U.S. Pat. Nos. 5,786,322, 5,767,075, 5,763,571, 5,753,226, 5,683,983, 5,677,280, 5,672,584, 5,668,110, 5,654,276, 5,643,873 are all incorporated herein by reference in their entirety. Mimetics of the polypeptides of the invention may also be made according to other techniques known in the art. For example, by treating an IgG-Fc-fused polypeptide of the invention with an agent that chemically alters a side group by converting a hydrogen group to another group such as a hydroxyl or amino group. Mimetics preferably include sequences that are either entirely made of amino acids or sequences that are hybrids including amino acids and modified amino acids or other organic molecules. The invention also includes hybrid and IgG-Fc-fused polypeptides, for example where a nucleotide sequence is combined with a second sequence.

The invention also includes IgG-Fc-fused polypeptide fragments of the IgG-Fc-fused polypeptides of the invention that may be used to confer compound activity if the fragments retain activity. The invention also includes IgG-Fc-fused polypeptides fragments of the IgG-Fc-fused polypeptides of the invention which may be used as a research tool to characterize the polypeptide or its activity. Such polypeptides preferably consist of at least 5 amino acids. In embodiments, they may consist of 6 to 10, 11 to 15, 16 to 25, 26 to 50, 51 to 75, 76 to 100 or 101 to 250 amino acids. Fragments may include sequences with one or more amino acids removed, for example, C-terminus amino acids in a compound sequence.

The activity of the fusion protein is increased or decreased by carrying out selective site-directed mutagenesis. A DNA plasmid or expression vector containing the nucleic acid molecule or a nucleic acid molecule having sequence identity is preferably used for these studies using the U.S.E. (Unique site elimination) mutagenesis kit from Pharmacia Biotech or other mutagenesis kits that are commercially available, or using PCR. Once the mutation is created and confirmed by DNA sequence analysis, the mutant fusion protein is expressed using an expression system and its activity is monitored.

The invention also includes fusion proteins which have sequence identity at least about: >20%, >25%, >28%, >30%, >35%, >40%, >50%, >60%, >70%, >80% or >90% more preferably at least about >95%, >99% or >99.5%, to a sequence of the invention (or a partial sequence thereof). Modified fusion protein molecules are discussed below. Preferably about: 1, 2, 3, 4, 5, 6 to 10, 10 to 25, 26 to 50 or 51 to 100, or 101 to 250 nucleotides or amino acids are modified. Identity is calculated according to methods known in the art. Sequence identity is most preferably assessed by the BLAST version 2.1 program advanced search (parameters as above). BLAST is a series of programs that are available online at http://www.ncbi.nlm.nih.gov/BLAST. The advanced blast search (http://www.ncbi.nlm.nih.gov/blast/blast.cgi?J-form=1) is set to default parameters. (ie Matrix BLOSUM62; Gap existence cost 11; Per residue gap cost 1; Lambda ratio 0.85 default). References to BLAST searches are: Altschul, S. F., Gish, W., Miller, W., Myers, E. W. & Lipman, D. J. (1990) "Basic local alignment search tool." J. Mol. Biol. 215:403__410; Gish, W. & States, D. J. (1993) "Identification of protein coding regions by database similarity search." Nature Genet. 3:266__272; Madden, T. L., Tatusov, R. L. & Zhang J. (1996) "Applications of network BLAST server" Meth. Enzymol. 266:131__141; Altschul, S. F., Madden, T. L., Schäffer, A. A., Zhang, J., Zhang, Z., Miller, W. & Lipman, D. J. (1997) "Gapped BLAST and PSI_BLAST: a new generation of protein database search programs." Nucleic Acids Res. 25:3389__3402; and Zhang, J. & Madden, T. L. (1997) "PowerBLAST: A new network BLAST application for interactive or automated sequence analysis and annotation." Genome Res. 7:649__656.

The invention encompasses fusion proteins with mutations that cause an amino acid change in a portion of the fusion protein not involved in providing activity or an amino acid change in a portion of the fusion protein involved in providing activity so that the mutation increases or decreases the activity of the fusion protein. In aspects of the invention, the IgG-Fc portion of the fusion protein may also be modified by techniques well known to those skilled in the art to alter (increase or decrease) the level of immunogenicity and effector function as disclosed in WO 05/000892 (incorporated herein by reference in its entirety). In addition to the GLP-1/IgG-Fc fusion protein portion of the composition of the present invention, the composition further comprises an autoimmune suppressor. The autoimmune suppressor comprises at least one target antigenic epitope that effectively decrease autoimmunity, such that the pancreatic islet cells are not destroyed. In an embodiment, the target antigenic epitope may be encoded by a nucleotide sequence as in a DNA vaccine. The DNA vaccine portion of the composition comprises one or more plasmids encoding at least one target islet antigen. In aspects, the target islet antigen(s) has for its purpose to silence autoimmune response to islet beta cells. In an embodiment, the plasmid may encode pre-proinsulin and/or GAD. The DNA vaccine portion of the composition may optionally contain a negative T cell regulator that downregulates the T-cell mediated response against the pancreatic insulin-secreting beta cells. In an embodiment, the negative T cell regulator is B7-1wa.

Pre-proinsulin is a 110-amino acid single-chain polypeptide that is the precursor of insulin. Pre-proinsulin is proteolytically converted to proinsulin, which consists of the A chain, B chain, and C peptide. Proinsulin is homologous with IGF-I and -II and can bind to the insulin receptor with approximately 10% of the affinity of insulin (Shuldiner A R, Barbetti F, Raben N, Scavo L, Serrano J 1998 Insulin. In: LeRoith D (ed) Insulin-like Growth Factors: Molecular and Cellular Aspects. CRC Press, Boca Raton, Fla., pp 181-219). Proinsulin is normally expressed in beta cell and has been identified as a possible autoantigen (Rudy G et al. Mol Med 1995; 1:625)

Glutamic acid decarboxylase (GAD65) is an enzyme that is produced primarily by pancreatic islet cells. In mammals, GAD exists in two isoforms encoded by two different genes—Gad1 and Gad2. These isoforms are GAD67 and GAD65 with molecular weights of 67 and 65 kDa, respectively (Erlander M G, Tillakaratne N J K, Feldblum S, Patel N, Tobin A J (1991) Two genes encode distinct glutamate decarboxylases. Neuron 7:91-100). It is believed that GAD is one the best known targets of autoreactive T cells during the early phase of the autoimmune response (Kaufman et al. Nature 1993; 366:69).

B7-1wa is a mutant of the B7-1 ligand that binds specifically to the CTLA-4 antigen on activated T cells. The CTLA-4 molecule, together with CD28 (another costimulatory molecule expressed on the surface of both resting and activated T cells), plays a critical role in the T-cell response to antigen presentation. T-cell activation is initiated when the antigen-specific cell-surface T-cell receptor (TCR; CD3 complex) engages the antigen, which is bound to an MHC class II molecule on the surface of an antigen-presenting cell. However, to complete this activation, leading to T-cell proliferation and cytokine production, a second signal (co-stimulatory signal) is required. In the absence of a positive co-stimulatory signal, the antigen-TCR engagement is ineffective, and causes the T cell to be refractory to further stimuli (anergy) or induces apoptosis of the cell. This positive co-stimulatory signal is provided mainly by the interaction of CD28 with its ligands, B7-1 (CD80) and B7-2 (CD86) on antigen-presenting cells. CTLA-4 also binds to the same B7 ligands but, in contrast to CD28, it delivers inhibitory signals to T-cell activation (Vaidya B et al. European Journal of Endocrinology (2004) 150 619-626).

In general, the DNA vaccine portion of the composition of the invention typically comprises a plasmid vector into which is inserted a strong promoter, the gene(s) of interest (i.e. nucleic acid sequences encoding various forms of pre-proinsulin, GAD65 and optionally B7-1wa) and a polyadenylation/ transcriptional termination sequence. The DNA vaccine includes regulatory elements necessary for gene expression of the nucleic acid molecule. The elements include: a promoter, an initiation codon, a stop codon, and a polyadenylation signal. In addition, enhancers are often required for gene expression of the sequence that encodes the immunogenic target protein. It is necessary that these elements be operably linked to the sequence that encodes the desired proteins and that the regulatory elements are operable in the subject to whom they are administered. Initiation codons and stop codons are generally considered to be part of a nucleotide sequence that encodes the immunogenic target protein. However, it is necessary that these elements are functional in the individual to whom the gene construct is administered. The initiation and termination codons must be in frame with the coding sequence. The gene(s) of interest may encode a full protein or simply an antigenic peptide sequence. The plasmid can be grown in bacteria, such as for example E. coli and then isolated and prepared in an appropriate medium, depending upon the intended route of administration, before being administered to the host. Following administration the plasmid is taken up by cells of the host where the encoded peptide is produced. The plasmid vector will preferably be made without an origin of replication which is functional in eukaryotic cells, in order to prevent plasmid replication in the mammalian host and integration within chromosomal DNA of the animal concerned. Suitable methods for preparing the DNA vaccine of the composition of the invention for the treatment of type I diabetes are disclosed for example in U.S. Pat. Nos. 6,846,808, 7,078,388, 7,084,249 and 7,067,138 (the disclosures of which are incorporated herein by reference).

The composition of the invention may also be a DNA vaccine containing nucleic acid sequences with at least 60% sequence identity to a nucleotide sequence of pre-proinsulin and GAD65 and/or at least 60% sequence identity to a ligand (B7-1 mutant, B7-1wa) of the negative T-cell regulatory protein CTLA-4. The wild-type (wt) B7-1 is also called CD80. The B7-1wa used the composition of the present invention has a substitution of Trp88 for Ala and was first described by Guo Y, Wu Y, Kong X, and Liu Y. and published in Mol. Immunol., 35, 215-225 (1998). It is also understood by one of skill in the art that the invention may encompass a composition where the fusion proteins and autoimmune suppressors are provided in separate vectors.

In the present invention, Tr cells were generated by the administration of the composition of the invention when delivery of the composition containing the antigen gene was combined with a CTLA-4 (CD152) ligand (FIGS. 11-16). This approach was protective against type I diabetes in NOD mice. CTLA-4 is a powerful negative regulator of T cells and it appears important for the activity of some Tr cells (107-109). No natural ligand discriminates between CTLA-4 and the positive co-stimulatory molecule CD28, since both bind B7-1 and B7-2 (expressed primarily by antigen presenting cells [APCs]). To solve this problem, a mutated B7-1 molecule (B7-1wa) was utilized which has a single amino acid substitution (W88 to A), and binds CTLA-4 but not CD28 (110-112).

A PPIns/GAD65 fusion (Ins-GAD) construct was used as the target antigen to introduce a larger number of autoantigenic target epitopes. The addition of the DNA encoding for B7-1wa allowed the linkage of antigen recognition by the T cell receptor (TCR) with delivery of a negative regulatory signal. This consistently generated Tr cells that inhibited responses to insulin or GAD65 peptide, and protected against spontaneous development of disease, or adoptive transfer disease in NOD scid mice (FIGS. 11-16). The T cells included CD4+ cells of both CD25+ and CD25− phenotype, and expressed B7-1 and markers associated with Tr function, i.e., CTLA-4, neuropilin-1 (Nrp1) and membrane-associated TGF-β1. This is the first study demonstrating that induction of this type of Tr cells by DNA vaccination. Importantly, suppression appeared to be specific to the immunizing islet antigens, and not to unrelated antigens. Moreover, vaccination of newly diabetic mice induced remission in some mice demonstrating prevention and treatment of type I diabetes.

The pancreatic beta-cell-associated antigens may be used as the autoimmune suppressors in the composition of the present invention. These antigens are believed to be antigenic target epitopes in type I diabetes. These antigens include but are not limited to pre-proinsulin, heat shock protein 65 (hsp65; see U.S. Pat. No. 5,114,844), insulin B-chain, carboxypeptidase H, peripherin, GAD65, GAD67 and other pancreatic beta-cell-associated antigens and autoantigens which are known in the art.

The autoimmune suppressors of the present invention may also comprise other negative regulatory molecules, more specifically negative regulators of T cells. The numerous types of negative regulators of T cell function are known to those of skill in the art and are also contemplated for use in the composition of the present invention.

The composition of the present invention may also be provided with facilitating agents. In embodiments, these facilitating agents may be adjuvants as disclosed in U.S. Pat. No. 6,207,159 (herein incorporated by reference in its entirety) and commonly known by those skilled in the art. Furthermore, in embodiments, the composition of the present invention may also be provided with cell stimulating agents as disclosed in U.S. Pat. No. 6,884,785 (herein incorporated by reference in its entirety) and commonly known by those skilled in the art to facilitate nucleic acid uptake. In additional embodiments, the composition of the present invention may also be provided with cytokines as disclosed in U.S. Pat. No. 7,078,388 (herein incorporated by reference in its entirety) but not limited chemokine, interferon, interleukins and others well known by those skilled in the art to modify an immune response.

The composition of the present invention provides also describes autoimmune suppressors which may be encoded by DNA vaccines, where the DNA vaccines have sequence identity at least about: >20%, >25%, >28%, >30%, >35%, >40%, >50%, >60%, >70%, >80% or >90% more preferably at least about >95%, >99% or >99.5%, to a sequence of the invention (or a partial sequence thereof). Modified cDNA sequences are discussed below. Preferably about: 1, 2, 3, 4, 5, 6 to 10, 10 to 25, 26 to 50 or 51 to 100, or 101 to 250 nucleotides or amino acids are modified.

The composition of the present invention in an embodiment provides for the expression of the fusion proteins and the incorporated DNA sequences (as a vaccine) with mutations that cause an amino acid change in a portion of the nucleotide vaccine sequence of which is not involved in providing activity or an amino acid change in a portion of the DNA vaccine involved in providing activity so that the mutation increases or decreases the activity of the DNA vaccination. The activity of the DNA vaccine is increased or decreased by carrying out selective site-directed mutagenesis. A DNA plasmid or expression vector containing the nucleic acid molecule or a nucleic acid molecule having sequence identity is preferably used for these studies using the U.S.E. (Unique site elimination) mutagenesis kit from Pharmacia Biotech or other mutagenesis kits that are commercially available, or using PCR. Once the mutation is created and confirmed by DNA sequence analysis, the mutant fusion protein is expressed using an expression system and its activity is monitored.

This application also includes use of all the aforementioned compounds for preparation of a medicament for prevention and treatment of type I diabetes. The invention also includes a pharmaceutical composition, such as a prophylactic composition, for all the aforementioned uses. The pharmaceutical compositions of the invention are formulated to contain the described fusion peptides and DNA vaccine portion and can be administered to humans or animals by a variety of methods including, but not restricted to topical administration, oral administration, aerosol administration, intratracheal instillation, intraperitoneal injection, intravenous injection, intramuscular injection and gene therapy approach. Dosages to be administered depend on patient needs, on the desired effect and on the chosen route of administration. An example of a dosage of the fusion protein for humans would be 2 nmol/kg of body weight or between about 0.02 to 100 nmol/kg of body weight. Suitable concentrations of the DNA encoding the fusion protein for use may be about 1 µg/kg of body weight to 10 µg/kg of body or between 0.1 to 100 µg/kg of body weight. Suitable concentrations of the DNA vaccine for use comprises 0.1 to about 1000 microgram of DNA. In some preferred embodiments, the vaccines contain about 1 to about 500 micrograms of DNA. In some preferred embodiments the vaccines contain about 25 to 250 micrograms of DNA. The composition may also be introduced into cells using in vivo liposome or viral delivery vehicles. The numerous types of delivery vehicles suitable for use with the invention are well known to those skilled in the art. The compositions may be administered daily, weekly or as advised by a physician for as long as is required.

The composition of the fusion proteins and an autoimmune suppressors of the invention are useful alone, but may also be combined with other components such as a carrier or adjuvants in a pharmaceutical composition. The pharmaceutical compositions can be prepared by known methods for the preparation of pharmaceutically acceptable compositions which can be administered to patients, and such that an effective quantity of the nucleic acid or polypeptide molecule is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA). On this basis, the pharmaceutical compositions could include an active compound or substance, such as a compound nucleic acid, polypeptide molecule or fusion protein, in association with one or more pharmaceutically acceptable vehicles or diluents, and contained in buffered solutions with a suitable pH and isoosmotic with the physiological fluids. The methods of combining the active molecules with the vehicles or combining them with diluents is well known to those skilled in the art. The composition could include a targeting agent for the transport of the active compound to specified sites within tissue.

Proteins having sequence identity to the receptor for GLP-1 (or Ex4) may be tested to demonstrate that they are suitable for use in the methods of the invention. Small organic molecules are also tested. The invention includes compounds which are identified with the screening methods of the invention and which are suitable for methods and uses of the invention and in pharmaceutical compositions of the invention. In a preferred embodiment, the invention includes an assay for evaluating whether a candidate compound is capable of increasing cAMP generation, Akt-1 or MAPK expression or activity or decreasing caspase-3 expression or activity, by culturing cells (preferably beta-cells) in the presence of at least one compound whose ability to modulate (inhibit or activate) expression activity is sought to be determined and thereafter monitoring the cells for either an increase or decrease in the level of Akt-1 or MAPK expression or activity or decreasing caspase-3 expression or activity.

A receptor binding assay is the preferred method to evaluate the specificity of a compound for the cell membrane receptor, as all signaling transducing events are initiated from this ligand-receptor binding. If a candidate compound binds to the receptor (for example, as identified with a gel-shift mobility assay using cross-linking technique, or a competitive receptor binding assay), this binding indicates that the compound is suitable for use in the subsequent steps of the invention. Receptor activation assays are used to further determine the suitability of a candidate compound for the methods of the invention. For example, cAMP determination can be used to evaluate the receptor activation (GLP-1 receptor is GPCR). In addition, an Akt kinase assay can further show the activation of Akt. In the initial screens, when there are large numbers of compound candidates, a receptor binding assay can be used. Compounds that bind to the receptor are preferably subjected to cAMP determination, and finally an Akt kinase assay. Small organic molecules may also be tested as candidate compounds for their suitability for use in the methods of the invention. To this end, cAMP determination is optionally used to screen for GPCR binding and activation. As per the rationale described above, Akt kinase assay, or MAPK assay is optionally used to evaluate the cellular effectivity of the compounds.

To validate both screened peptide and organic molecule compounds, beta-cell mass analysis can be performed in the pre-diabetic animal models after treatment of the animal with the compounds for a longer period (i.e. 2-12 weeks). To this end, an additional insulin-release assay can also performed using an insulin radioimmunoassay kit (Linco Research, St. Louis, Mo.). These experimental approaches confirm the growth effects of the screened compounds on the beta-cells. To validate both screened peptide and organic molecule compounds, beta-cell mass analysis can be performed in the pre-diabetic animal model after treatment of the animal with the compounds for a longer period (i.e. 2-12 weeks). To this end, an additional Insulin-release assay can also performed using an insulin radioimmunoassay kit (Linco Research, St. Louis, Mo.). These experimental approaches confirm the growth effects of the screened compounds on the beta-cells. To validate screened vectors, the DNA plasmids can be administered to pre-diabetic animal models through gene transfer. The administration can be repeated every two months or six months or every year or as deemed necessary.

The compositions of the invention may be used in conjunction with any other known agents for treatment for type I and/or type II diabetes, such as for example with the use of diabetes medicaments and insulins. Diabetic medicaments may include for example Actos, Amaryl, avandia, DiaBeta, Diabinese, Dymelor, Glucophage, Glucophage XR, Glucotrol, Glucotrol XL, Glucovance, glynase, PresTab, Glyset, Micronase, Orinase, Pandin, Precose, Starlix and Tolinase. Suitable insulins include for example Aspart, Insulin Glargine (Lantus), Lente, Lispro (Humalog), NPH and Ultralente.

A subject for which the present invention is suitable is any subject in need of such treatment which is one that is at risk for developing diabetes, a subject newly diagnosed with diabetes or a subject already diagnosed with diabetes. The invention is relevant towards the treatment and/or prevention of type I diabetes as described herein. For example, such subjects may be a person with a genetic history of diabetes who has not yet developed diabetes or, who has newly diagnosed or diagnosed as diabetes. The subject may also be a person whose blood glucose is higher than average for that person's age and weight (normal blood glucose may be routinely determined from medical reference sources), although not high enough that the person is diagnosed diabetic. The subject may also be a person with a genetic history of diabetes who has not yet developed diabetes. Diabetes is diagnosed when the blood sugar levels are higher than an accepted normal range. According to ADA (American Diabetes Association) and CDA (Canadian Diabetes Association) standards, diabetes onset occurs when a subject has a fasting blood glucose level over 7.0 mmol/L, or a random (anytime of day) sugar that is greater than 11.1 mmol/L. Once diagnosed, any effort/means made to the patient, in order to combat the hyperglycemia, is treatment, rather than prevention. Some people, although not diabetic, (e.g. obese people, whose excess weight is usually associated with insulin resistance) have poor health and a higher risk of development of type II diabetes. The compositions of the invention are administered to prevent and/or treat a subject with type I diabetes. Type I diabetes patient refers to a subject who usually has genetic predisposition or, who has insulitis beta-cell injury or, who has "pre"-diabetes with loss of first phase of insulin response, or a person who has been newly diagnosed diabetes. In newly diagnosed type I diabetes patients, as a result of the immune system attacking and destroying the insulin-producing islet beta-cells, their pancreas produce little or no insulin.

The transfer of naked plasmid DNA following needle injection occurs more readily in skeletal muscle than in most other tissues (117; 118). Moreover, transgene expression is generally much more prolonged than in other tissues, probably because striated myocytes are nondividing, long-lived cells. While gene transfection by naked DNA injection is not efficient, this is greatly improved (50 to 1000 fold) by in vivo electroporation (72; 119). Electric pulses are thought to increase DNA entry into cells by creating transient pores in the cell membrane, and by promoting DNA motility (electrophoretic effect). We apply low field strength (100-200 V/cm), relatively long (20-50 milliseconds) square-wave electric pulses, 6-8 times in quick succession. These low-voltage electrical pulses cause muscle damage, but it is usually mild and transient. In previous studies, the majority of surviving fibers expressed a reporter gene after vector delivery and electroporation (120). Two weeks after electroporation the muscles appeared grossly normal (120).

Intramuscular delivery of plasmid vectors has proven to be an efficient and safe method of gene transfer when combined with in vivo electroporation. This method is versatile, and has been applied to the delivery of cytokines, peptide hormones, soluble receptors, as well as many membrane-bound or cytoplasmic proteins. Indeed, it is particularly useful for the systemic delivery of protein mediators, such as GLP-1/IgG-Fc. It is conceivably effective when administration of GLP-1/IgG-Fc protein by direct injection of the fusion proteins. To this regard, the IgG fusion approach has the advantage of a simple one-step procedure for the production of a GLP-1 fusion peptide on a laboratory scale. GLP-1 RIAs showed that the production efficiency is lower in a bacterial expression system than a mammalian expression system. This could be attributed to misfolded proteins in *E. Coli* compared to COS-7 cells, although the use of Rosetta gami 2 bacterial cells was intended to enhance properly folded and functional proteins, which is achieved by increasing the formation of disulfide bonds in the *E. Coli* cytoplasm (121) and providing rare codon tRNAs compensating for insufficient levels in the *E. Coli* system (122).

The bivalent GLP-1/IgG-Fc fusion protein exists in native conditions. The fusion proteins displayed capacity to stimulate insulin secretion in a glucose-dependent manner and cAMP generation in INS-1 cells. In in vivo studies using mice models, the fusion protein may be delivered through a non-viral gene therapy approach, resulting in long-term expression of the fusion protein. This proved protective against streptozotocin (STZ)-induced diabetes (a model of beta-cell injury), and in db/db mice (type II diabetes model) involving a mechanism of expansion of beta-cell mass.

The method and of the invention comprises administering to a subject in need of treatment of type I diabetes, an effective amount of a composition that increases beta-cell proliferation or neogenesis and also reduces beta-cell apoptosis in the subject. The effective amount of the compound increases insulin release, glucose tolerance and decreases pancreatic cell autoimmunity in the subject.

The composition comprises a fusion protein and an autoimmune suppressor. The fusion protein generated has many advantages for the therapy of type I diabetes including long-acting, higher ligand avidity and associated with immunological tolerance. At the same time, the autoimmune suppressor possesses high specificity (only to the immunizing islet antigens) and decreases islet cell autoimmunity while not suppressing the systemic immune system. The invention discloses that direct administration of the composition of the present invention can be expressed in vivo using a novel gene therapy approach that does not require any type of virus for the vector delivery. These vectors have no infectious potential, provoke only mild local inflammatory reactions, and do not cause insertional mutagenesis. This prevents many of the drawbacks of viral gene therapy. This non-viral gene therapy is simpler and less expensive, and could be applied outside of a hospital setting by any physician. Non-viral gene therapy and/or DNA vaccination are effective in large mammals especially when enhanced by electroporation (reviewed in (69-76). Therefore, there is no obvious contra-indication for the use of these techniques in patients with autoimmune diseases, such as type I diabetes.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

Plasmid Construction

A vector encoding a fusion protein consisting of the human GLP-1 (7-37) and mouse $IgG_1$-Fc using overlap PCR was constructed to generate a long-acting, high efficacy and potent peptidergic agonist of biological GLP-1 (FIG. 1). The $IgG_1$-Fc region contains the $IgG_1$ constant heavy-chain (part of CH1, hinge, CH2 and CH3). An IgK secretion leader peptide sequence was fused with the GLP-1 sequence that directs the secretion of the synthesized peptide into the medium. The cDNA encoding the fusion protein hGHRH/hGLP-1 was chemically synthesized, ligated to a PCR-amplified cDNA fragment encoding human $IgG_2$ FC (hinge-ch2-ch3) and inserted into the NcoI and Hind III sites of the pAV0243 vector to generate GLP-1/hIgG-Fc/pAV0243. The secretable GLP-1/hIgG-Fc fusion protein contains the $IgG_2$ constant heavy-chain (hinge, CH2 and CH3). A GHRH secretion leader peptide sequence was fused with the GLP-1 sequence that directs the secretion of the synthesized peptide into the medium. This strategy ensures the generation of a GLP-1 fusion with an active histidine residue at the N-terminus of the fusion protein after cleavage of the secretion leader sequence peptide during the process of secretion. A schematic representation of the secreted GLP-1/IgG-Fc fusion protein is shown in FIG. 1. This approach is expected to 1) circumvent the short circulating half-life of GLP-1 since Fc fusion proteins are secreted as homodimers that possess longer circulating half-life and higher efficacy due to higher ligand avidity (78-80); 2) enhance the peptide potency since most GPCR are pre-formed in dimers at the cell surface (81); and 3) facilitate the purification, which can be achieved by one-step purification using Protein G sepharose (83).

Full length GLP-1 and mouse IgG-Fc cDNAs were amplified from GLP-1/PCR2.1 (kind gift from Dr. X Huang) and IgG plasmids using gene specific primers and overlap PCR. For the first overlap PCR, 5'-CCGGATATCGCCACCATG-GAGACAGACACACTCCTGCTATGGG-TACTGCTGCTCTGGGTTCCAGGTT CCACTGGT-GACCA-3' (SEQ ID No:17) and 5'-TGCTGAAGGGACCTTTACCAGTG-3' (SEQ ID No: 18) were used. The PCR products were used in a second overlap PCR to produce a contingent GLP-1/IgG-Fc cDNA. The amplification products were sub-cloned into the Bam HI and Eco RV sites of the vector. For the control vector that encodes IgG-Fc, IgG cDNA alone was amplified by PCR using 5'-CCGGATATCGCCACCATGGAGACAGACA-CACTCCTGCTATGGGTACTGCT-GCTCTGGGTTCCAGGTT CCACTGGTGACCCCAGC-GAGACCGTCACC-3' (SEQ ID No:19) and 5'-CGCGGATCCCTATCATTTACCAG-GAGAGTGGGAGAGG-3' (SEQ ID No:20) and cloned into the Bam HI and Eco RV sites of the vector.

The primers used for PCR-amplification of cDNA fragment encoding human $IgG_2$ FC (hinge-ch2-ch3) were: 5'-AAGGATATCGATCGCMATGTTGTGTC-GAGTGCCCA-3' (SEQ ID No: 25) and 5'-CGTMGCT-TCATTTACCCGGAGACAGGGAGAG-3' (SEQ ID No: 26).

The vector contains a CMV immediate-early enhancer-promoter, a single eukaryotic transcription unit, and minimal rabbit beta globin polyadenylation and transcription termination sequences (129). The vector is a derivative of the VR1255 vector (129), which has been modified by deleting the luciferase reporter gene and adding enzyme restriction sites. To permit secretion, the Igk-chain signal peptide sequence was introduced 5' to the GLP-1 or Ex4 sequence by PCR. To express GLP-1/IgG-Fc fusion proteins in bacteria, the fusion cDNA sequences were amplified by PCR from the plasmids and sub-cloned into the pET-28a (Novagen, EMD Bioscience, San Diego, Calif.) vector.

Example 2

Mammalian Expression of GLP-1/IqG-Fc Fusion Proteins

To assess the capacity of the vectors in terms of expression and secretion of the GLP-1/IgG-Fc fusion proteins, constructs were transiently transfected into COS-7 cells. Forty-eight hours after transfection, to evaluate the expression of the fusion constructs, total RNA from the transfected cells was prepared and expression was analyzed using RT-PCR. Transcripts for the GLP-1/IgG-Fc fusion constructs and IgG-Fc control constructs were detected using the gene specific primers (FIG. 2a). No transcripts were detected in non-transfected samples.

The lysates and medium from the transfected COS-7 cells were also analyzed for expression of the fusion proteins by Western blotting using anti-mouse antibodies. As shown in FIG. 2b, Fc fusion proteins were detected in both the medium and cell lysates. The fusion proteins migrated at 35 kDa, the size of the fusion protein monomers under the SDS-PAGE reducing conditions. Detection of the fusion proteins both in the conditioned media and the cell lysates shows that the fusion proteins were synthesized and secreted from the mammalian cells.

The identity of the GLP-1 fusion protein was further confirmed by a GLP-1 radioimmunoassay (RIA), which allows for detection of all forms of GLP-1. COS-7 cells were transiently transfected with increasing amounts of GLP-1/IgG-Fc/VRnew or Fc-only/VRnew plasmids and media were collected 48 hours following transfection. The medium was used in GLP-1 RIAs to detect total GLP-1. While no GLP-1 was detected in medium from non-transfected or Fc-only/VRnew transfected COS-7 cells, GLP-1 was detected in a DNA-dose dependent manner in the medium collected from GLP-1/IgG-Fc/VRnew-tranfected cells (FIG. 3). Up to 100 micromole of total GLP-1 was purified from 50 mL of COS-7 medium after transfection with 0.8 microliter of DNA/$1.25\times10^5$ cells/ml.

For mammalian expression, GLP-1/IgG-Fc or IgG-Fc cDNA was transfected into COS-7 cells using Lipofectamine-2000 (Invitrogen, Carlsbad, Calif.) according to manufacture's instructions. Briefly, cells grown in 6-well plates ($2.5\times10^5$ cells/well) were incubated with 4 μg of DNA IgG-Fc cDNAs using 10 microliter of transfection agents in serum- and antibiotic-free DMEM (Invitrogen). Six hours after transfection, the cultures were placed in the complete culture medium. The medium and the cells were separately harvested 48 hours after transfection. For large-scale expression of GLP-1/IgG-Fc fusion proteins, COS-7 cells grown in 150 mm dishes were transfected with 80 μg of relevant cDNA using cationic transfection reagent, Poly(ethyleneimine) (PEI, 25 kDa). Briefly, DNA and PEI were separately diluted in 150 mM NaCl, mixed and incubated for 20 min. The DNA/PEI complexes were added to cells and incubated for 6 h in serum- and antibiotic-free medium. The medium was replaced with DMEM, 10% FBS and 1% P/S. This method produces ~85% transfection efficiency.

To establish stable COS-7 cells expressing GLP-1/IgG-Fc, the cells grown in 6-well plates ($2.5\times10^5$ cells/well) were transfected with 4 μg of linearized GLP-1/IgG-Fc or IgG-Fc. Twenty four hours after transfection, the cells were split and cultured in DMEM containing G418 (500 μg/mL) for selection of those cells that had stably integrated the recombinant plasmid into their genome. Culture medium was replaced every 3 days until colonies were formed. Individual colonies were isolated and expanded to stable cell lines and tissue culture supernatant from these cell lines grown in 24-well plates were tested for fusion protein using a rat GLP-1 RIA kit (see below). The cells capable of secreting fusion protein were chosen for further characterization.

Example 3

Purification of GLP-1/IgG-Fc Fusion Proteins from Mammalian Cell Culture Medium

For mini-purification, the medium collected from the transfected cells (typically 2.5 mL from each well of a 6-well plate) was added to 70 μL (packed volume) pre-washed Protein G Sepharose 4 Fast flow resin (Amersham-Pharmacia, Piscataway, N.J.) in buffer containing 100 mM Tris pH 8.0 and 150 mM NaCl. After overnight incubation at 4° C. and extensive washing with the Tris buffer, proteins were eluted directly from the resin by 30 μL of SDS sample buffer.

To acquire larger quantities of the fusion proteins, midiscale purifications using Protein G sepharose columns employed 50 mL of conditioned culture media of COS-7 cells transfected with GLP-1/IgG-Fc-fusion vectors and grown in 15 cm dishes. Briefly, 50 mL of DMEM medium collected 48 hours post-transfection or from the cells stably expressing the fusion proteins were incubated with Protein G sepharose (1 mL packed volume, Amersham-Pharmacia). The incubations were performed overnight at 4° C. in the presence of 1% Triton X-100. After extensive washing with PBS containing 0.1% Triton X-100, and a final wash with 150 mM NaCl, proteins were eluted from the resin using 1 mL of 0.1 M glycine (pH 2.7). The elutions were immediately neutralized with Tris pH 9.0 buffer and the purified proteins were desalted using PD-10 columns (Amersham-Pharmacia) and eluted in PBS. As shown (FIG. 4A), a two-step elution approach allows removal of most of the fusion proteins from the sepharose column. A fraction of the samples were resolved by SDS PAGE and visualized by Coomassie Blue staining allowing for an estimation of production and purification yield (~6 μg/ml fusion protein in 2-day static culture when seeding at ~$1.25\times10^5$ cells/ml).

Example 4

Bacterial Expression of GLP-1/IgG-Fc Fusion Proteins

GLP-1/IgG-Fc fusion protein in *E. Coli* cells. In order to compensate for the codon bias in *E. Coli* BL21 cells, Rosetta gami 2 cells (Novagen, EMD biosciences, San Diego, Calif.) were used which allow enhanced disulphide bond formation and additionally harbor a plasmid for expression of seven rare tRNAs. After cells were transformed with GLP-1/IgG-Fc/pET28a or IgG-Fc/pET28a vectors (Novagen), several individual colonies were selected and screened for optimal expression of the fusion proteins. For protein expression, a single colony of bacteria was used to inoculate 50 mL of 2×YT (with kanamycin) medium and grown overnight at 37° C. The culture was then diluted into fresh medium (1:50) and grown to O.D$_{600}$ 0.6. The expression was induced with 1 mM IPTG (EMD) for 3 hr. The bacteria were harvested and the pellet was stored at −80° C. for further processing. To extract bacterial proteins, the pellets were resuspended in ice-cold PBS containing a protease inhibitor cocktail (Sigma, St. Louis, Mo.) and the cells were lysed by sonication. Proteins were solubilized using 1% Triton X-100 in PBS for 30 minutes. The centrifugation-clarified (12,000 g, 10 min) supernatant containing the fusion proteins was collected. The expressed proteins were purified using Protein G sepharose and analyzed using SDS-PAGE and Coomassie Blue staining (data not shown). About 120 microliter of GLP-1/IgG-Fc and Fc-only fusion proteins were purified from 4 Liters of bacteria culture.

Figure 4B:
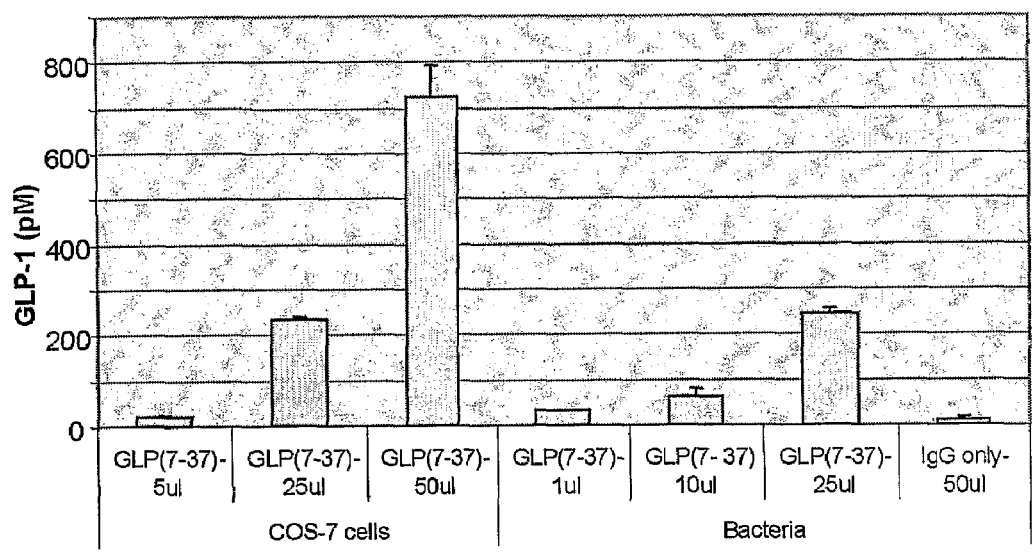
FIG. 4B shows GLP-1 expression in mammalian and bacterial cells. IgG-Fc fusion proteins expressed in COS-7 cells or bacteria (Rosetta gami 2) were purified using protein G sepharose. Varying amounts of purified protein were used for detection of GLP-1 protein using a total GLP-1 RIA kit.

Purified fusion proteins from mammalian and bacterial sources were further evaluated in a total GLP-1 RIA to confirm GLP-1 expression. A peptide dose-dependent increase in GLP-1 levels was observed with both mammalian and bacterial expressed GLP-1 fusion proteins. However, the expression levels of total GLP-1 were found to be lower in the bacteria than in the mammalian cells (FIG. 4B).

Example 5

Stable COS-7 Cells Secreting GLP-1/IgG-Fc Fusion Proteins

Figure 5:
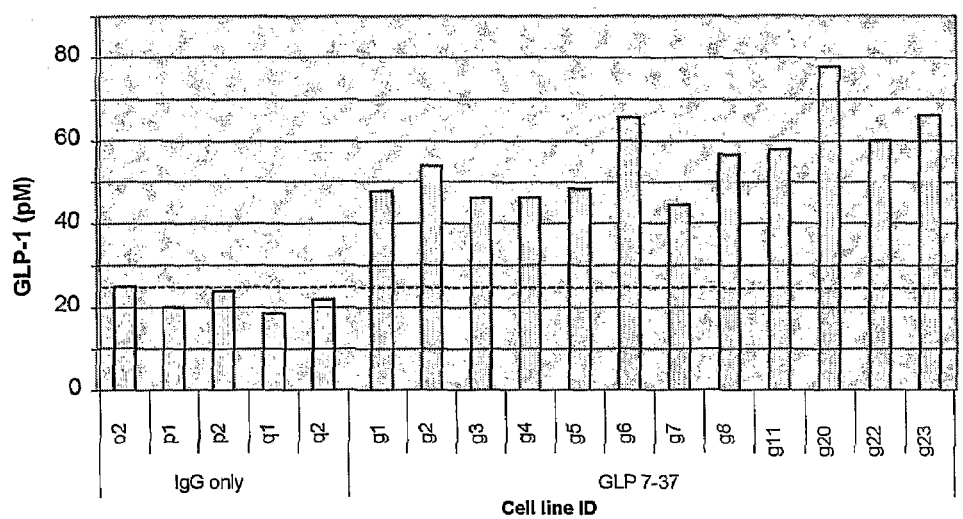
FIG. 5 shows the expression of GLP-1 in stably transfected COS-7 cells. COS-7 cells were transfected with GLP-1/IgG-Fc or IgG-Fc linearized plasmids and selected with 500 μg/mL of G418. After isolating potentially positive clones, the cells were grown in 12-well plates and medium was collected 48-h post-plating. The medium was used in total GLP-1 RIA assays to detect GLP-1 protein.

Stable COS-7 cells expressing GLP-1/IgG-Fc fusion proteins were established after selecting for G418 resistance and tested for GLP-1 secretion using a RIA. Total GLP-1 levels in the medium used to grow stable cells were used as a baseline to evaluate the expression levels in cells secreting GLP-1/IgG-Fc. As shown (FIG. 5), all the Fc-only stable cells secreted levels of GLP-1 lower than the medium baseline. We were able to isolate several clones expressing GLP-1/IgG-Fc fusion proteins which secreted GLP-1 at levels higher than the baseline (FIG. 5). However, the levels of secretion were low with less than a two-fold increase over baseline.

Example 5

In Vitro Characterization of GLP-1/IgG-Fc Fusion Proteins

Figure 6:
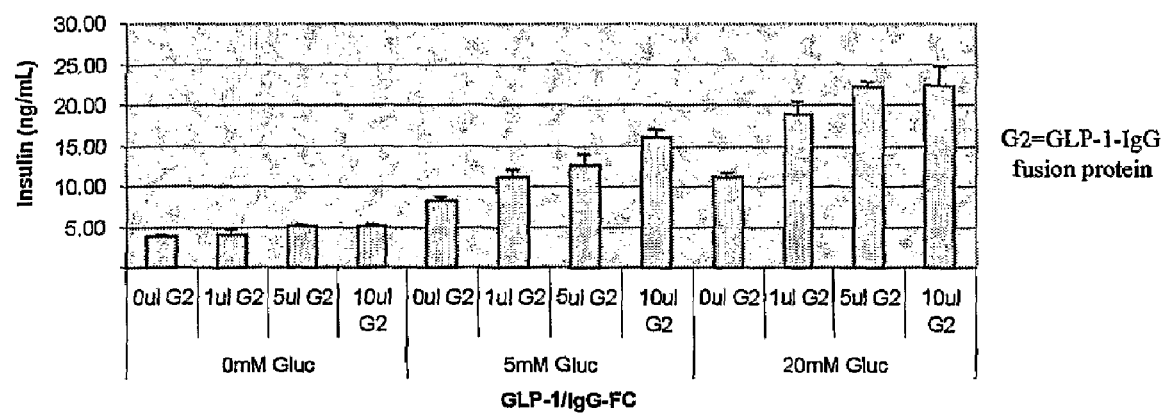
FIG. 6 shows the effect of GLP-1/IgG-Fc fusion treatment on insulin secretion in INS-1 cells. INS-1 cells were plated in 24-well plates and grown overnight. The cells were glucose- and serum-starved and treated with purified GLP-1/IgG fusion proteins for 1 h in KRB buffer with 0, 5 or 20 mM glucose. The medium was analyzed for insulin secretion using the insulin radioimmunoassay.

Native GLP-1 stimulates insulin secretion from beta-cells in a glucose-dependent manner (100). To evaluate whether the purified GLP-1/IgG-Fc fusion proteins from mammalian cells were functional, their effect on insulin secretion from clonal insulin-secreting INS-1 cells was determined. INS-1 cells were serum- and glucose-starved and were then treated with varying amounts of purified GLP-1/IgG-Fc fusion protein in the presence of 0, 5 or 20 mM glucose as indicated. As shown (FIG. 6), GLP-1/IgG-Fc did not stimulate insulin secretion from the beta-cells in the absence of glucose. However, in the presence of 5 mM or 20 mM glucose, the GLP-1/IgG-Fc stimulated insulin secretion from the beta-cells in a dose-dependent manner. The data indicates that the GLP-1/IgG-Fc fusion proteins are biologically active and are capable of stimulating insulin secretion in INS-1 cells in a glucose-dependent manner.

Example 8 cAMP Induction by GLP-1/IgG-Fc Fusion Peptides

Figure 7:
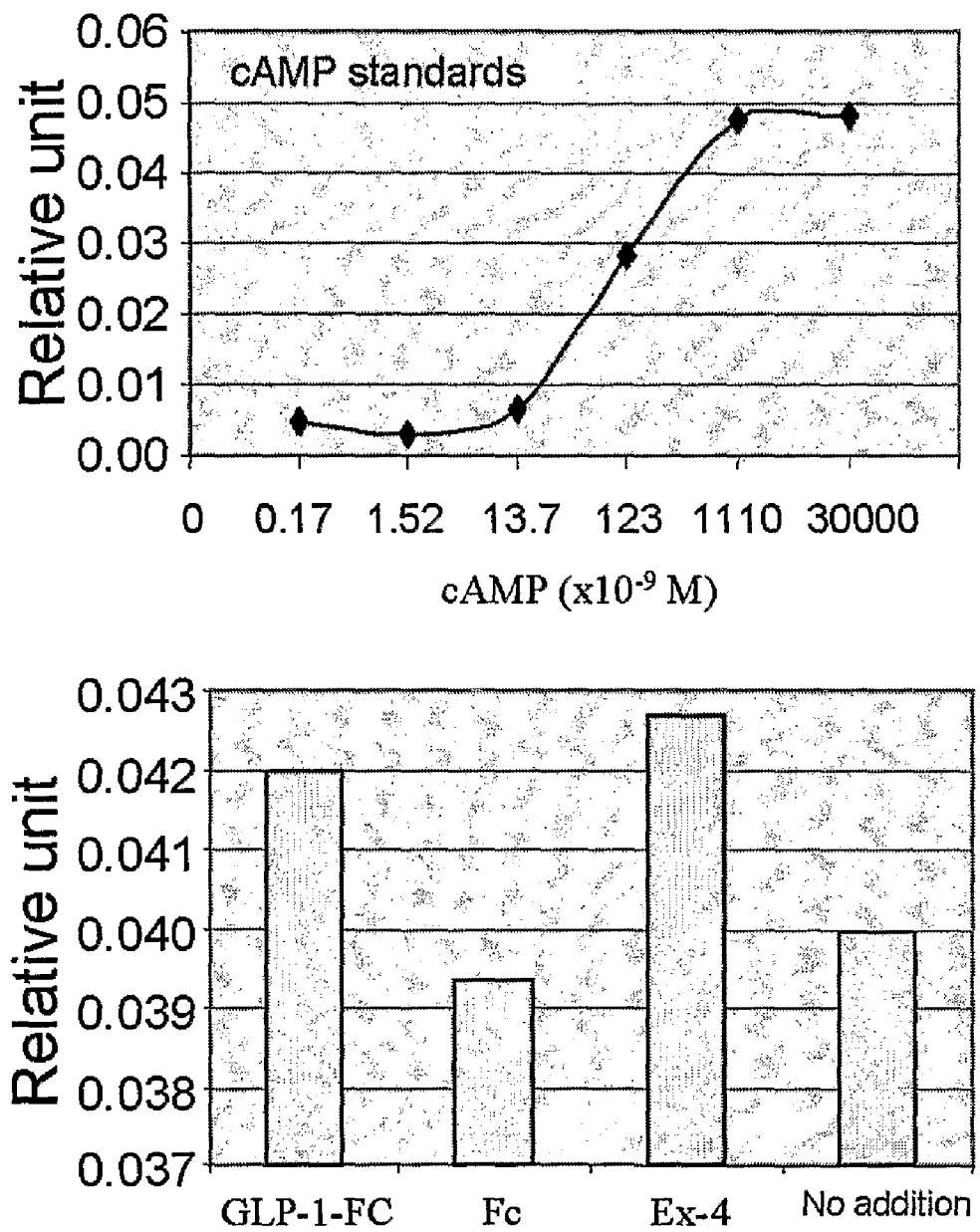
FIG. 7 is a graph demonstrating that GLP-1/IgG-FC exhibits similar efficacy as Ex-4 in generating cAMP in INS-1 cells. INS-1 cells were plated in 24-well plates and grown overnight. The cells were glucose- and serum-starved and treated with purified GLP-1/IgG-Fc fusion protein (IgG-Fc- and Ex4 as the negative and positive controls) for 10 min in serum-free RPMI medium with 0 or 5 mM glucose. cAMP levels in lyophilized aliquots of cell extracts were measured by radioimmunoassay.

In the absence of glucose, cAMP levels from the INS-1 cells treated with GLP-1/IgG-Fc (120 nM) were at basal levels (FIG. 7). However, in the presence of 5 mM glucose, the cAMP levels of GLP-1/IgG-Fc treated cells were significantly increased to a level that is comparable to that of cells treated with Ex4 (FIG. 7). The results indicate that GLP-1/IgG-Fc-stimulated cAMP generation in INS-1 cells is glucose concentration dependent.

Example 8

GLP-1/IgG-Fc Treatment Prevents the Onset of Diabetes in db/db Mice (Type II Diabetes Model)

4-week old female db/db mice (BKS.Cg-m+/+Lepr$^{db}$, stock number 000642) were purchased from Jackson Laboratories (Bar Harbor, Me., USA). Mice were housed under controlled light (12 hours light/12 hours dark) and temperature conditions, and had free access to food (normal rodent chow) and water. All procedures were conducted in accordance with the guidelines of the Canadian Council on Animal Care and were approved by the University of Toronto Animal Care Committee.

The diabetic db/db mice were treated by DNA injection/electroporation as previously described (Prud'homme and Chang, Gene Ther. 1999; 6(5):771-777) to enhance gene transfer. Briefly, anesthetized mice were injected in the tibialis anterior muscles with 50 μg of either GLP-1/IgG-Fc or IgG-Fc plasmids in PBS using a 27-gauge needle fitted with a plastic collar limiting muscle penetration to approximately 5 mm. The muscles were electroporated using electrodes fitted to a pair of calipers with three 100V square wave pulses (1 sec apart). In all mice, a second injection was administered 2 weeks after the first injection. The animals were monitored for bodyweight and fasting blood glucose weekly, and saphenous vein bleedings were collected prior to injection and 2 weeks and 12 weeks after the first injection for measurement of fasting insulin and glucagon levels. Blood was taken from the saphenous vein under fasting conditions at 4, 6 and 32 weeks after the DNA injection. The fasting blood glucose levels were measured using One Touch Basic glucose meter (Lifescan Canada, Burnaby, British Columbia, Canada), and the GLP-1, insulin and glucagon levels were measured as described below.

Expression of the GLP-1/IgG-Fc fusion protein was evaluated by measuring plasma levels of active GLP-1 using a GLP-1 Elisa kit (Linco). As shown, 2 weeks after the first injection the plasma GLP-1 levels were significantly elevated in mice injected with GLP-1/IgG-Fc compared to those mice injected with IgG-Fc vectors. The plasma GLP-1 levels returned to near basal levels 16 weeks after the first injection (FIG. 8A).

During the course of treatment, the bodyweight of mice in the two groups was not found to be significantly different (not shown). During the first month after injection, the fasting blood glucose levels were not significantly different between the two groups of mice (not shown). However, 12 weeks post-injection, the fasting blood glucose levels of the GLP-1/IgG-Fc producing mice were significantly lower (P<0.001) than the control mice (FIG. 8B). Furthermore, while the fasting insulin levels were found to be significantly elevated in the GLP-1/IgG-Fc producing mice compared with the IgG-Fc control mice (P<0.05) (FIG. 8C), the fasting glucagon levels were lower in the GLP-1 group mice compared to the control mice (P<0.05) (FIG. 8D). In vivo expression of GLP-1/IgG-Fc had glucose lowering effects in the db/db mice, likely due to the enhanced insulin secretion and the reduced basal glucagon release.

Example 9

GLP-1/IgG-Fc Treatment Prevents the Onset of Diabetes in STZ-Induced Insulin Deficient Mice (Type I Diabetes Model)

Background control mice (C57BLKS/3) and CD1 mice were obtained from Charles River Canada (Montreal, QC, Canada) at the same age. Mice were housed under controlled light (12 hours light/12 hours dark), temperature AND specific pathogen-free conditions, and had free access to food (normal rodent chow) and water. Female NOD mice were purchased from Taconic Farms (Germantown, N.Y.). NOD mice were fed ad libitum with a regular chow, i.e., Charles River #5075 autoclaved chow. All procedures were conducted in accordance with the guidelines of the Canadian Council on Animal Care and were approved by the University of Toronto Animal Care Committee. The blood sugar levels of the mice were monitored weekly with Advantage Comfort™ strips and with an AccuSoft Advantage™ monitor (Roche Diagnostics, Laval, Quebec, Canada). Diabetes was diagnosed when the blood glucose level exceeded 17.0 mmol/L on two consecutive readings.

Recent studies suggest that the incretin function may be important in glycemic regulation in remission phase of type I diabetes (18). To address the effectiveness of our GLP-1/IgG gene therapy in a model of beta islet-cell injury, we studied its effects in streptozotocin (STZ)-induced diabetes in CD1 mice. Vectors encoding GLP-1/IgG-Fc, Ex4-Fc or Fc (50 microliter/mice) were intramuscularly injected into CD1 mice and gene transfer was enhanced by local electroporation as previously described (116). Seven days after DNA injection, the mice were received STZ (55 mg/kg, i.p.) daily for consecutive 5 days. Blood was taken from the saphenous vein under fasting conditions at 4, 6 and 32 weeks after the DNA injection. The fasting blood glucose levels were measured using One Touch Basic glucose meter (Lifescan Canada, Burnaby, British Columbia, Canada), and the GLP-1, insulin and glucagon levels were measured as described below.

The blood glucose of the Fc-control mice rose markedly, reaching diabetic levels ($\geq 17$ mM) with a few days, but the GLP-1/IgG-Fc (or Ex4-Fc) mice were protected and displayed a low incidence of overt diabetes (FIG. 9). Pancreatic histological studies demonstrated that destruction of islet beta-cells occurred in both group mice, but the extent of damage was found to be lower in GLP-1/IgG-Fc (or Ex4-Fc) mice (FIG. 9). Infiltration of the islets by mononuclear cells (lymphocytes and/or macrophages) was observed in both groups mice (not shown). Interestingly, Ex4-Fc treatment yielded a result similar to GLP-1/IgG-Fc, even though EX4-Fc is expected to resist DPPIV degradation. These findings indicate that expression of GLP-1/IgG-Fc (or Ex4-Fc) protected against the STZ-induced beta-cell damage in spite of the presence of islet inflammation (insulitis).

Example 10

In Vivo Expression of GLP1/IaG-Fc and its Effect on Blood Glucose in Pigs

GLP-1/IgG$_1$-Fc or control IgG$_1$-Fc vectors (4 mg/pig) were muscularly injected into male Yorkshire pigs (23 kg) followed by electroporation using ADViSYS electroporator. Three days after injection, Alloxan monohydrate (80 mg/kg, Sigma) was administered in 25 ml saline intravenously under general anesthesia by Fluorotan. Initially, the acidic Alloxan solution was neutralized before injections, Alloxan causes hyperglycemia. However, neutralized solution did not effectively cause hyperglycemia and thus subsequent injections were performed without neutralization which induced moderate hyperglycemia in the blank IgG-Fc injected pigs but not in the pigs injected with GLP-1/IgG-Fc vectors. The fasting blood glucose was tested twice a week in ketamine-sedated pigs when blood samples were withdrawn using a glucometer (FIG. 10A) and the expression of the Fc proteins were determined using ELISA (FIG. 10B).

Example 11

DNA Covaccination with PPI/Gad65 and B7.1-wa to Induce Tolerance to Islet-Cell Antigens with or without Administration of GLP-1/IgG-Fc To assess whether the regenerative effects of the GLP-1/IgG-Fc fusion protein will induce remission and result in the induction of regulatory T-cell activity in vaccinated mice that are already diabetic, combination therapy of a GLP-1/IgG-Fc gene transfer and PPI/GAD65 DNA was used to treat NOD mice. NOD mice were treated with combination gene therapy of a DNA vaccine to induce tolerance and a GLP-1/IgG-Fc fusion construct to ameliorate autoimmune diabetes. In these studies an Ins-GAD DNA vaccine (pIns-GAD plasmid) was a source of the antigen. The properties of this vaccine are described in a review (131). This vaccine has produced highly encouraging results in previous DNA vaccination experiments (131). The DNA vaccine encodes all the antigenic determinants of two key target molecules in type I diabetes, i.e., preproinsulin and GAD65. The vaccine was coadministered with a second plasmid, pB7-1wa, encoding a selective CTLA-4 ligand (B7-1wa, a mutated B7-1 molecule), as previously described. Gene transfer was enhanced by in vivo electroporation. Electroporation is used because it greatly increases gene transfer and might be required in humans and large animals, where i.m. gene transfer is less efficient than in rodents (53).

DNA was administered using a method previously described (130). NOD mice were purchased from Taconic Farms (Germantown) or bred in our facility as required. Studies were performed only with female NOD mice. NOD scid mice were obtained from Jackson Laboratory. Naked plasmids were injected i.m., followed by local electroporation as previously disclosed (113). Briefly, anesthetized mice were injected with 25 microgram of DNA in each tibialis anterior muscle (total of 50 microgram DNA). Immediately after the injection of DNA, local electroporation was performed by applying eight pulses at 200 V/cm and 20 msec duration, with an Electro Square Porator model ECM830, using a caliper-type electrode (Genetronics Inc., San Diego, Calif.) applied to the overlying skin coated with conductive gel. The injections were repeated four more times with a three to four weeks interval.

Female NOD mice (prediabetic or diabetic, see below) were subdivided into groups ($n \geq 20$) treated with the following VR1255-derived plasmids (covaccination with two plasmids):
a. pIns-GAD+pB7-1wa DNA covaccine (coinjection at same muscle site);
b. pGLP-1/IgG-Fc (or mutated DPPIV-resistant GLP-1/IgG-Fc variant pGLP-1A8G-Fc)
c. pIns-GAD+pB7-1wa DNA covaccine (as above in a.), and either pGLP-1/IgG-Fc or pGLP-1A8G-Fc (different muscle site)
d. Control groups will include mice receiving no vector, blank vectors, or either pB7-1wa, pIns-GAD, or pFc alone.

Unless stated otherwise, the mice received two cycles of injection, i.e., the initial vaccine and a booster injection (exactly the same as the first injection) applied 3 to 4 weeks later. The properties of VR1255 (optimized for i.m. gene delivery) are described in previous publications. All mice received the same amount of plasmid DNA to control for CpG-related effects, and this was done by adding empty plasmid as required.

In all experiments, NOD mice were followed for 15-30 weeks after the initiation of treatment (DNA covaccination GLP-1/IgG-Fc gene therapy), and responses to treatment tested as follows: 1) Glucose homeostasis (oral glucose tolerance test, every 4 weeks) and incidence of overt diabetes (blood glucose level exceeding 17 mM on three consecutive tests over a 7 day period). 2) After killing the mice: histological grade of insulitis; analysis of beta-cell mass, pancreatic insulin content, apoptotic/necrotic islet cell numbers and islet cell proliferation (from prior BrdU labeling). Severity of insulitis was scored as described (130). 3) In vitro response to islet antigens of T cells from the spleen, lymph nodes draining inoculated muscles, or peri-pancreatic lymph nodes: a) Antigens included insulin (porcine or bovine), GAD65 peptides as disclosed previously (130), HSP60, chicken OVA, or whole islet cells. b) Cultures and assays (including source and amount of antigen) were performed as described (113; 130) to determine proliferation by $^3$H-thymidine incorporation and cytokine secretion (IL-4, IL-10, IFNγ, TGF-β1). This establishes the level of responsiveness as well as the possible bias to a: Th1 type (high IFNγ, low IL-4); Th2 type (low IFNγ, high IL-4); Th3 type (high TGF-β1); or Tr1 type (high IL-10, low IL-4) pattern of cytokine production. Cytokines were measured in culture supernatants with ELISA assays as previously discussed. Our experience, in accord with a workshop report (132), is that cytokine secretion (particularly IFNγ) is a more sensitive indicator of anti-insulin or anti-GAD responses than proliferation.

Figure 17:
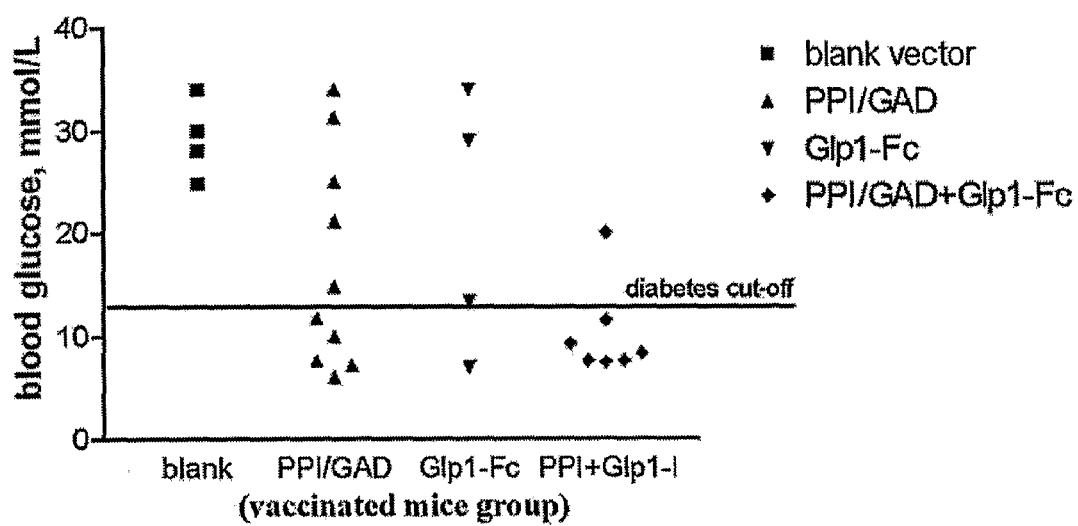
FIG. 17 shows the effects of in vivo expression of GLP-1/IgG-Fc and pre-proinsulin(PPI)-GAD65 vaccine on the onset of diabetes in NOD mice. NOD mice at age between 15 to 25 weeks were muscularly injected with plasmid(s) followed by electroporation. The injection was repeated twice with one-week interval. Blood glucose was monitored on weekly basis using glucometer. The vectors used were: PPI/GAD65, GLP-1/IgG-Fc, or the combination of the two. The amount of DNA injected were (50 µg individual DNA/mouse per injection. To equilibrate the amount of DNA when single vectors were injected, they were mixed with equal amount of the blank VRnew vector. The mice responding to the vector injection decreased the level of their blood glucose. The shown represents the blood glucose levels of the mice at three weeks after the injections. Similar results were obtained at ten weeks after the injections.

A representative experiment showing the effects of in vivo expression of Glp-1/IgG-Fc and pre-proinsulin(PPI)-GAD65 vaccine on the onset of diabetes in NOD mice is shown in FIG. 17. NOD mice at age between 15 to 25 weeks were muscularly injected with plasmid(s) followed by electroporation. The injection was repeated twice with one-week interval. Blood glucose was monitored on weekly basis using glucometer. The vectors used were: PPI/GAD65, GLP-1/ IgG-Fc, or the combination of the two. The amount of DNA injected were (50 μg individual DNA/mouse per injection. To equilibrate the amount of DNA when single vectors were injected, they were mixed with equal amount of the blank VRnew vector. The mice responding to the vector injection decreased the level of their blood glucose. The shown represents the blood glucose levels of the mice at three weeks after the injections.

Wild-type murine GAD65 cDNA, provided in the Bluescript KS+ vector, was a generous gift of Dr. H. McDevitt (Stanford University, Stanford, Calif.). Full-length PPIns I, generated as previously described (113) but without a stop codon, and full-length GAD65 were fused by overlapping PCR, performed as we have described (116; 128). This produced a cDNA segment in the order 5'-PPIns-GAD65-3', denoted Ins-GAD, which was inserted into compatible restriction sites of the VR1255 expression plasmid (129) (Vical Inc., San Diego, Calif.), from which the original cDNA luciferase segment had been deleted. The resulting plasmid is denoted VR-Ins-GAD. Transient transfection of COS-7 cell with VR-Ins-GAD resulted in the secretion of an Ins-GAD hybrid molecule in culture medium, as determined by immunoblotting performed as we have described (130). Similarly, i.m. injection of this vector, with electroporation, resulted in the production of Ins-GAD by local muscle cells, as determined by both immunoblotting and ELISA assay of extracted proteins (not shown), which were obtained from transfected muscle as we have previously described (128). The empty VR1255-derived plasmid (denoted VR) was used as a control in these experiments. We have previously described the properties of VR-B7-1wa (112; 113), which encodes a B7-1 molecule with a single tryptophan to alanine substitution at position 88 (110; 111). These VR1255-derived plasmids have human cytomegalovirus (CMV) immediate-early enhancer/ promoter (IE-EP) elements, CMV intron A, and a rabbit β-globin terminator sequence.

Figure 11:
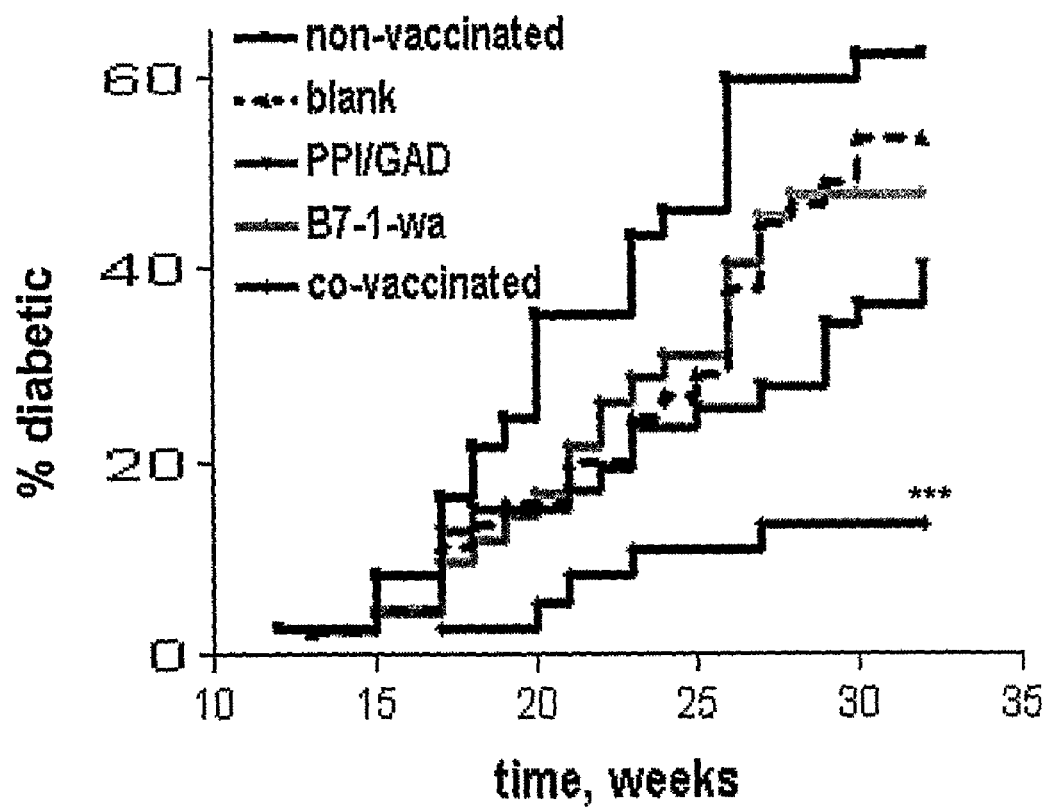
FIG. 11 shows that co-vaccination with PPI/GAD and B7.1-wa prevented autoimmune diabetes more efficiently than each of the components separately. Incidence of diabetes in all groups is compared to the incidence in the blank-injected group. The data is representative of two independent experiments.

As can been seen from FIG. 11, covaccination with a DNA vaccine in newly diabetic NOD mice improved glucose homeostasis, and induced complete remission in approximately 32% of the mice, compared to <5% remission in all other control groups (p<0.01 versus mice receiving control vectors).

Example 12

Adoptive Transfer of Diabetes in NOD-Scid Mice

Figure 12:
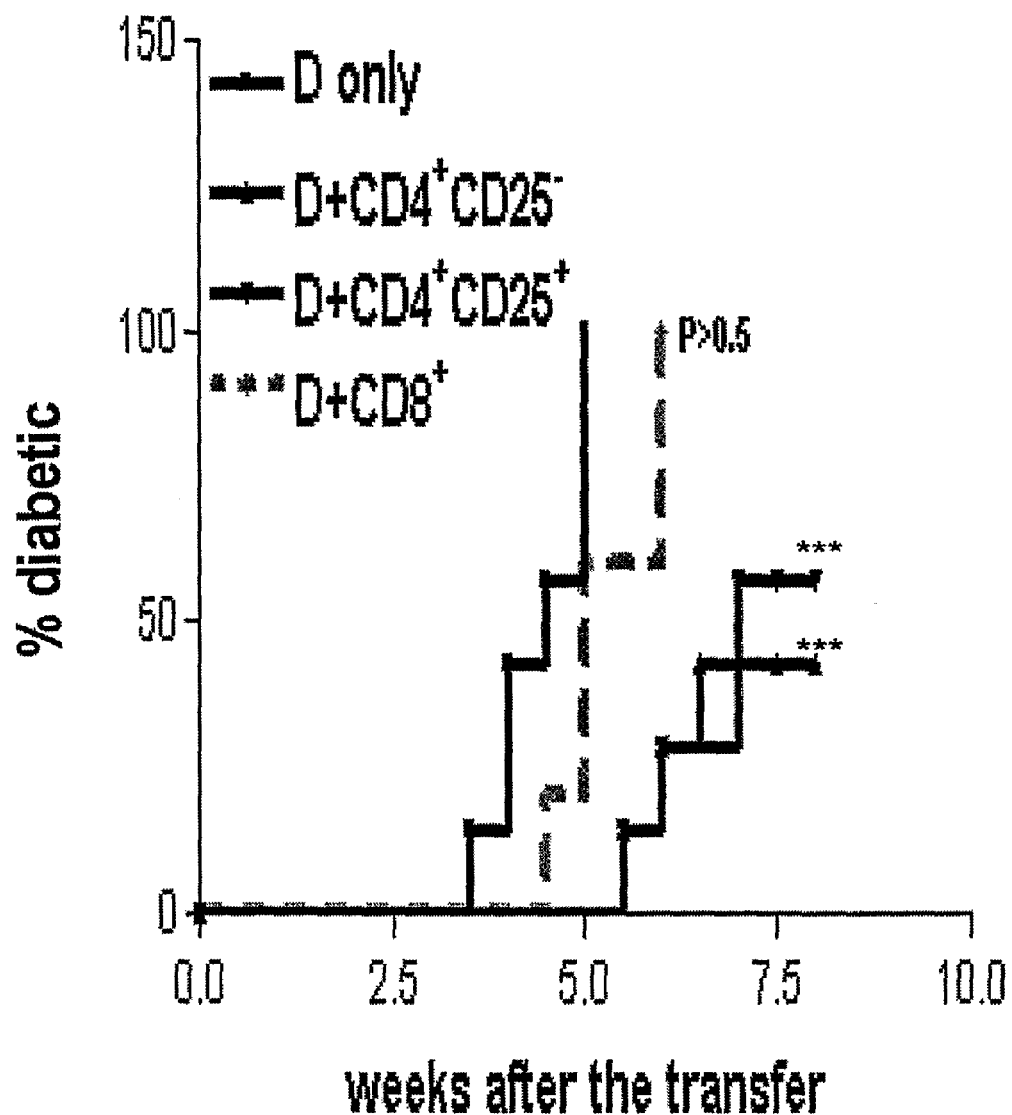
FIG. 12 shows the adoptive transfer of pre-sorted subsets of spleen cells from the co-vaccinated mice prevented autoimmune disease induced by transfer of diabetogenic spleen cells (D) in NOD scid mice. Spleen cells from co-vaccinated mice were sorted into CD4+ and CD8+ fractions by negative sorting as described above. CD4+ cells were further sorted into CD25+ and CD25− fractions. Diabetogenic cells were mixed with either CD4+ CD25+ or CD4+ CD25− cells in a ratio 200:1, and with CD8+ cells in a ratio 70:1. Incidence of diabetes in all groups is compared to the incidence in the group, which received only diabetogenic cells.

To determine if suppressive regulatory cells are generated by DNA co-vaccination with PPI-GAD65 and B7-1wa, adoptive transfer experiments were performed using NOD-scid mice. In this experiment, adoptive cotransfer of diabetogenic effector T cells from diabetic NOD mice with regulatory cells from DNA vaccinated NOD mice into NOD-scid/scid mice was performed. Spleen cells from co-vaccinated mice were sorted into CD4+ and CD8+ fractions by negative magnetic sorting as discussed below. CD4+ cells were further sorted into CD25+ and CD25− fractions as discussed below. Diabetogenic cells were mixed with either CD4+ CD25+ or CD4+ CD25− cells in a ratio 200:1, and with CD8+ cells in a ratio 70:1. As can be seen in FIG. 12, the adoptive transfer of pre-sorted subsets of spleen cells from co-vaccinated mice prevented the autoimmune diabetes induced by the transfer of diabetogenic spleen cells into the NOD-scid mice.

Example 13

Antigen Mediated IFN-V Release by Diabetogenic Cells

Figure 13:
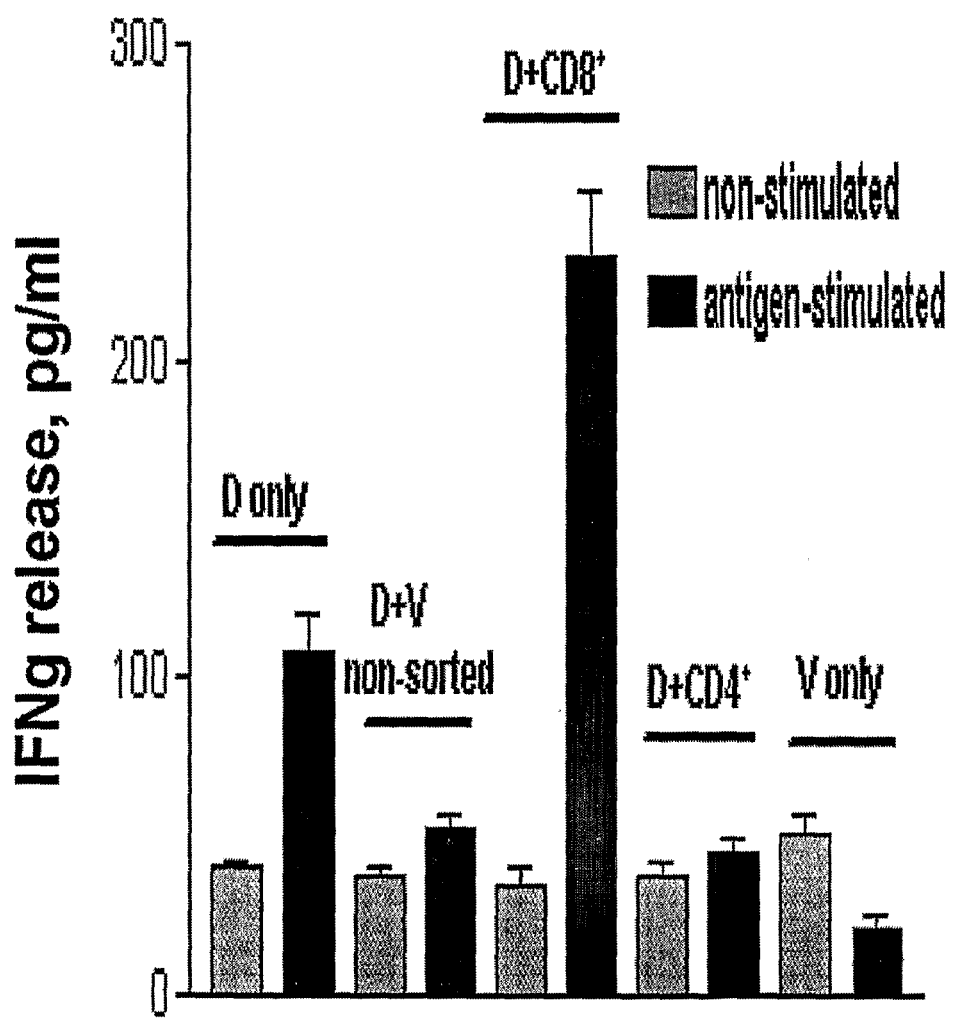
FIG. 13 shows that antigen-stimulated IFNγ release by diabetogenic cells (D) was suppressed in vitro by spleen cells from the co-vaccinated mice (V). Only CD4+ but not CD8+ subset suppressed the response of the diabetogenic cells.

To determine whether antigens could mediate IFN-γ release, in vitro spleen cell stimulation experiments were performed. Spleen cell suspensions from individual DNA-immunized mice, after lysis of the red blood cells, were plated in serum-free chemically defined medium AIM V (Invitrogen Canada, Burlington, ON), supplemented with 0.05 mM 2-mercaptoethanol. Antigens were added to the culture medium at a final concentration of 0.05 mg/ml. An equimolar mixture of three GAD65 synthetic peptides (Sheldon Biotechnology Centre, McGill University) were prepared. These peptides were: TYEIAPVFVLLEYVTLKKMREIIGW-PGGSGD (amino acids 206-236) (SEQ ID NO:9); AAL-GIGTDSVILIKCDERGK (amino acids 290-309) (SEQ ID NO:10); and VPPSLRTLEDNEERMSRLSKVAP-VIKARMMEYGTT (amino acids 509-543) (SEQ ID NO:11). These peptide fragments cover most of the antigen determinants recognized by T cells, as summarized in the ref. 19. As can be seen in FIG. 13, antigen-stimulated IFNγ release by diabetogenic cells (D) was suppressed in vitro by spleen cells from the co-vaccinated mice (V). Only CD4+ but not CD8+ subset cells suppressed the response of the diabetogenic cells.

Example 14

Antigen Mediated IFN-γ Release by Diabetogenic Cells

Proliferation of diabetogenic cells was determined with the MTT assay as described (30). In brief, MTT solution was added to the cells in 96 well plate after 72 h of antigen stimulation in a final concentration of 1 mg/ml. The assay was performed in quadruplicates. After 4 h, the reaction was stopped with isopropanol, acidified with 0.04 M HCl. Dissolved product of MTT reduction was measured at 540 nm. Proliferation was evaluated as an increase in optical density of reduced MTT in the antigen-stimulated cells over the optical density in the non-stimulated cells, which was considered 100%.

Figure 14:
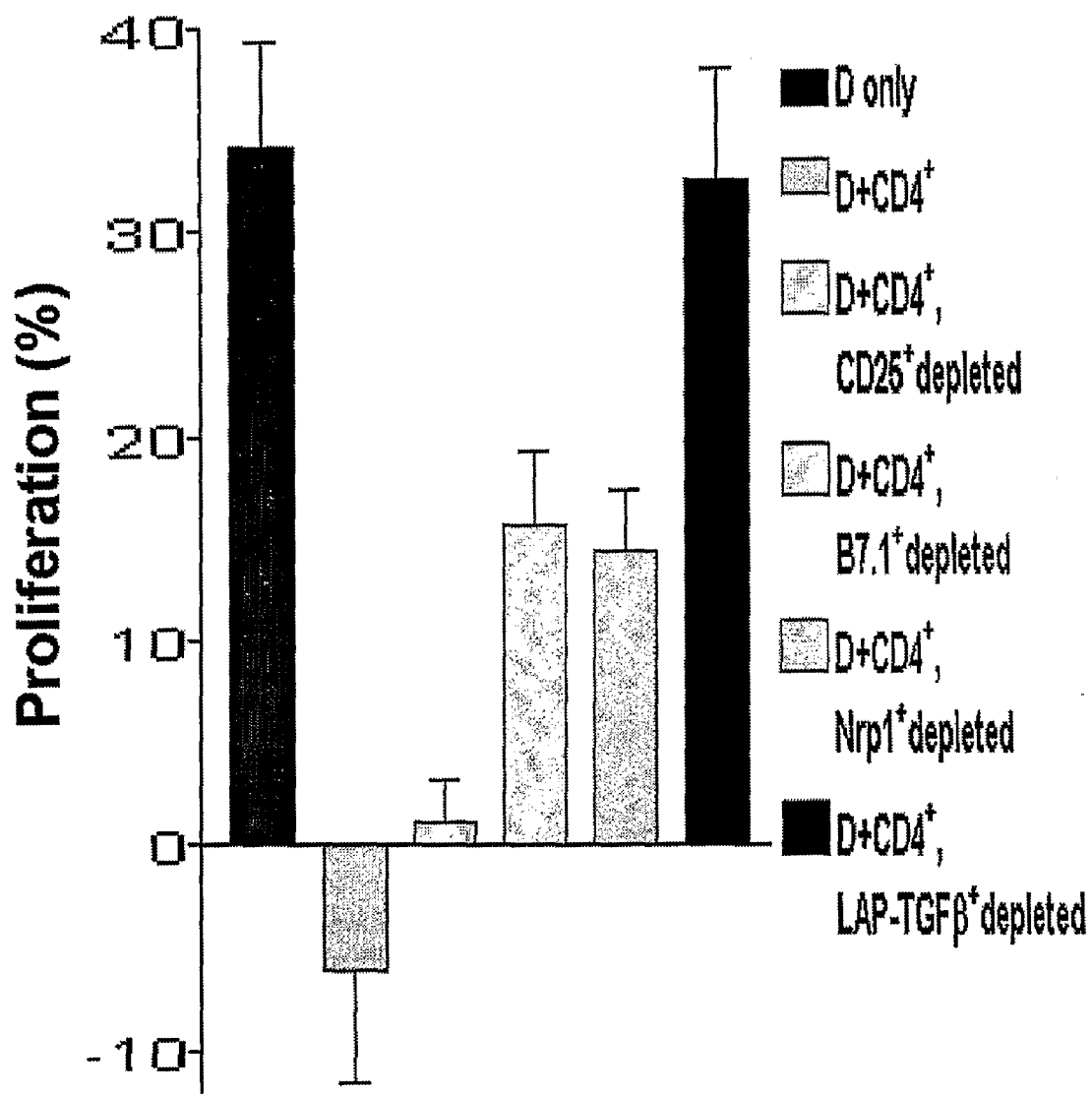
FIG. 14 shows that antigen-stimulated proliferation of diabetogenic cells (D) was suppressed by CD4+ B7.1+ fraction of total spleen cell suspension from the co-vaccinated mice; depleted of CD25+, B7.1+, Nrp1+, or LAP-TGF+ cells, the CD4+ fraction lost its suppressive power. Proliferation was evaluated by MTT test. The data, mean+/−SEM, are representative of minimum three independent experiments.

As can be seen in FIG. 14 antigen-stimulated proliferation of diabetogenic cells (D) was suppressed by CD4+ B7.1+ fraction of total spleen cell suspension from the co-vaccinated mice. When the suspension was depleted of CD25+, B7.1+, Nrp1+, or LAP-TGF+ cells, the CD4+ fraction lost its suppressive effect on diabetogenic cell proliferation.

Example 15

Suppression of Antigen Mediated IFN-γ Release by Diabetogenic Cells

Figure 15:
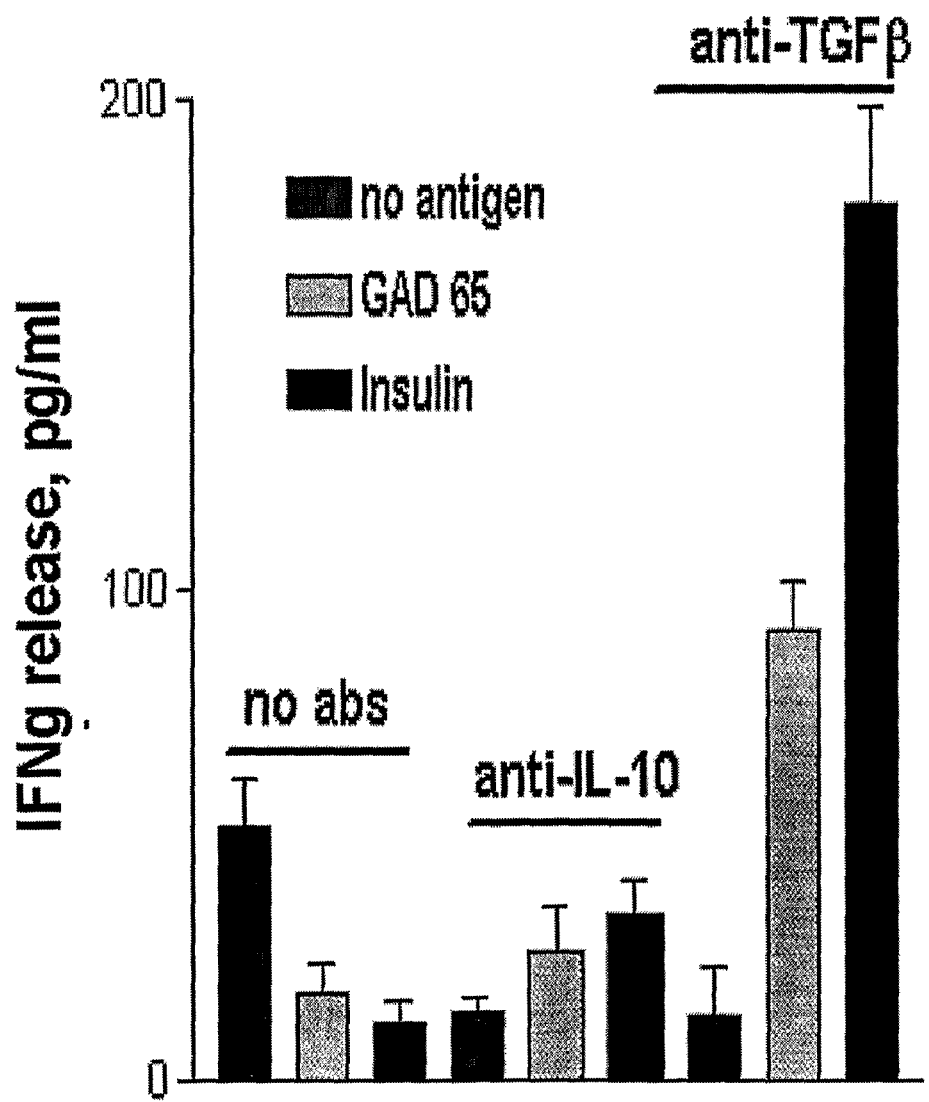
FIG. 15 shows that suppression of the antigen-stimulated release of IFNγ by diabetogenic spleen cells, caused by spleen cells from the co-vaccinated mice, was reversed by neutralizing anti-TGFβ, but not anti-IL-10 antibodies. The data, mean+/−SEM, are representative of minimum three independent experiments.
Figure 16:
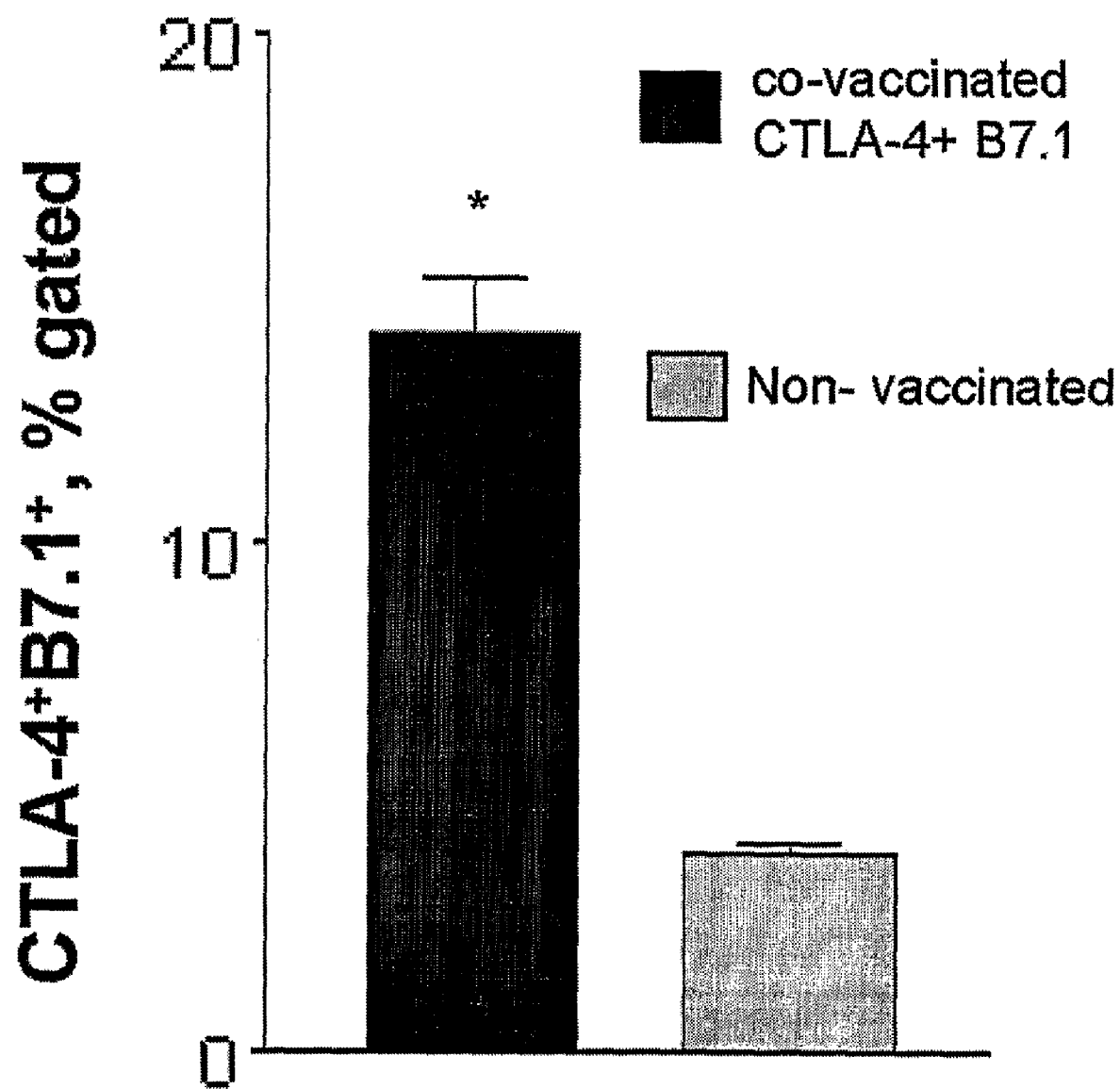
FIG. 16 is a graph that shows phenotype of the suppressor cells. CD4+ fraction of spleen cells from the co-vaccinated and non-vaccinated diabetic mice was purified by negative magnetic sorting to 95% purity and subjected to multicolor Flow Cytometry analysis. The bars represent the mean+/−SEM of the amount of the CD4+ cells expressing CD25, CD80 (B7.1), and CD152 (CTLA-4) below as found in the six to ten independent experiments. Dot plots were gated on the appropriate isotype controls.

To determine if antigen mediated suppression of IFN-γ release by diabetogenic cells caused by spleen cells isolated from co-vaccinated mice could be reversed, diabetogenic cells were treated with neutralizing anti-IL-10 or anti-TGFb antibodies. As can be seen in FIG. 15, the suppression of the antigen-stimulated release of IFNγ by diabetogenic spleen cells was reversed by neutralizing anti-TGFb, but not anti-IL-10 antibodies.

Example 16

Phenotyping of Suppressor Cells

CD4+ fraction of spleen cells from the co-vaccinated and non-vaccinated diabetic mice were purified by negative magnetic sorting to 95% purity and subjected to multicolor Flow Cytometry analysis. The bars represent the mean+/−SEM of the amount of the CD4+ cells expressing CD25, CD80 (B7.1), and CD152 (CTLA-4) as found in the six to ten independent experiments. Dot plots were gated on the appropriate isotype controls.

Example 17

Treatment of Pre-Diabetic Versus Diabetic Mice

It is much easier to induce tolerance in young NOD mice compared to older mice. For instance, it has been found that gene-based i.m. administration of regulatory cytokines or IFNγR/IgG1-Fc was more protective when begun at 3 weeks versus 6 weeks of age (105). Recent studies suggest that this may be due to either a decrease in Tr cell numbers (133) or a resistance of effector T cells to Tr-mediated suppression (104). Indeed, it is not unlikely that both factors are important. In the examples mentioned above, it was found that Tr cells could be induced by DNA vaccination of diabetic NOD mice and, furthermore, this was associated with remission in about 30% of mice, but only when mice were treated less than 2 weeks after the onset of disease. That the majority of mice remain diabetic is not surprising, since there may have been too much beta-cell loss prior to the initiation of this treatment.

Female NOD mice were inoculated with Ins-GAD/B7-1wa DNA covaccine, with or without pGLP-1/IgG-Fc, and include groups inoculated with control plasmids, as described above, beginning at 12 weeks of age in prediabetic mice and within one week of the diagnosis of diabetes (hyperglycemia≧17 mM on 3 consecutive readings in 7 days) in diabetic mice. We will analyze the response as described above. The goal is to determine whether DNA covaccination and/or GLP-1/IgG-Fc gene therapy will protect NOD mice at stages where insulitis is already prominent or sufficiently advanced to cause overt diabetes.

Example 18

Adoptive Transfer Experiments to Detect Regulatory T Cells

If suppressive regulatory cells are generated by DNA vaccination, then adoptive transfer of diabetes should be blocked. To analyze this question, we will perform adoptive cotransfer of diabetogenic effector T cells (from diabetic NOD mice) with putative regulatory cells (from DNA vaccinated NOD mice), as described by Balasa et al. (134) in NOD-scid/scid recipient mice. Splenic T cells (or defined subpopulations) from mice treated with Ins-GAD+B7-1wa protective plasmids, or control plasmids, will be injected alone, or mixed at various ratios with diabetogenic T cells, i.v. into NOD-scid/scid mice (n=15-20). It is expected that >90% of recipient mice of diabetogenic T cells (alone) will develop diabetes, as in our previous studies (FIG. 10-15), unless the disease transfer is prevented or ameliorated by co-transferring Tr cells. Prior to adoptive transfer, to identify Tr cells subpopulations, the cells will be fractionated into CD4+ CD25+, CD4+ CD25−, or CD8+ subtypes (magnetic sorting), followed by adoptive transfer of only one subpopulation of putative Tr cells with diabetogenic T cells. We have previously identified Tr cells in vaccinated NOD mice by this method (FIGS. 11-16). Thus, if the incidence of diabetes is depressed in these cotransfer experiments this will indicate that regulatory cells are present, and whether they belong to one of the 3 fractioned subtypes of cells.

Example 19

Analysis of Regulatory T Cell (Tr) Numbers and Function

Adoptive transfer experiments confirm the presence of Tr cells and provide an indication of their phenotype, but we will also examine the activity of specific subpopulations in vitro. Indeed, DNA vaccination may alter the numbers of Tr cells with recognizable phenotypes. Our previous studies show that vaccination produces Tr cells, of either CD25+ or CD25− phenotype, that frequently express CTLA-4, B7-1, LAP-TGF-beta, and Nrp-1, and we will examine these markers in the current proposal. Vaccination was also associated with an increase in Foxp3 (a Tr-associated marker), as determined by quantitative PCR. In future studies we will detect this nuclear antigen by immunostaining with a newly available mAb (eBioscience). Other relevant markers of Tr cells that we will examine include glucocorticoid-induced TNF receptor (GITR) and CD27 (135). We will determine the numbers of these cells by multi-color flow cytometry in the spleen and lymph nodes of NOD mice vaccinated with Ins-GAD+B7-1wa, or control vectors. GLP-1/IgG-Fc is not expected to directly influence T cell responses, because to our knowledge T cells do not express receptors for GLP-1. Nevertheless, we will include GLP-1/IgG-Fc therapy as an additional control in these experiments. To perform these studies, the mice will be terminated 3 weeks after 2 cycles of immunization (initial vaccination and 1 boost 3 weeks later). Tr cells will be enriched and tested in vitro for their ability to suppress islet antigen-stimulated T cells (see below). This will allow us to determine if the DNA vaccination procedure is increasing the number of phenotypic and functional Tr cells.

Example 20

In Vitro Regulatory T Cell (Tr) Assay

T cells of vaccinated or control mice were added in graded numbers in culture with spleen cells of newly diabetic NOD mice (diabetogenic T cells). The T cells of vaccinated or control mice were fractionated by FACS into populations that have a regulatory phenotype (e.g., CD4+ CD25+, CD4+ Nrp-1+, or CD4+ LAP-TGF-beta+), as previously done. Antigens will include insulin (porcine or bovine), GAD65 peptides as we described (130), HSP60, chicken ovalbumin (OVA), or whole islet cells. CD3 monoclonal antibody stimulation will also be included for assaying Tr activity. Suppressive effects on proliferation and IFNγ secretion were recorded and, in some wells, anti-cytokine antibodies were added to cultures to see if suppression is dependent on IL-4, IL-10 or TGF-β1.

To determine the persistence of Tr cells induced by DNA covaccination, in some experiments vaccinated mice were killed at various time points after the last DNA injection, i.e., 2, 4, and 6 months, and examined for Tr numbers and activity as described previously. The prolonged presence of Tr cells is of interest even in mice that become diabetic or remain diabetic, because Tr cells may be induced without fully protecting against autoimmune disease. For example, effector T cells

Example 21

Cytokine Secretion Assays

For the cytokine secretion assays, the cells were plated into 96 well plates, $5 \times 10^5$ cell per well. After 72 h in culture, the supernatants were pooled and frozen in single aliquots for the evaluation of IL-10, IFNγ, and TGF-β1 release. TGF-β1 was assayed after acidic activation of the conditioned medium (10 µL of 1 N HCl per 100 µl of the medium). ELISA kits from BD Biosciences (Mississauga, ON, Canada) were use to determine cytokine levels, as per the manufacturer's instructions.

Example 22

Cell Subpopulation Separation Assays

To separate cell subpopulations and regulatory T cell assays, CD4+ and CD8+ cells were purified from the total spleen cell suspension depleted of red blood cells, by negative magnetic sorting using Mouse CD4+ and CD8+ EasySep kits from StemCell Technology, Inc. (Toronto) as per manufacturer's instructions. The purity accessed by flow cytometry was 92-95%. CD4+ cells were further separated into CD25+ and CD25− subsets using Mouse Biotin Selection EasySep kit from the same company and biotinylated rat anti-mouse CD25 antibody (BD Pharmingen) according to the manufacturer's instruction with minor modifications. Similarly, biotinylated rat anti-mouse B7.1 (BD Pharmingen), biotinylated mouse anti-human/mouse LAP-TGFβ, and rabbit anti-rat/mouse Nrp1, conjugated with biotinylated goat anti-rabbit IgG (BD Pharmingen) were used with the same positive selection kit as above to deplete total CD4+ lymphocytes of the B7.1+, Nrp1+, or LAP-TGFβ cells. The separation was performed according to the manufacturer's instruction without modification. The purity of the product was accessed by flow cytometry as discussed below.

Example 23

Flow Cytometry Analysis

FITC- or PE-labeled rat anti-mouse CD4, CD25, CD 86 (B7.1), CD152 (CTLA-4), and isotype IgG were from BD Pharmingen. Non-labeled and biotinylated mouse anti-human/mouse LAP-TGFβ were from R&D Systems. Rabbit anti-rat/mouse neuropilin1 (Nrp1) polyclonal IgG was purchased from Oncogene. Anti-LAP-TGFβ and mouse isotype IgG were labeled with Alexa Fluor 488 (Molecular Probes) according to the manufacturer's protocol. Anti-Nrp1 IgG and rabbit normal IgG were labeled with Alexa Fluor 647. Because anti-Nrp1 antibodies contain 0.2% gelatin, swine gelatin was also labeled with Alexa Fluor 647, and this preparation was added to the isotype antibodies to the final 0.2% to correct for possible binding of labeled gelatin, a modified extracellular matrix protein, to lymphocytes.

Example 24

Detection of GLP-1/IgG-Fc Fusion Proteins by RT-PCR

Expression of IgG fusion transcripts were examined by using a one-step RT-PCR kit (Qiagen, Valencia, Calif.) using the gene specific primers. To detect GLP-1 fusion transcripts, 100 ng of total RNA from transfected COS-7 cells, and 0.6 micro-M of primers (5'-CCGGATATCGCCACCATG-GAGACAGACACACTCCTGCTATGGG-TACTGCTGCTCTGGGTTCCAGGTT CCACTGGTGAC-CATGCTGAAGGGACCTTTACCAGTG-3' (SEQ ID No: 21) and 5'-CGCGGATCCCTATCATTTACCAG-GAGAGTGGGAGAGG-3') (SEQ ID No: 22) were used, while 5'-CCGGATATCGCCACCATGGAGACAGACA-CACTCCTGCTATGGGTACTGCT-GCTCTGGGTTCCAGGTT CCACTGGTGACCCCAGC-GAGACCGTCACC-3' (SEQ ID No:19) and 5'-CGCGGATCCCTATCATTTACCAG-GAGAGTGGGAGAGG-3' (SEQ ID No:20) were used to detect IgG-Fc transcripts. The one-step RT-PCR conditions were 50° C. for 30 min, 95° C. for 15 min, 40 cycles of 94° C. for 30 sec, 55° C. for 30 sec and 72° C. for 60 sec followed by a 10 min extension at 72° C. The RT-PCR products were analyzed on a 1% agarose gel and visualized using ethidium bromide.

Example 25

Detection of GLP-1/IgG-Fc Fusion Proteins by SDS PAGE and/or Western Blotting Mini-scaled purified fusion proteins (30 microliter in SDS sample buffer) were resolved by 10% SDS-PAGE and transferred to a nitrocellulose membrane. The membrane was probed with anti-mouse antibody (1:5000, Amersham-Pharmacia) and visualized by ECL (Amersham-Pharmacia). An aliquot (30 microliter) of Midi-scale purified fusion proteins were separated by 10% SDS-PAGE and visualized by Coomassie Blue staining.

Example 26

GLP-1 Secretion Assay

Using the total (all forms) GLP-1 RIA kit (Linco), GLP-1 levels were determined from medium (150 µL) collected from COS-7 cells transiently or stably expressing GLP-1/IgG-Fc or IgG-Fc fusion proteins or from the lysates of bacteria expressing the fusion proteins. For in vivo detection, GLP-1 levels in serum from db/db mice were determined using an active GLP-1 ELISA kit (Linco).

Example 27

Insulin and Glucagon Secretion Assays

INS-1 cells were plated in 24-well plates at a density of $2.5 \times 10^5$ cells/well in RPMI 1640 medium containing 10% FBS. The following day the medium was replaced with fresh KRB buffer devoid of glucose for 2×30 min. The cells were then treated with 0, 5 or 20 mM glucose and various concentrations of purified GLP-1/IgG fusion proteins in KRB buffer for 1 hr. The insulin levels in conditioned KRB buffer (25 µL) were measured using a rat insulin RIA kit (Linco, St. Charles, Mo.). Plasma samples from db/db mice fasted for 16 h were measured for insulin and glucagon levels using a rat insulin RIA kit or rat glucagon RIA kit (Linco), according to the manufacturers instructions.

Measurement of cAMP: INS-1 cells were plated at 62,500 cells/well in 24-well plates. The cells were serum starved in SF-RPMI containing 100 µM IBMX for 5 h prior to treatment the following day. The cells were subsequently incubated with purified GLP-1/IgG-Fc-fusion peptides (120 nM) or Ex4 (100 nM) for 10 min in 450 μL of SF-RPMI medium. The assay was terminated by the addition of 1 mL of ice-cold ethanol. The extracts were incubated at −20° C. for 3 h to overnight following which 200 μL of the extracts were aliquoted and lyophilized. The lyophilized extracts were resuspended in 50 μL of sodium acetate assay buffer and used in cAMP RIAs (Biomedical Technologies, Stoughton, Mass.).

Example 28

Sample Protocols for Testing Fusion Proteins

Beta-cell mass analysis: Pancreatic sections (4 mm) were processed as previously described (Finegood et al., Diabetes. 2001; 50(5):1021-1029). Briefly, following dewaxing, dehydration and antigen retrieval (by boiling in citrate buffer), sections were incubated overnight at 4° C. with guinea pig anti-insulin antibody (Dako Diagnostics, Mississauga, ON, Canada). The samples were then incubated for 1 h with biotinylated anti-guinea pig antibody (Vector Laboratories, Burlington, ON, Canada), and subsequently treated for 1 h with avidin/biotin complex (Vectastain Elite ABC Kit; Vector Laboratories, Burlingame, Calif.). Sections were then stained with 3,3'-diaminobenzidine tetrahydrochloride (DAB; Sigma-Aldrich) for 10 min. After DAB staining, the sections are washed with tap water and counterstained with hematoxylin. Beta-cell mass from the insulin antibody-stained sections is measured using a Nikon (ECLIPSE-E1000) microscope connected to a video camera equipped with a color monitor and ImagePlus software, and the cross-sectional area occupied by all of the beta-cells and the cross-sectional area of all pancreatic tissue was quantified. Total beta-cell area and total pancreas mass for each animal were calculated as the sum of the determinations from each of the 8-10 segments of pancreas. A total of 1000-1500 beta-cells were counted per pancreas. Total beta-cell mass per pancreas was determined as the product of the total cross-sectional beta-cell area/total tissue area and the weight of the pancreas before fixation.

Islet beta-cell mass analysis. Islet cell mass, in particular the beta-cell mass, is used as an important criteria to evaluate islet beta-cell function (1; 3; 27). To examine the islet-mass from the GLP-1/IgG-Fc (or Ex4/IgG-Fc, or GLP-1A8G/IgG-Fc) mice or IgG-Fc mice (control) and untreated mice (as the second control), a modified protocol is used as we reported previously (3), in which the alpha-, beta- and delta-cells are sequentially stained using insulin, glucagon or somatostatin antibodies (1:1,000; DAKO) and relevant fluorescent secondary antibodies (DAKO). The cross-sectional area of all triple stained islet cells and the pancreatic tissue will be quantified using a fluorescent microscope equipped with a digital camera and ImagePlus software (NIH). Total islet mass per pancreas is determined as the product of the total cross-sectional triple stained islet cell area/total tissue area and the weight of the pancreas before fixation. Similarly, total beta-cell (or alpha) mass per pancreas was determined as the product of the total cross-sectional insulin positive-beta-cell (or alpha-cell) area/total tissue area and the weight of the pancreas before fixation.

Islet cell neogenesis: Islet cell neogenesis is evaluated as the product of the cross-sectional total numbers of small islet (including a single beta-cell or a cluster of 3-5 beta-cells)/total cross-sectional insulin positive-cell numbers as described previously (3).

Beta-cell proliferation and apoptosis is determined using BrdU and Tunel staining techniques as described (3). Briefly, pancreatic sections were dual stained for insulin and BrdU (anti-BrdU mouse IgG; Sigma) or Tunel (ApopTag Kit; Intergen). The BrdU$^+$ or Tunel$^+$ beta-cells is counted using a Nikon microscope (×1000) to obtain the percentage of BrdU$^+$ or Tunel$^+$ beta-cells. Since cytokine-induced beta-cell destruction is associated with necrosis, beta-cell necrosis is also determined using DAPI/propidium iodide staining as described previously.

Apoptosis assay: After treatment with the composition of the invention (0.5 to 24 hours), the apoptotic rate of isolated islet cells and/or insulin-secreting cell line (eg INS-1 cells and beta TC cells) was determined using APOPercentage Assay Kit (Biocolor Ltd. Ireland) according to manufacturers instructions. From the in vivo animal models, pancreas sections were obtained from subjects treated with or without the composition of the invention were double immunostained for insulin, as described above, and for fragmented DNA by Tunel assay, which detects fragmented nuclei characteristic of apoptotic cells. Tunel staining was performed using ApopTag Kit (Intergen, Purchas, N.Y.) according to manufacture's instruction. The islet tissue was identified as a red field for insulin staining (chromagen: New Fuchsin Substrate, DAKO), and apoptotic cells were identified by dark brown staining of nuclei (chromagen: 3,3'-Diaminobenzidine, Sigma). The results are expressed as the percentage of Tunel$^+$ beta-cells.

Oral Glucose Tolerance Test: Oral Glucose Tolerance Test was performed as described previously (3) to determine whether GLP-1/IgG-Fc treated mice improved insulin secretion and glucose utilization in vivo (3).

Pancreatic insulin content: Pancreatic insulin content was measured in pancreatic extractions using insulin RIA as previously described (3), in order to evaluate and compare the insulin storage of GLP-1/IgG-Fc (or Ex4-Fc, or GLP-1A8G-Fc) mice with control Fc-mice and untreated mice.

Pancreas perfusion: Pancreas perfusion was performed as we have previously described (3) to examine the insulin secretion from the islets of GLP-1/IgG-Fc (or Ex4/IgG-Fc, or GLP-1A8G-Fc) mice or IgG-Fc mice and untreated mice.

Receptor binding assay: The composition of the invention was iodinated by a classical Chloramines-T method (HUNTER and GREENWOOD, Nature. 1962; 194:495-496). The receptor binding assay is performed as described previously (Wang et al., Cell Physiol Biochem. 1998; 8(6):304-313): isolated islet cells and insulin secreting cells were suspended in PBS and centrifuged at 600 G for 10 min, and the cell pellets were resuspended in aliquots of PBS. The binding of the iodinated composition of the invention to the intact cells was carried out in 7×35 mm polystyrene tubes at 4° C. in 300 ml assay buffer (PBS containing 0.2% BSA) with the labeled compound (20,000 cpm) in the presence or absence of unlabelled composition of the invention. After 4.5 hours of incubation, when the assay system reaches an equilibrium state, cold PBS was added, and the samples were centrifuged for 10 min at 600 g at 4° C. The supernatant was discarded. After washing the cell pellets with cold PBS, the radioactivity was measured in a gamma counter.

cAMP determination: cAMP determination is a method that can evaluate the G-protein coupled receptor (GPCR) activation (Lee et al., Biochim Biophys Acta. 2000; 1490(3): 311-323). Intracellular cAMP levels were determined in isolated islet cells or cultured insulin-secreting cells cultured in 35 mm$^2$ dishes. They were preincubated in the buffer containing 130 mM NaCl, 5 mM KCl, 1 mM sodium phosphate, 1 mM MgSO$_4$, 2 mM CaCl$_2$, 20 mM HEPES buffer (pH 7.4), 6 mm glucose, and 0.1% BSA (RIA grade, Sigma) for 1 h. The PKA inhibitors were added for 20 min, and isobutyl methylxanthine (100 μM) for 10 min before addition of the compound for 20 min. Cells were washed three times in ice-cold PBS, cAMP extracted with hydrochloric acid (0.1M, 300 µl) and measured as per the cAMP RIAs (Biomedical Technologies, Stoughton, Mass.).

PI 3-kinase activity assay: PI3-kinase is upstream of Akt (Wang et al., Mol Cell Biol. 1999; 19(6):4008-4018). Whole cell lysates were obtained from isolated islet cells and insulin-secreting cell line (eg INS-1 cells and beta TC cells) pretreated with the composition of the invention for 20 min, and PI 3-kinase was immunoprecipitated using an antibody against the p85-regulatory subunit of PI 3-kinase (Santa Cruz Biotechnology). Activity was detected and quantified by measuring the formation of [$^{32}$P]PI 3-phosphate (Wang et al., Biochem J. 1998; 331 (Pt 3):917-928). Briefly, after overnight incubation with the antibody-coated beads, the bound protein was washed three times with buffer I (PBS containing 1% Nonidet P-40 and 100 µM Na$_3$VO$_4$), three times with buffer II (100 mM Tris-HCl (pH 7.5), 500 mM LiCl, and 100 µM Na$_3$VO$_4$), and finally three times with buffer III (Tris-HCl (pH 7.5), 100 mM NaCl, 1 mM EDTA and 100 µM Na$_3$VO$_4$). After washing, immunoprecipitates are resuspended in 50 µl buffer III with the addition of 10 µl 100 mM MgCl$_2$ and 10 µl PI (2 µg/ml). The samples sat at room temperature for 5 min before the addition of 10 µl ATP (ATP 440 µM with 30 µCi/10 µl [$^{32}$P]ATP). The samples were then shaken at room temperature for 10 min. The reaction was stopped by the addition of 20 µl 8 N HCl and 160 µl chloroform-methanol (1:1). The lipids were extracted by standard methods, dried down, resuspended in 20 µl chloroform-methanol (1:1), were separated on thin layer silica gel plates (pretreated with 10% w/v potassium oxalate) in a solvent system of chloroform-methanol-water-NH$_4$OH (60:47:11:2.2, vol/vol/vol/vol). Incorporation of $^{32}$P into PI 3-phosphate is detected by autoradiography, and activity was quantified using a Molecular Dynamics PhosphorImager System (Sunnyvale, Calif.).

Akt kinase assays: After treatment with the composition of the invention for 10 min, whole cell lysates were obtained from isolated islet cells and insulin-secreting cell line (eg INS-1 cells and beta TC cells), using lysis buffer containing 50 mM HEPES (pH 7.6), 150 mM NaCl, 10% (vol/vol) glycerol, 1% (vol/vol) Triton X-100, 30 mM sodium pyrophosphate, 10 mM NaF, 1 mM EDTA, 1 mM phenylmethylsulfonyl fluoride, 1 mM benzamidine, 1 mM Na$_3$VO$_4$, 1 mM dithiothreitol [DTT], and 100 nM okadaic acid (Wang et al., Mol Cell Biol. 1999; 19(6):4008-4018). Akt antibody is pre-coupled (16 hours) to a mixture of protein A- and protein G-Sepharose beads. These antibody-bead complexes are washed twice with phosphate-buffered saline (PBS) and once with lysis buffer (4° C.). Akt is immunoprecipitated by incubating 200 µg of total cellular protein with the anti-Akt-bead complexes for 2 to 3 h with constant rotation (4° C.). Akt immunocomplexes were washed four times with 1 ml of wash buffer (25 mM HEPES [pH 7.8], 10% [vol/vol] glycerol, 1% [vol/vol] Triton X-100, 0.1% [wt/vol] bovine serum albumin, 1 M NaCl, 1 mM DTT, 1 mM phenylmethylsulfonyl fluoride, 1 mM microcystin, and 100 nM okadaic acid) and twice with 1 ml of kinase buffer (50 mM Tris-HCl [pH 7.5], 10 mM MgCl$_2$, and 1 mM DTT). The immunocomplexes were incubated with constant agitation for 30 minutes at 30° C. with 30 µL of reaction mixture (kinase buffer containing 5 µM ATP, 2 µCi of [γ-$^{32}$P]ATP, and 100 µM Crosstide). Following the reaction, 30 µl of the supernatant was transferred onto Whatman p81 filter paper and washed four times for 10 minutes each time with 3 ml of 175 mM phosphoric acid and once with distilled water for 5 min. The filters were air dried and then subjected to liquid scintillation counting.

MAP kinase assay: After 20 min treatment with the composition of the invention, beta-cells were labeled with 1.25 microcurie $^{32}$Pi/group (NEN Life Science Products, Boston, Mass.) in phosphate-free RPMI medium without serum for 3 h at 37° C. The cells were harvested and placed in RPMI with 100 ng/ml LBP (PS-binding protein) and treated with the compositions of the invention for 30 min. After the incubation with the composition of the invention, the cells were stimulated with LPS for 15 min at 37° C. The cells were harvested, resuspended in lysis buffer (1% Nonidet P-40, 1% sodium deoxycholate, 0.1% SDS, 0.15 M NaCl, 0.01 M Na3PO4 (pH 7.2), 2 mM Na$_3$VO$_4$, 1 µM okadaic acid, 100 µg/ml PMSF, 50 µg/ml aprotinin, 10 µg/ml leupeptin, and 50 µg/ml pepstatin, all from Boehringer Mannheim), and sonicated. MEK was immunoprecipitated from the lysate, and the sample separated on a 10% SDS-PAGE discontinuous gel, and immunoblotting was performed using anti-phosphor-MEK antibody (Oncogene Research Products, San Diego, Calif.).

Statistical analysis: All data are presented as mean±SEM. Statistic analysis was performed using Student's t-test or analysis of variance (ANOVA) with 'n–1' post hoc custom hypotheses tests, as appropriate, with the SAS software (Statistical Analysis Systems, Cary, N.C.) or the GraphPad Prism 3.0 program (GraphPad Software Inc., San Diego, Calif.). The incidence of diabetes was plotted using the Kaplan-Meier method and statistical comparisons made with the log-rank test. The significance of differences in insulitis scores was determined with the Chi-squared test. The differences between groups in the in vitro proliferation and cytokine release assays were determined by analysis of variance (ANOVA). Significance was assumed at p<0.05.

Taken together, we developed a new method using beta-cell regeneration and DNA vaccination for control of immunity at same time for the prevention and treatment of type I diabetes. To this end, we developed specific GLP-1 analogue by fusing human GLP-1 (mouse and human GLP-1 are identical (12; 14) to a mouse IgG1-Fc derivative (forming GLP-1/IgG-Fc) to increase half-life, improve in vivo activity and reduce immunogenicity. The bivalent GLP-1/IgG-Fc fusion protein exists in native conditions. The fusion proteins displayed capacity to stimulate insulin secretion in a glucose-dependent manner and cAMP generation in Ins-1 cells. In in vivo studies using mice models, we were able to deliver this protein through a nonviral gene therapy approach, resulting in long-term expression of the fusion protein. This fusion protein has advantages including long-acting, potent and high ligand avidity, and immunological tolerance. This protocol has been partially proved by our in vivo studies in streptozotocin (STZ)-induced diabetes CD1 mice (a model of beta-cell injury) using GLP-1/IgG-Fc by gene therapy and in newly diabetic NOD mice by DNA vaccination of proinsulin, GAD65 and CTLA-4. The partial remission has been achieved respectively in each approach. It is expected that when using combination of two approaches a complete remission may be achieved.

In our studies of DNA vaccination, we found that Tr cells can be generated by DNA vaccination when delivery of the antigen gene is combined with a CTLA-4 (CD152) ligand. This covaccination approach was strongly protective against type I diabetes in NOD mice. It is conceivable that when combining this DNA vaccination with the gene therapy using GLP-1/IgG-Fc or its derivatives, a complete remission of diabetes in these NOD mice might have been seen.

It will be appreciated that the description above relates to the preferred embodiments by way of example only. Many variations on the computer system and methods for delivering the invention will be obvious to those knowledgeable in the field, and such obvious variations are within the scope of the invention as described and claimed, whether or not expressly described.

All references, including journal articles, patents and patent applications, in this application are incorporated by reference herein in their entirety.

TABLE ONE

The sequences of IgG-Fc, GLP-1 and/or Ex4, IgK, proinsulin and GAD65, B7-1 and its mutant form B7-1wa and its counterpart CTLA-4 (CD152) are as follows:

```
GLP-1                                                           (SEQ ID NO: 1)
HAEGTFTSDV SSYLEGQAAK EFIAWLVKGR-NH2

Ex4                                                             (SEQ ID NO: 2)
HGEGTFTSDL SKQMEEEAVR LFIEWLKNGG PSSGAPPPS-NH2

IgG-Fc                                                          (SEQ ID NO: 3)
PSETVTCNVA HPASSTKVDK KIVPRDCGCK PCICTVPEVS SVFIFPPKPK DVLTITLTPK
VTCVVVDISK DDPEVQFSWF VDDVEVHTAQ TQPREEQFNS TFRSVSELPI MHQDWLNGKE
FKCRVNSAAF PAPIEKTISK TKGRPKAPQV YTIPPPKEQM AKDKVSLTCM ITDFFPEDIT
VEWQWNGQPA ENYKNTQPIM NTNGSYFVYS KLNVQKSNWE AGNTFTCSVL HEGLHNHHTE
KSLSHSPGK

Human IgG2-Fc (788-1689) - cDNA:                                (SEQ ID NO: 4)
 788 gag cgcaaatgtt gtgtcgagtg cccaccgtgc ccaggtaagc cagcccaggc
 841 ctcgccctcc agctcaaggc gggacaggtg ccctagagta gcctgcatcc agggacaggc
 901 cccagctggg tgctgacacg tccacctcca tctcttcctc agcaccacct gtggcaggac
 961 cgtcagtctt cctcttcccc ccaaaaccca aggacaccct catgatctcc cggacccctg
1021 aggtcacgtg cgtggtggtg gacgtgagcc acgaagaccc cgaggtccag ttcaactggt
1081 acgtggacgg cgtggaggtg cataatgcca agacaaagcc acgggaggag cagttcaaca
1141 gcacgttccg tgtggtcagc gtcctcaccg ttgtgcacca ggactggctg aacggcaagg
1201 agtacaagtg caaggtctcc aacaaaggcc tcccagcccc catcgagaaa accatctcca
1261 aaaccaaagg tgggacccgc gggtatgag ggccacatgg acagaggccg gctcggccca
1321 ccctctgccc tgggagtgac cgctgtgcca acctctgtcc ctacagggca gccccgagaa
1381 ccacaggtgt acaccctgcc cccatcccgg gaggagatga ccaagaacca ggtcagcctg
1441 acctgcctgg tcaaaggctt ctaccccagc gacatcgccg tggagtggga gagcaatggg
1501 cagccggaga acaactacaa gaccacacct cccatgctgg actccgacgg ctccttcttc
1561 ctctacagca agctcaccgt ggacaagagc aggtggcagc aggggaacgt cttctcatgc
1621 tccgtgatgc atgaggctct gcacaaccac tacacgcaga agagcctctc cctgtctccg
1681 ggtaaatga Human IgG2-Fc (788-1689) - amino acid:                          (SEQ ID NO: 5)
ERKCCVECPPCPAPPVAGPSVFLFPPKPKDTLMISRTPEVTCVVVDVSHEDPEVQFNWYVDGVEVHNAKT
KPREEQFNSTFRVVSVLTVVHQDWLNGKEYKCKVSNKGLPAPIEKTISKTKGQPREPQVYTLPPSREEMT
KNQVSLTCLVKGFYPSDIAVEWESNGQPENNYKTTPPMLDSDGSFFLYSKLTVDKSRWQQGNVFSCSVMH
EALHNHYTQKSLSLSPGK IgK                                                             (SEQ ID NO: 6)
METDTLLLWV LLLWVPGSTG D Human Growth Hormone Reseasing Hormone (GHRH)
leader sequence:                                                (SEQ ID No: 7)
gtg ctc tgg gtg ttc ttc ttt gtg atc ctc acc ctc agc aac agc tcc cac
tgc tcc Proinsulin                                                      (SEQ ID NO: 8)
MALLVHFLPL LALLALWEPK PTQAFVKQHL CGPHLVEALY LVCGERGFFY TPKSRREVED
PQVEQLELGG SPGDLQTLAL EVARQKRGIV DQCCTSICSL YQLENYCN GAD65
                                                                (SEQ ID NO: 9)
1) TYEIAPVFVL LEYVTLKKMR EIIGWPGGSG D (amino acids 206-236);

(SEQ ID NO: 10)
2) AALGIGTDSV ILIKCDERGK (amino acids 290-309);

(SEQ ID NO: 11)
3) VPPSLRTLED NEERMSRLSK VAPVIKARMM EYGTT (amino acids 509-543).

B7-1 (CD80)                                                     (SEQ ID NO: 12)
MACNCQLMQD TPLLKFPCPR LILLFVLLIR LSQVSSDVDE QLSKSVKDKV LLPCRYNSPH
EDESEDRIYW QKHDKVVLSV IAGKLKVWPE YKNRTLYDNT TYSLIILGLV LSDRGTYSCV
VQKKERGTYE VKHLALVKLS IKADFSTPNI TESGNPSADT KRITCFASGG FPKPRFSWLE
NGRELPGINT TISQDPESEL YTISSQLDFN TTRNHTIKCL IKYGDAHVSE DFTWEKPPED
PPDSKNTLVL FGAGFGAVIT VVVIVVIIKC FCKHRSCFRR NEASRETNNS LTFGPEEALA
EQTVFL

CTLA-4 (CD152)                                                  (SEQ ID NO: 13)
MACLGLRRYK AQLQLPSRTW PFVALLTLLF IPVFSEAIQV TQPSVVLASS HGVASFPCEY
SPSHNTDEVR VTVLRQTNDQ MTEVCATTFT EKNTVGFLDY PFCSGTFNES RVNLTIQGLR
```

TABLE ONE-continued

The sequences of IgG-Fc, GLP-1 and/or Ex4, IgK, proinsulin and GAD65, B7-1 and its mutant form B7-1wa and its counterpart CTLA-4 (CD152) are as follows:

```
AVDTGLYLCK VELMYPPPYF VGMGNGTQIY VIDPEPCPDS DFLLWILVAV SLGLFFYSFL
VTAVSLSKM LKKRSPLTTG VYVKMPPTEP ECEKQFQPYF IPIN
```

Human Akt/Protein kinase B:                                (SEQ ID NO:14)
```
  1 mkterprpnt fiirclqwtt viertfhvet peereewtta iqtvadglkk qeeeemdfrs
 61 gspsdnsgae emevslakpk hrvtmnefey lkllgkgtfg kvilvkekat ayyamkilkk
121 evivakdeva htltenrvqq nsrhpfltrl kysfqthdrl cfvmeyangg elffhlsrer
181 vfaedrarfy gaeivsaldy lhseknvvyr dlklenlmld kdghikitdf glckegikdg
241 atmktfcgtp eylapevled ndygravdww glgvvmyemm cgrlpfynqd heklfelilm
301 eeirfprtlg peaksllsgl lkkdpkqrlg ggsedakeim qhrfftgivw qhvyekklsp
361 pfkpqvtset dtryfdeeft aqmititppd qddsmecvds errphfpqfs yspsata
```

Human MAP kinase:                                          (SEQ ID NO: 15)
```
  1 msdskcdsqf ysvqvadstf tvlkryqqlk pigsgaqgiv caafdtvlgi nvavkklsrp
 61 fqnqthakra yrelvllkcv nhkniislln vftpqktlee fqdvylvmel mdanlcqvih
121 meldhermsy llyqmlcgik hlhsagiihr dlkpsnivvk sdctlkildf glartactnf
181 mmtpyvvtry yrapevilgm gykenvdiws vgcimgelvk gcvifqgtdh idqwnkvieq
241 lgtpsaefmk klqptvrnyv enrpkypgik feelfpdwif pseserdkik tsqardllsk
301 mlvidpdkri svdealrhpy itvwydpaea eapppqiyda qleerehaie ewkeliykev
361 mdweerskng vvkdqpsdaa vssnatpsqs ssindissms teqtlasdtd ssldastgpl
421 egcr
```

Human caspase-3:                                           (SEQ ID NO: 16)
```
  1 mentensvds ksiknlepki ihgsesmdsg mswdtgykmd ypemglciii nnknfhkstg
 61 mtsrsgtdvd aanlretfrn lkyevrnknd ltreeivelm rdvskedhsk rssfvcvlls
121 hgeegiifgt ngpvdlkkit nffrgdrcrs ltgkpklfii qacrgteldc gietdsgvdd
181 dmachkipvd adflyaysta pgyyswrnsk dgswfiqslc amlkqyadkl efmhiltrvn
241 rkvatefesf sfdatfhakk qipcivsmlt kelyfyhl
```

PCR primers:
                                                           (SEQ ID No: 17)
5'-CCGGATATCGCCACCATGGAGACAGACACACTCCTGCTATGGGTACTGCTGCTCTGGGTTCCAGGT
TCCACTGGTGACCA-3'

(SEQ ID No: 18)
5'-TGCTGAAGGGACCTTTACCAGTG-3'

(SEQ ID No: 19)
5'-CCGGATATCGCCACCATGGAGACAGACACACTCCTGCTATGGGTACTGCTGCTCTGGGTTCCAGGT
TCCACTGGTGACCCCAGCGAGACCGTCACC-3'

(SEQ ID No: 20)
5'-CGCGGATCCCTATCATTTACCAGGAGAGTGGGAGAGG-3'

(SEQ ID No: 21)
5'CCGGATATCGCCACCATGGAGACAGACACACTCCTGCTATGGGTACTGCTGCTCTGGGTTCCAGGTT
CCACTGGTGACCATGCTGAAGGGACCTTTACCAGTG-3'

(SEQ ID No: 22)
5'-CGCGGATCCCTATCATTTACCAGGAGAGTGGGAGAGG-3'

(SEQ ID No: 23)
5'-CCGGATATCGCCACCATGGAGACAGACACACTCCTGCTATGGGTACTGCTGCTCTGGGTTCCAGGT
TCCACTGGTGACCCCAGCGAGACCGTCACC-3'

(SEQ ID No: 24)
5'-CGCGGATCCCTATCATTTACCAGGAGAGTGGGAGAGG-3'

(SEQ ID No: 25)
5'-AAGGATATCGATCGCAAATGTTGTGTCGAGTGCCCA-3'

(SEQ ID No: 26)
5'-CGTAAGCTTCATTTACCCGGAGACAGGGAGAG-3'

REFERENCE LIST

1. Bonner-Weir S 2000 Life and death of the pancreatic beta cells. Trends Endocrinol Metab 11:375-378
2. Bonner-Weir S 2000 Perspective: Postnatal pancreatic beta cell growth. Endocrinology 141:1926-1929
3. Wang Q, Brubaker P L 2002 Glucagon-like peptide-1 treatment delays the onset of diabetes in 8 week-old db/db mice. Diabetologia 45:1263-1273
4. Tourrel C, Bailbe D, Lacorne M, Meile M J, Kergoat M, Portha B 2002 Persistent improvement of type II diabetes in the Goto-Kakizaki rat model by expansion of the beta-cell mass during the prediabetic period with glucagon-like peptide-1 or exendin-4. Diabetes
5. Mandrup-Poulsen T 2003 Apoptotic signal transduction pathways in diabetes. Biochem Pharmacol 66:1433-1440
6. Mathis D, Vence L, Benoist C 2001 beta-Cell death during progression to diabetes. Nature 414:792-798

7. Sesti G 2002 Apoptosis in the beta cells: cause or consequence of insulin secretion defect in diabetes? Ann Med 34:444-450
8. Ogawa N, List J F, Habener J F, Maki T 2004 Cure of overt diabetes in NOD mice by transient treatment with anti-lymphocyte serum and exendin-4. Diabetes 53:1700-1705
9. Meier J J, Nauck M A 2005 Glucagon-like peptide 1(GLP-1) in biology and pathology. Diabetes Metab Res Rev 21:91-117
10. Keymeulen B, Vandemeulebroucke E, Ziegler A G, Mathieu C, Kaufman L, Hale G, Gorus F, Goldman M, Walter M, Candon S, Schandene L, Crenier L, De Block C, Seigneurin J M, De Pauw P, Pierard D, Weets I, Rebello P, Bird P, Berrie E, Frewin M, Waldmann H, Bach J F, Pipeleers D, Chatenoud L 2005 Insulin needs after CD3-antibody therapy in new-onset type I diabetes. N Engl J Med 352:2598-2608
11. Perfetti R, Merkel P 2000 Glucagon-like peptide-1: a major regulator of pancreatic beta-cell function. Eur J Endocrinol 143:717-725
12. Holst J J 1994 Glucagonlike peptide 1: a newly discovered gastrointestinal hormone. Gastroenterology 107:1848-1855
13. Brubaker P L, Drucker D J 2004 Minireview: Glucagon-like peptides regulate cell proliferation and apoptosis in the pancreas, gut, and central nervous system. Endocrinology 145:2653-2659
14. Perfetti R, Merkel P 2000 Glucagon-like peptide-1: a major regulator of pancreatic beta-cell function. Eur J Endocrinol 143:717-725
15. Nauck M A 2004 Glucagon-like peptide 1 (GLP-1) in the treatment of diabetes. Horm Metab Res 36:852-858
16. Drucker D J 2001 Minireview: the glucagon-like peptides. Endocrinology 142:521-527
17. Gutniak M, Orskov C, Hoist J J, Ahren B, Efendic S 1992 Antidiabetogenic effect of glucagon-like peptide-1 (7-36) amide in normal subjects and patients with diabetes mellitus. N Engl J Med 326:1316-1322
18. Dupre J, Behme M T, McDonald T J 2004 Exendin-4 normalized postcibal glycemic excursions in type I diabetes. J Clin Endocrinol Metab 89:3469-3473
19. Nauck M A, Heimesaat M M, Orskov C, Hoist J J, Ebert R, Creutzfeldt W 1993 Preserved incretin activity of glucagon-like peptide 1 [7-36 amide] but not of synthetic human gastric inhibitory polypeptide in patients with type-2 diabetes mellitus. J Clin Invest 91:301-307
20. Todd I F, Wilding J P, Edwards C M, Khan F A, Ghatei M A, Bloom S R 1997 Glucagon-like peptide-1 (GLP-1): a trial of treatment in non-insulin-dependent diabetes mellitus. Eur 3 Clin Invest 27:533-536
21. Drucker D J 1998 Glucagon-like peptides. Diabetes 47:159-169
22. Wang Q, Li L, Xu E, Wong V, Rhodes C, Brubaker P L 2004 Glucagon-like peptide-1 regulates proliferation and apoptosis via activation of protein kinase B in pancreatic INS-1 beta cells. Diabetologia 47:478-487
23. Eizirik D L, Mandrup-Poulsen T 2001 A choice of death—the signal-transduction of immune-mediated beta-cell apoptosis. Diabetologia 44:2115-2133
24. Saldeen J 2000 Cytokines induce both necrosis and apoptosis via a common Bcl-2-inhibitable pathway in rat insulin-producing cells. Endocrinology 141:2003-2010
25. Li L, El Kholy W, Rhodes C J, Brubaker P L 2005 Glucagon-like peptide-1 protects beta cells from cytokine-induced apoptosis and necrosis: role of protein kinase B. Diabetologia
26. Tourrel C, Bailbe D, Meile M J, Kergoat M, Portha B 2001 Glucagon-like peptide-1 and exendin-4 stimulate beta-cell neogenesis in streptozotocin-treated newborn rats resulting in persistently improved glucose homeostasis at adult age. Diabetes 50:1562
27. Finegood D T, Scaglia L, Bonner-Weir S 1995 Dynamics of beta-cell mass in the growing rat pancreas. Estimation with a simple mathematical model. Diabetes 44:249-256
28. Finegood D T, McArthur M D, Kojwang D, Thomas M I, Topp B G, Leonard T, Buckingham R E 2001 Beta-cell mass dynamics in Zucker diabetic fatty rats. Rosiglitazone prevents the rise in net cell death. Diabetes 50:1021-1029
29. Shapiro A M, Lakey J R, Ryan E A, Korbutt G S, Toth E, Warnock G L, Kneteman N M, Rajotte R V 2000 Islet transplantation in seven patients with type I diabetes mellitus using a glucocorticoid-free immunosuppressive regimen. N Eng J Med 343:230-238
30. Kieffer T J, McIntosh C H, Pederson R A 1995 Degradation of glucose-dependent insulinotropic polypeptide and truncated glucagon-like peptide 1 in vitro and in vivo by dipeptidyl peptidase IV. Endocrinology 136:3585-3596
31. Mentlein R, Gallwitz B, Schmidt W E 1993 Dipeptidyl-peptidase IV hydrolyses gastric inhibitory polypeptide, glucagon-like peptide-1 (7-36)amide, peptide histidine methionine and is responsible for their degradation in human serum. Eur 3 Biochem
32. Montrose-Rafizadeh C, Avdonin P, Garant M J, Rodgers B D, Kole S, Yang H, Levine M A, Schwindinger W, Bernier M 1999 Pancreatic glucagon-like peptide-1 receptor couples to multiple G proteins and activates mitogen-activated protein kinase pathways in Chinese hamster ovary cells. Endocrinology 140:1132-1140
33. Toft-Nielsen M B, Madsbad S, Holst J J 1999 Continuous subcutaneous infusion of glucagon-like peptide 1 lowers plasma glucose and reduces appetite in type II diabetic patients. Diabetes Care 22:1137-1143
34. Ahren B, Simonsson E, Larsson H, Landin-Olsson M, Torgeirsson H, Jansson P A, Sandqvist M, Bavenholm P, Efendic S, Eriksson J W, Dickinson S, Holmes D 2002 Inhibition of dipeptidyl peptidase IV improves metabolic control over a 4-week study period in type II diabetes. Diabetes Care 25:869-875
35. Green B D, Gault V A, Mooney M H, Irwin N, Bailey C J, Harriott P, Greer B, Flatt P R, O'Harte F P 2003 Novel dipeptidyl peptidase IV resistant analogues of glucagon-like peptide-1(7-36)amide have preserved biological activities in vitro conferring improved glucose-lowering action in vivo. J Mol Endocrinol 31:529-540
36. Green B D, Mooney M H, Gault V A, Irwin N, Bailey C J, Harriott P, Greer B, O'Harte F P, Flatt P R 2004 N-terminal His(7)-modification of glucagon-like peptide-1(7-36) amide generates dipeptidyl peptidase IV-stable analogues with potent antihyperglycaemic activity. J Endocrinol 180:379-388
37. Chang A M, Jakobsen G, Sturis J, Smith M J, Bloem C J, An B, Galecki A, Halter J B 2003 The GLP-1 derivative NN2211 restores beta-cell sensitivity to glucose in type II diabetic patients after a single dose. Diabetes 52:1786-1791
38. Liu H K, Green B D, Gault V A, McCluskey J T, McClenaghan N H, O'Harte F P, Flatt P R 2004 N-acetyl-GLP-1: a DPP IV-resistant analogue of glucagon-like peptide-1 (GLP-1) with improved effects on pancreatic beta-cell-associated gene expression. Cell Biol Int 28:69-73
39. Fineman M S, Bicsak T A, Shen L Z, Taylor K, Gaines E, Varns A, Kim D, Baron A D 2003 Effect on glycemic control of exenatide (synthetic exendin-4) additive to existing metformin and/or sulfonylurea treatment in patients with type II diabetes. Diabetes Care 26:2370-2377
40. Kim J G, Baggio L L, Bridon D P, Castaigne J P, Robitaille M F, Jette L, Benquet C, Drucker D J 2003 Development and characterization of a glucagon-like peptide 1-albumin conjugate: the ability to activate the glucagon-like peptide 1 receptor in vivo. Diabetes 52:751-759
41. Ahangari G, Ostadali M R, Rabani A, Rashidian J, Sanati M H, Zarindast M R 2004 Growth hormone antibodies formation in patients treated with recombinant human growth hormone. Int J Immunopathol Pharmacol 17:33-38
42. Lee A Y, Chey W Y, Choi J, Jeon J S 2002 Insulin-induced drug eruptions and reliability of skin tests. Acta Derm Venereol 82:114-117
43. Prud'homme G J 2004 Altering immune tolerance therapeutically: the power of negative thinking. J Leukoc Biol 75:586-599
44. Takai T 2005 Fc receptors and their role in immune regulation and autoimmunity. J Clin Immunol 25:1-18
45. Ravetch I V, Lanier L L 2000 Immune inhibitory receptors. Science 290:84-89
46. Ravetch J V, Bolland S 2001 IgG Fc receptors. Annu Rev Immunol 19:275-290
47. King L B, Monroe J G 2000 Immunobiology of the immature B cell: plasticity in the B-cell antigen receptor-induced response fine tunes negative selection. Immunol Rev 176:86-104
48. Melo M E, Qian J, El Amine M, Agarwal R K, Soukhareva N, Kang Y, Scott D W 2002 Gene transfer of Ig-fusion proteins into B cells prevents and treats autoimmune diseases. J Immunol 168:4788-4795
49. Liu E, Moriyama H, Abiru N, Paronen J, Devendra D, Finkelman F D, Eisenbarth G S 2004 Preventing peptide-induced anaphylaxis: addition of C-terminal amino acids to produce a neutral isoelectric point. J Allergy Clin Immunol 114:607-613
50. Zhu D, Kepley C L, Zhang K, Terada T, Yamada T, Saxon A 2005 A chimeric human-cat fusion protein blocks cat-induced allergy. Nat Med 11:446-449
51. Juneja R, Palmer J P 1999 Type I 1/2 diabetes: myth or reality? Autoimmunity
52. Gianani R, Eisenbarth G S 2005 The stages of type IA diabetes: 2005. Immunol Rev 204:232-249
53. Anderson M S, Bluestone J A 2005 The NOD mouse: a model of immune dysregulation. Annu Rev Immunol 23:447-485
54. Prud'homme G J, Lawson B R, Theofilopoulos A N 2001 Anticytokine gene therapy of autoimmune diseases. Expert Opin Biol Ther 1:359-373
55. Prud'homme G J, Lawson B R, Chang Y, Theofilopoulos A N 2001 Immunotherapeutic gene transfer into muscle. Trends Immunol 22:149-155
56. Kapturczak M H, Flotte T, Atkinson M A 2001 Adeno-associated virus (MV) as a vehicle for therapeutic gene delivery: improvements in vector design and viral production enhance potential to prolong graft survival in pancreatic islet cell transplantation for the reversal of type I diabetes. Curr Mol Med 1:245-258
57. Contreras J L, Bilbao G, Smyth C A, Eckhoff D E, Jiang X L, Jenkins S, Thomas Fr, Curiel D T, Thomas J M 2002 Cytoprotection of pancreatic islets before and early after transplantation using gene therapy. Kidney Int 61:79-84
58. Rabinovitch A, Suarez-Pinzon W, Strynadka K, Ju Q, Edelstein D, Brownlee M, Korbutt G S, Rajotte R V 1999 Transfection of human pancreatic islets with an anti-apoptotic gene (bcl-2) protects beta-cells from cytokine-induced destruction. Diabetes 48:1223-1229
59. Giannoukakis N, Trucco M 2003 Current status and prospects for gene and cell therapeutics for type I diabetes mellitus. Rev Endocr Metab Disord 4:369-380
60. Giannoukakis N, Trucco M 2003 Gene therapy technology applied to disorders of glucose metabolism: promise, achievements, and prospects. Biotechniques 35:122-145
61. Yechoor V, Chan L 2005 Gene therapy progress and prospects: gene therapy for diabetes mellitus. Gene Ther 12:101-107
62. Jun H S, Yoon J W 2005 Approaches for the cure of type I diabetes by cellular and gene therapy. Curr Gene Ther 5:249-262
63. Croze F, Prud'homme G J 2003 Gene therapy of streptozotocin-induced diabetes by intramuscular delivery of modified preproinsulin genes. J Gene Med 5:425-437
64. Ferber S, Halkin A, Cohen H, Ber I, Einav Y, Goldberg I, Barshack I, Seijffers R, Kopolovic J, Kaiser N, Karasik A 2000 Pancreatic and duodenal homeobox gene 1 induces expression of insulin genes in liver and ameliorates streptozotocin-induced hyperglycemia. Nat Med 6:568-572
65. Piccirillo C A, Prud'homme G J 2003 Immune modulation by plasmid DNA-mediated cytokine gene transfer. Curr Pharm Des 9:83-94
66. Piccirillo C A, Prud'homme G J 2003 Gene therapy with plasmids encoding cytokine- or cytokine receptor—IgG chimeric proteins. Methods Mol Biol 215:153-170
67. Belghith M, Bluestone J A, Barriot S, Megret J, Bach J F, Chatenoud L 2003 TGF-beta-dependent mechanisms mediate restoration of self-tolerance induced by antibodies to CD3 in overt autoimmune diabetes. Nat Med 9:1202-1208
68. Herold K C, Gitelman S E, Masharani U, Hagopian W, Bisikirska B, Donaldson D, Rother K, Diamond B, Harlan D M, Bluestone J A 2005 A single course of anti-CD3 monoclonal antibody hOKT3gamma1(Ala-Ala) results in improvement in C-peptide responses and clinical parameters for at least 2 years after onset of type I diabetes. Diabetes 54:1763-1769
69. Lazetic S, Leong S R, Chang J C, Ong R, Dawes G, Punnonen J 2002 Chimeric co-stimulatory molecules that selectively act through CD28 or CTLA-4 on human T cells. J Biol Chem 277:38660-38668
70. Andre F, Mir L M 2004 DNA electrotransfer: its principles and an updated review of its therapeutic applications. Gene Ther 11 Suppl 1:S33-S42
71. Li S 2004 Electroporation gene therapy: new developments in vivo and in vitro. Curr Gene Ther 4:309-316
72. Wells D J 2004 Gene therapy progress and prospects: electroporation and other physical methods. Gene Ther 11:1363-1369
73. Bloquel C, Fabre E, Bureau M F, Scherman D 2004 Plasmid DNA electrotransfer for intracellular and secreted proteins expression: new methodological developments and applications. J Gene Med 6 Suppl 1:S11-S23
74. Fattori E, La Monica N. Ciliberto G, Toniatti C 2002 Electro-gene-transfer: a new approach for muscle gene delivery. Somat Cell Mol Genet. 27:75-83
75. Herweijer H, Wolff J A 2003 Progress and prospects: naked DNA gene transfer and therapy. Gene Ther 10:453-458
76. van Drunen Littel-van den Hurk, Babiuk S L, Babiuk L A 2004 Strategies for improved formulation and delivery of DNA vaccines to veterinary target species. Immunol Rev 199:113-125

77. Brubaker P L, Drucker D J 2002 Structure-function of the glucagon receptor family of G protein-coupled receptors: the glucagon, GIP, GLP-1, and GLP-2 receptors. Receptors Channels 8:179-188
78. Ozmen L, Gribaudo G, Fountoulakis M, Gentz R, Landolfo S, Garotta G 1993 Mouse soluble IFN gamma receptor as IFN gamma inhibitor. Distribution, antigenicity, and activity after injection in mice. J Immunol 150: 2698-2705
79. Kurschner C, Garotta G, Dembic Z 1992 Construction, purification, and characterization of new interferon gamma (IFN gamma) inhibitor proteins. Three IFN gamma receptor-immunoglobulin hybrid molecules. J Biol Chem 267: 9354-9360
80. Kurschner C, Ozmen L, Garotta G, Dembic Z 1992 IFN-gamma receptor-Ig fusion proteins. Half-life, immunogenicity, and in vivo activity. J Immunol 149:4096-4100
81. George S R, O'Dowd B F, Lee S P 2002 G-protein-coupled receptor oligomerization and its potential for drug discovery. Nat Rev Drug Discov 1:808-820
82. Dupuis D S, Perez M, Halazy S, Colpaert F C, Pauwels P J 1999 Magnitude of 5-HT1B and 5-HT1A receptor activation in guinea-pig and rat brain: evidence from sumatriptan dimer-mediated [35S]GTPgammaS binding responses. Brain Res Mol Brain Res
83. Jungbauer A, Tauer C, Reiter M, Purtscher M, Wenisch E, Steindl F, Buchacher A, Katinger H 1989 Comparison of protein A, protein G and copolymerized hydroxyapatite for the purification of human monoclonal antibodies. J Chromatogr 476:257-268
84. Leiter E H 1989 The genetics of diabetes susceptibility in mice. FASEB J
85. Bonner-Weir S, Weir G C 2005 New sources of pancreatic beta-cells. Nat Biotechnol 23:857-861
86. Effect of intensive blood-glucose control with metformin on complications in overweight patients with type II diabetes (UKPDS 34). UK Prospective Diabetes Study (UKPDS) Group 1998 Lancet 352:854-865
87. Gerich J E 2002 Redefining the clinical management of type II diabetes: matching therapy to pathophysiology. Eur J Clin Invest 32 Suppl 3:46-53
88. Szayna M, Doyle M E, Betkey J A, Holloway H W, Spencer R G, Greig N H, Egan J M 2000 Exendin-4 decelerates food intake, weight gain, and fat deposition in Zucker rats. Endocrinology 141:1936-1941
89. Drucker D J 2001 Development of glucagon-like peptide-1-based pharmaceuticals as therapeutic agents for the treatment of diabetes. Curr Pharm Des
90. Larsen P J, Fledelius C, Knudsen L B, Tang-Christensen M 2001 Systemic administration of the long-acting GLP-1 derivative NN2211 induces lasting and reversible weight loss in both normal and obese rats. Diabetes 50:2530-2539
91. Rolin B, Larsen M O, Gotfredsen C F, Deacon C F, Carr R D, Wilken M, Knudsen L B 2002 The long-acting GLP-1 derivative NN2211 ameliorates glycemia and increases beta-cell mass in diabetic mice. Am J Physiol Endocrinol Metab 283:E745-E752
92. Baggio L L, Huang Q, Brown T J, Drucker D J 2004 A recombinant human glucagon-like peptide (GLP)-1-albumin protein (albugon) mimics peptidergic activation of GLP-1 receptor-dependent pathways coupled with satiety, gastrointestinal motility, and glucose homeostasis. Diabetes 53:2492-2500
93. Larrick J W, Fry K E 1991 Recombinant antibodies. Hum Antibodies Hybridomas 2:172-189
94. Weir A N, Nesbitt A, Chapman A P, Popplewell A G, Antoniw P, Lawson A D 2002 Formatting antibody fragments to mediate specific therapeutic functions. Biochem Soc Trans 30:512-516
95. Hupe-Sodmann K, McGregor G P, Bridenbaugh R, Goke R, Goke B, Thole H, Zimmermann B, Voigt K 1995 Characterisation of the processing by human neutral endopeptidase 24.11 of GLP-1 (7-36) amide and comparison of the substrate specificity of the enzyme for other glucagon-like peptides. Regul Pept 58:149-156
96. Herberg L, Coleman D L 1977 Laboratory animals exhibiting obesity and diabetes syndromes. Metabolism 26:59-99
97. Chen H, Charlat O, Tartaglia L A, Woolf E A, Weng X, Ellis S J, Lakey N D, Culpepper J, Moore K J, Breitbart R E, Duyk G M, Tepper R I, Morgenstern J P 1996 Evidence that the diabetes gene encodes the leptin receptor: identification of a mutation in the leptin receptor gene in db/db mice. Cell 84:491-495
98. Turton M D, O'Shea D, Gunn I, Beak S A, Edwards C M, Meeran K, Choi S J, Taylor G M, Heath M M, Lambert P D, Wilding J P, Smith D M, Ghatei M A, Herbert J, Bloom S R 1996 A role for glucagon-like peptide-1 in the central regulation of feeding. Nature 379:69-72
99. Weyer C, Bogardus C, Mott D M, Pratley R E 1999 The natural history of insulin secretory dysfunction and insulin resistance in the pathogenesis of type II diabetes mellitus. J Clin Invest 104:787-794
100. Weyer C, Bogardus C, Pratley R E 1999 Metabolic characteristics of individuals with impaired fasting glucose and/or impaired glucose tolerance. Diabetes 48:2197-2203
101. Schick R R, Zimmermann J P, vorm W T, Schusdziarra V 2003 Peptides that regulate food intake: glucagon-like peptide 1-(7-36) amide acts at lateral and medial hypothalamic sites to suppress feeding in rats. Am J Physiol Regul Integr Comp Physiol 284: R1427-R1435
102. Dupre J 2005 Glycaemic effects of incretins in Type I diabetes mellitus: a concise review, with emphasis on studies in humans. Regul Pept 128:149-157
103. Gregg R K, Jain R, Schoenleber S J, Divekar R, Bell J J, Lee H H, Yu P, Zaghouani H 2004 A sudden decline in active membrane-bound TGF-beta impairs both T regulatory cell function and protection against autoimmune diabetes. J Immunol 173:7308-7316
104. You S, Belghith M, Cobbold S, Alyanakian M A, Gouarin C, Barriot S, Garcia C, Waldmann H, Bach J F, Chatenoud L 2005 Autoimmune diabetes onset results from qualitative rather than quantitative age-dependent changes in pathogenic T-cells. Diabetes
105. Piccirillo C A, Chang Y, Prud'homme G J 1998 TGF-beta1 somatic gene therapy prevents autoimmune disease in nonobese diabetic mice. J Immunol 161:3950-3956
106. Piccirillo C A, Thornton A M 2004 Cornerstone of peripheral tolerance: naturally occurring CD4+ CD25+ regulatory T cells. Trends Immunol 25:374-380
107. Sakaguchi S 2005 Naturally arising Foxp3-expressing CD25+CD4+ regulatory T cells in immunological tolerance to self and non-self. Nat Immunol 6:345-352
108. Paust S, Cantor H 2005 Regulatory T cells and autoimmune disease. Immunol Rev 204:195-207
109. Tang Q, Boden E K, Henriksen K J, Bour-Jordan H, Bi M, Bluestone J A 2004 Distinct roles of CTLA-4 and TGF-beta in CD4+ CD25+ regulatory T cell function. Eur J Immunol 34:2996-3005
110. Guo Y, Wu Y, Zhao M, Kong X P, Liu Y 1995 Mutational analysis and an alternatively spliced product of B7 defines its CD28/CTLA4-binding site on immunoglobulin C-like domain. J Exp Med 181:1345-1355

111. Guo Y, Wu Y, Kong X, Liu Y 1998 Identification of conserved amino acids in murine B7-1IgV domain critical for CTLA4/CD28:B7 interaction by site-directed mutagenesis: a novel structural model of the binding site. Mol Immunol 35:215-225

112. Chakrabarti R, Zhou Z F, Chang Y, Prud'homme G J 2005 A mutant B7-1/Ig fusion protein that selectively binds to CTLA-4 ameliorates anti-tumor DNA vaccination and counters regulatory T cell activity. Vaccine 113. Prud'homme G J, Chang Y, Li X 2002 Immunoinhibitory DNA vaccine protects against autoimmune diabetes through cDNA encoding a selective CTLA-4 (CD152) ligand. Hum Gene Ther 13:395-406

114. McGaha T L, Sorrentino B, Ravetch I V 2005 Restoration of tolerance in lupus by targeted inhibitory receptor expression. Science 307:590-593

115. Fukuyama H, Nimmerjahn F, Ravetch J V 2005 The inhibitory Fcgamma receptor modulates autoimmunity by limiting the accumulation of immunoglobulin G+ anti-DNA plasma cells. Nat Immunol 6:99-106

116. Prud'homme G J, Chang Y 1999 Prevention of autoimmune diabetes by intramuscular gene therapy with a non-viral vector encoding an interferon-gamma receptor/IgG1 fusion protein. Gene Ther 6:771-777

117. Wolff J A, Malone R W, Williams P, Chong W, Acsadi G, Jani A, Feigner P L 1990 Direct gene transfer into mouse muscle in vivo. Science 247:1465-1468

118. Wolff J A, Williams P, Acsadi G, Jiao S, Jani A, Chong W 1991 Conditions affecting direct gene transfer into rodent muscle in vivo. Biotechniques 11:474-485

119. Mir L M, Bureau M F, Gehl J, Rangara R, Rouy D, Caillaud J M, Delaere P, Branellec D, Schwartz B, Scherman D 1999 High-efficiency gene transfer into skeletal muscle mediated by electric pulses. Proc Natl Acad Sci USA 96:4262-4267

120. Mathiesen I 1999 Electropermeabilization of skeletal muscle enhances gene transfer in vivo. Gene Ther 6:508-514

121. Prinz W A, Aslund F, Holmgren A, Beckwith J 1997 The role of the thioredoxin and glutaredoxin pathways in reducing protein disulfide bonds in the *Escherichia coli* cytoplasm. J Biol Chem 272:15661-15667

122. Kurland C, Gallant J 1996 Errors of heterologous protein expression. Curr Opin Biotechnol 7:489-493

123. HUNTER W M, GREENWOOD FC 1962 Preparation of iodine-131 labelled human growth hormone of high specific activity. Nature 194:495-496

124. Wang Q, Wu Y, Aerts T, Slegers H, Clauwaert J 1998 Expression of IGF-I and IGF-II receptors in rat C6 glioma cells as a function of the growth phase. Cell Physiol Biochem 8:304-313

125. Lee D K, Lynch K R, Nguyen T, Im D S, Cheng R, Saldivia V R, Liu Y, Liu I S, Heng H H, Seeman P, George S R, O'Dowd B F, Marchese A 2000 Cloning and characterization of additional members of the G protein-coupled receptor family. Biochim Biophys Acta 1490:311-323

126. Wang Q, Bilan P J, Tsakiridis T, Hinek A, Klip A 1998 Actin filaments participate in the relocalization of phosphatidylinositol3-kinase to glucose transporter-containing compartments and in the stimulation of glucose uptake in 3T3-L1 adipocytes. Biochem J 331:917-928

127. Wang Q, Somwar R, Bilan P J, Liu Z, Jin J, Woodgett J R, Klip A 1999 Protein kinase B/Akt participates in GLUT4 translocation by insulin in L6 myoblasts. Mol Cell Biol 128. Chang Y, Prud'homme G J 1999 Intramuscular administration of expression plasmids encoding interferon-gamma receptor/IgG1 or IL-4/IgG1 chimeric proteins protects from autoimmunity. J Gene Med 1:415-423

129. Hartikka J, Sawdey M, Cornefert-Jensen F, Margalith M, Barnhart K, Nolasco M, Vahlsing H L, Meek J, Marquet M, Hobart P, Norman J, Manthorpe M 1996 An improved plasmid DNA expression vector for direct injection into skeletal muscle. Hum Gene Ther 130. Glinka Y, De Pooter R, Croze F, Prud'homme G J 2003 Regulatory cytokine production stimulated by DNA vaccination against an altered form of glutamic acid decarboxylase 65 in nonobese diabetic mice. J Mol Med 81:175-184

131. Prud'homme G J, Glinka Y. DNA vaccines that induce regulatory T cells and protect against autoimmune diabetes. Gene Therapy and Molecular Biology, 09, [Epub ahead of print]. 2005.
Ref Type: Generic 132. Kaufman D L, Tisch R, Sarvetnick N, Chatenoud L, Harrison L C, Haskins K, Quinn A, Sercarz E, Singh B, von Herrath M, Wegmann D, Wen L, Zekzer D 2001 Report from the 1st International NOD Mouse T-Cell Workshop and the follow-up mini-workshop. Diabetes 50:2459-2463

133. Pop S M, Wong C P, Culton D A, Clarke S H, Tisch R 2005 Single cell analysis shows decreasing FoxP3 and TGFbeta1 coexpressing CD4+ CD25+ regulatory T cells during autoimmune diabetes. J Exp Med 201:1333-1346

134. Balasa B, Boehm B O, Fortnagel A, Karges W, Van Gunst K, Jung N, Camacho S A, Webb S R, Sarvetnick N 2001 Vaccination with glutamic acid decarboxylase plasmid DNA protects mice from spontaneous autoimmune diabetes and B7/CD28 costimulation circumvents that protection. Clin Immunol 99:241-252

135. Ruprecht C R, Gattorno M, Ferlito F, Gregorio A, Martini A, Lanzavecchia A, Sallusto F 2005 Coexpression of CD25 and CD27 identifies FoxP3+ regulatory T cells in inflamed synovia. J Exp Med 201:1793-1803

136. Prud'homme G I, Piccirillo C A 2000 The inhibitory effects of transforming growth factor-beta-1 (TGF-beta1) in autoimmune diseases. J Autoimmun 14:23-42

The invention claimed is:

1. A composition for the treatment of type I diabetes in a subject, said composition comprising:
   a GLP-1/IgG fusion protein, wherein said GLP-1 polypeptide is selected from the group consisting of GLP-1(7-37)OH, GLP-1(7-36)amide (SEQ ID NO:1), a DPPIV resistant GLP-1 Ala[8] mutant and a DPPIV resistant GLP-1 His[7] mutant; and the IgG is human IgG2: and
   an autoimmune suppressor comprising at least one antigenic target epitope of a pancreatic beta-cell associated antigen for decreasing autoimmunity against islet beta cells, wherein said pancreatic beta-cell associated antigen is pre-proinsulin comprising SEQ ID NO:8, GAD65 comprising SEQ ID NO:9, 10 and/or 11, or pre-proinsulin/GAD65 (PPI/GAD65) comprising SEQ ID NO:8 and SEQ ID NO: 9, 10 and/or 11.

2. The composition of claim 1, wherein said IgG comprises an Fc portion of the IgG or a fragment or variant of the Fc portion.

3. The composition of claim 1, further comprising B7-1wa molecule which is a T cell negative regulatory molecule.

4. The composition of claim 1, wherein said DPPIV resistant GLP-1 Ala[8] mutant is GLP-1A8G.

* * * * *

UNITED STATES PATENT AND TRADEMARK OFFICE
CERTIFICATE OF CORRECTION

PATENT NO. : 8,278,420 B2
APPLICATION NO. : 11/997996
DATED : October 2, 2012
INVENTOR(S) : Qinghua Wang et al.

Page 1 of 1

It is certified that error appears in the above-identified patent and that said Letters Patent is hereby corrected as shown below:

On the title page, under item "(75) Inventors:", delete "Mohan Kumar, Toronto (CA)".

Signed and Sealed this
Twenty-fifth Day of December, 2012

David J. Kappos
*Director of the United States Patent and Trademark Office*

UNITED STATES PATENT AND TRADEMARK OFFICE
CERTIFICATE OF CORRECTION

PATENT NO.         : 8,278,420 B2
APPLICATION NO.    : 11/997996
DATED              : October 2, 2012
INVENTOR(S)        : Qinghua Wang et al.

It is certified that error appears in the above-identified patent and that said Letters Patent is hereby corrected as shown below:

In the Claims:

Please delete the term "or variant" in column 72, line 41 (claim 2, line 2).

Signed and Sealed this
Seventh Day of May, 2013

Teresa Stanek Rea
*Acting Director of the United States Patent and Trademark Office*